(12) United States Patent
Fallin et al.

(10) Patent No.: US 12,383,253 B2
(45) Date of Patent: Aug. 12, 2025

(54) SUTURE ANCHOR

(71) Applicant: CROSSROADS EXTREMITY SYSTEMS, LLC, Memphis, TN (US)

(72) Inventors: T. Wade Fallin, Hyde Park, UT (US); Joel Helgerson, Erie, CO (US); Michael Chad Hollis, Collierville, TN (US); Daniel Sayger, Hernando, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 911 days.

(21) Appl. No.: 17/462,369

(22) Filed: Aug. 31, 2021

(65) Prior Publication Data
US 2022/0000470 A1   Jan. 6, 2022

Related U.S. Application Data

(63) Continuation-in-part of application No. 16/871,485, filed on May 11, 2020, now Pat. No. 11,937,801, and
(Continued)

(51) Int. Cl.
*A61B 17/04*   (2006.01)
*A61B 17/06*   (2006.01)
(Continued)

(52) U.S. Cl.
CPC .... *A61B 17/0401* (2013.01); *A61B 17/06133* (2013.01); *A61F 2/0811* (2013.01);
(Continued)

(58) Field of Classification Search
CPC .......... A61B 17/0485; A61B 17/06133; A61B 17/0401; A61B 2017/0053;
(Continued)

(56) References Cited

U.S. PATENT DOCUMENTS 1,583,271 A    5/1926   Biro
1,586,721 A    6/1926   Tryon
(Continued)

FOREIGN PATENT DOCUMENTS

WO    95/15726 A1    6/1995
WO    98/06344 A1    2/1998
(Continued)

OTHER PUBLICATIONS 2.5 mm PushLock Knotless Suture Anchor, Arthrex, Inc., www.arthrex.com, 2013, 2 pp.
(Continued)

*Primary Examiner* — Tuan V Nguyen
(74) *Attorney, Agent, or Firm* — BakerHostetler

(57) ABSTRACT

A knotless suture anchor system is disclosed for improved anchoring in tissue. The knotless suture anchor system includes an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a distal opening communicating with the longitudinal passageway nearer the distal end. The knotless suture anchor system also includes an interference member insertable distally into the longitudinal passageway to secure a portion of a suture within the longitudinal passageway by compressing the portion of the suture between the interference member and the anchor body, and a frangible connection that joins a proximal member to the anchor body.

19 Claims, 36 Drawing Sheets

Related U.S. Application Data a continuation-in-part of application No. 16/545,371, filed on Aug. 20, 2019, now Pat. No. 11,241,225, and a continuation-in-part of application No. 16/268,973, filed on Feb. 6, 2019, now Pat. No. 11,103,233, said application No. 16/545,371 is a continuation of application No. 15/641,592, filed on Jul. 5, 2017, now Pat. No. 10,426,459, said application No. 16/871,485 is a continuation of application No. 15/641,573, filed on Jul. 5, 2017, now Pat. No. 10,682,131, said application No. 16/268,973 is a continuation of application No. 15/224,273, filed on Jul. 29, 2016, now Pat. No. 10,226,243.

(60) Provisional application No. 62/458,975, filed on Feb. 14, 2017, provisional application No. 62/456,217, filed on Feb. 8, 2017, provisional application No. 62/425,560, filed on Nov. 22, 2016, provisional application No. 62/358,231, filed on Jul. 5, 2016, provisional application No. 62/200,696, filed on Aug. 4, 2015.

(51) Int. Cl.
  *A61F 2/08* (2006.01)
  *A61B 17/00* (2006.01)
  *A61B 90/00* (2016.01)
  *A61B 90/92* (2016.01)

(52) U.S. Cl.
  CPC .......... *A61B 2017/0053* (2013.01); *A61B 2017/0403* (2013.01); *A61B 2017/0409* (2013.01); *A61B 2017/0412* (2013.01); *A61B 2017/0414* (2013.01); *A61B 2017/0424* (2013.01); *A61B 2017/0425* (2013.01); *A61B 2017/045* (2013.01); *A61B 2017/0458* (2013.01); *A61B 17/0485* (2013.01); *A61B 2090/037* (2016.02); *A61B 2090/0807* (2016.02); *A61B 90/92* (2016.02); *A61F 2002/0835* (2013.01); *A61F 2002/0882* (2013.01)

(58) Field of Classification Search
  CPC .... A61B 2017/0403; A61B 2017/0409; A61B 2017/0412; A61B 2017/0424; A61B 2017/0425; A61B 2017/045; A61F 2/0811
  See application file for complete search history.

(56) References Cited

U.S. PATENT DOCUMENTS

| | | |
|---|---|---|
| 1,856,721 A | 5/1932 | Nagelmann |
| 2,291,413 A | 7/1942 | Siebrandt |
| 4,312,337 A | 1/1982 | Donohue |
| 4,441,497 A | 4/1984 | Paudler |
| 4,622,960 A | 11/1986 | Tam |
| 4,672,957 A | 6/1987 | Hourahane |
| 4,738,255 A | 4/1988 | Goble et al. |
| 4,741,330 A | 5/1988 | Hayhurst |
| 4,784,126 A | 11/1988 | Hourahane |
| 4,809,408 A | 3/1989 | Abrahamson |
| 4,890,615 A | 1/1990 | Caspari et al. |
| 4,898,156 A | 2/1990 | Gatturna et al. |
| 4,959,069 A | 9/1990 | Brennan et al. |
| 5,037,422 A | 8/1991 | Hayhurst et al. |
| 5,041,129 A | 8/1991 | Hayhurst et al. |
| 5,100,417 A | 3/1992 | Cerier et al. |
| 5,176,682 A | 1/1993 | Chow |
| 5,224,946 A | 7/1993 | Hayhurst et al. |
| 5,236,445 A | 8/1993 | Hayhurst et al. |
| 5,250,055 A | 10/1993 | Moore et al. |
| 5,254,126 A | 10/1993 | Filipi et al. |
| 5,257,996 A | 11/1993 | McGuire |
| 5,258,016 A | 11/1993 | Dipoto et al. |
| 5,268,001 A | 12/1993 | Nicholson et al. |
| 5,269,809 A | 12/1993 | Hayhurst et al. |
| 5,312,438 A | 5/1994 | Johnson |
| 5,330,468 A | 7/1994 | Burkhart |
| 5,336,240 A | 8/1994 | Metzler et al. |
| 5,342,369 A | 8/1994 | Harryman, II |
| 5,350,380 A | 9/1994 | Goble et al. |
| 5,354,300 A | 10/1994 | Goble et al. |
| 5,411,523 A | 5/1995 | Goble |
| 5,417,691 A | 5/1995 | Hayhurst |
| 5,417,701 A | 5/1995 | Holmes |
| 5,439,467 A | 8/1995 | Benderev et al. |
| 5,454,823 A | 10/1995 | Richardson et al. |
| 5,464,427 A | 11/1995 | Curtis et al. |
| 5,466,243 A | 11/1995 | Schmieding et al. |
| 5,480,403 A | 1/1996 | Lee et al. |
| 5,486,197 A | 1/1996 | Le et al. |
| 5,544,664 A | 8/1996 | Benderev et al. |
| 5,545,180 A | 8/1996 | Le et al. |
| 5,562,683 A | 10/1996 | Chan |
| 5,562,684 A | 10/1996 | Kammerer |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer et al. |
| 5,584,836 A | 12/1996 | Ballintyn et al. |
| 5,584,839 A | 12/1996 | Gieringer |
| 5,601,557 A | 2/1997 | Hayhurst |
| 5,601,562 A | 2/1997 | Wolf et al. |
| 5,620,012 A | 4/1997 | Benderev et al. |
| 5,624,446 A | 4/1997 | Harryman, II |
| 5,630,824 A | 5/1997 | Hart |
| 5,637,112 A | 6/1997 | Moore et al. |
| 5,643,321 A | 7/1997 | McDevitt |
| 5,645,568 A | 7/1997 | Chervitz et al. |
| 5,647,874 A | 7/1997 | Hayhurst |
| 5,649,963 A | 7/1997 | McDevitt |
| 5,658,313 A | 8/1997 | Thal |
| 5,665,112 A | 9/1997 | Thal |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,688,284 A | 11/1997 | Chervitz et al. |
| 5,690,676 A | 11/1997 | Dipoto et al. |
| 5,690,677 A | 11/1997 | Schmieding et al. |
| 5,700,266 A | 12/1997 | Harryman, II |
| 5,702,397 A | 12/1997 | Goble et al. |
| 5,702,398 A | 12/1997 | Tarabishy |
| 5,709,708 A | 1/1998 | Thal |
| 5,720,765 A | 2/1998 | Thal |
| 5,725,529 A | 3/1998 | Nicholson et al. |
| 5,728,136 A | 3/1998 | Thal |
| 5,730,747 A | 3/1998 | Ek et al. |
| 5,733,307 A | 3/1998 | Dinsdale |
| 5,746,754 A | 5/1998 | Chan |
| 5,746,763 A | 5/1998 | Benderev et al. |
| 5,749,884 A | 5/1998 | Benderev et al. |
| 5,755,728 A | 5/1998 | Maki |
| 5,766,221 A | 6/1998 | Benderev et al. |
| 5,776,151 A | 7/1998 | Chan |
| 5,782,864 A | 7/1998 | Lizardi |
| 5,797,963 A | 8/1998 | McDevitt |
| 5,800,447 A | 9/1998 | Wenstrom, Jr. |
| 5,814,071 A | 9/1998 | McDevitt et al. |
| 5,824,009 A | 10/1998 | Fukuda et al. |
| RE36,020 E | 12/1998 | Moore et al. |
| 5,842,478 A | 12/1998 | Benderev et al. |
| 5,860,978 A | 1/1999 | McDevitt et al. |
| 5,868,762 A | 2/1999 | Cragg et al. |
| 5,891,150 A | 4/1999 | Chan |
| 5,891,168 A | 4/1999 | Thal |
| 5,895,425 A | 4/1999 | Grafton et al. |
| 5,906,624 A | 5/1999 | Wenstrom, Jr. |
| 5,911,721 A | 6/1999 | Nicholson et al. |
| 5,918,604 A | 7/1999 | Whelan |

(56) References Cited

U.S. PATENT DOCUMENTS

| | | |
|---|---|---|
| 5,935,129 A | 8/1999 | McDevitt et al. |
| 5,938,686 A | 8/1999 | Benderev et al. |
| 5,947,982 A | 9/1999 | Duran |
| 5,948,000 A | 9/1999 | Larsen et al. |
| 5,957,924 A | 9/1999 | Toermaelae et al. |
| 5,961,530 A | 10/1999 | Moore et al. |
| 5,964,783 A | 10/1999 | Grafton et al. |
| 5,968,044 A | 10/1999 | Nicholson et al. |
| 5,980,558 A | 11/1999 | Wiley |
| 6,001,104 A | 12/1999 | Benderev et al. |
| 6,024,758 A | 2/2000 | Thal |
| 6,029,805 A | 2/2000 | Alpern et al. |
| 6,045,574 A | 4/2000 | Thal |
| 6,086,608 A | 7/2000 | Ek et al. |
| 6,099,538 A | 8/2000 | Moses et al. |
| 6,120,511 A | 9/2000 | Chan |
| 6,132,433 A | 10/2000 | Whelan |
| 6,143,017 A | 11/2000 | Thal |
| 6,156,039 A | 12/2000 | Thal |
| 6,183,479 B1 | 2/2001 | Toermaelae et al. |
| 6,267,766 B1 | 7/2001 | Burkhart |
| 6,290,711 B1 | 9/2001 | Caspari et al. |
| 6,302,886 B1 | 10/2001 | McDevitt et al. |
| 6,319,252 B1 | 11/2001 | McDevitt et al. |
| 6,319,269 B1 | 11/2001 | Li |
| 6,368,335 B1 | 4/2002 | Chan |
| 6,371,124 B1 | 4/2002 | Whelan |
| 6,387,129 B2 | 5/2002 | Rieser et al. |
| RE37,963 E | 1/2003 | Thal |
| 6,508,830 B2 | 1/2003 | Steiner |
| 6,511,487 B1 | 1/2003 | Oren et al. |
| 6,514,274 B1 | 2/2003 | Boucher et al. |
| 6,517,546 B2 | 2/2003 | Whittaker et al. |
| 6,520,980 B1 | 2/2003 | Foerster |
| 6,524,316 B1 | 2/2003 | Nicholson et al. |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,537,319 B2 | 3/2003 | Whelan |
| 6,540,750 B2 | 4/2003 | Burkhart |
| 6,544,281 B2 | 4/2003 | Elattrache et al. |
| 6,547,807 B2 | 4/2003 | Chan et al. |
| 6,585,730 B1 | 7/2003 | Foerster |
| 6,599,295 B1 | 7/2003 | Tornier et al. |
| 6,605,096 B1 | 8/2003 | Ritchart |
| 6,610,064 B1 | 8/2003 | Goble et al. |
| 6,616,674 B2 | 9/2003 | Schmieding |
| 6,623,524 B2 | 9/2003 | Schmieding |
| 6,629,984 B1 | 10/2003 | Chan |
| 6,638,283 B2 | 10/2003 | Thal |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,561 B1 | 11/2003 | Tran |
| 6,656,182 B1 | 12/2003 | Hayhurst |
| 6,656,183 B2 | 12/2003 | Colleran et al. |
| 6,660,023 B2 | 12/2003 | McDevitt et al. |
| 6,673,094 B1 | 1/2004 | McDevitt et al. |
| 6,692,516 B2 | 2/2004 | West et al. |
| 6,712,849 B2 | 3/2004 | Re et al. |
| 6,716,234 B2 | 4/2004 | Grafton et al. |
| 6,723,107 B1 | 4/2004 | Skiba et al. |
| 6,733,506 B1 | 5/2004 | McDevitt et al. |
| 6,733,529 B2 | 5/2004 | Whelan |
| 6,743,233 B1 | 6/2004 | Baldwin et al. |
| 6,770,073 B2 | 8/2004 | McDevitt et al. |
| 6,770,076 B2 | 8/2004 | Foerster |
| 6,770,084 B2 | 8/2004 | Bain et al. |
| 6,780,198 B1 | 8/2004 | Gregoire et al. |
| 6,830,572 B2 | 12/2004 | McDevitt et al. |
| 6,855,157 B2 | 2/2005 | Foerster et al. |
| 6,860,887 B1 | 3/2005 | Frankle |
| 6,878,166 B2 | 4/2005 | Clark et al. |
| 6,887,259 B2 | 5/2005 | Lizardi |
| 6,932,826 B2 | 8/2005 | Chan |
| 6,942,683 B2 | 9/2005 | Dunshee |
| 6,942,684 B2 | 9/2005 | Bonutti |
| 6,955,678 B2 | 10/2005 | Gabriel et al. |
| 6,958,067 B2 | 10/2005 | Whittaker et al. |
| 6,974,477 B2 | 12/2005 | Whelan |
| 6,984,237 B2 | 1/2006 | Hatch et al. |
| 6,986,781 B2 | 1/2006 | Smith |
| 6,991,636 B2 | 1/2006 | Rose |
| 6,994,719 B2 | 2/2006 | Grafton |
| 6,994,725 B1 | 2/2006 | Goble |
| 7,029,490 B2 | 4/2006 | Grafton et al. |
| 7,033,364 B1 | 4/2006 | Walters et al. |
| 7,037,324 B2 | 5/2006 | Martinek |
| 7,063,724 B2 | 6/2006 | Re et al. |
| 7,066,956 B2 | 6/2006 | Schmieding et al. |
| 7,074,203 B1 | 7/2006 | Johanson et al. |
| 7,077,863 B2 | 7/2006 | Schmieding et al. |
| 7,081,126 B2 | 7/2006 | McDevitt et al. |
| 7,083,638 B2 | 8/2006 | Foerster |
| 7,108,700 B2 | 9/2006 | Chan |
| 7,112,208 B2 | 9/2006 | Morris et al. |
| 7,147,651 B2 | 12/2006 | Morrison et al. |
| 7,172,595 B1 | 2/2007 | Goble |
| 7,175,632 B2 | 2/2007 | Singhatat et al. |
| 7,195,642 B2 | 3/2007 | McKernan et al. |
| 7,201,756 B2 | 4/2007 | Ross et al. |
| 7,226,469 B2 | 6/2007 | Benavitz et al. |
| 7,229,448 B2 | 6/2007 | Goble et al. |
| 7,235,100 B2 | 6/2007 | Martinek |
| 7,247,164 B1 | 7/2007 | Ritchart et al. |
| 7,285,124 B2 | 10/2007 | Foerster |
| 7,306,626 B2 | 12/2007 | Whelan |
| 7,309,337 B2 | 12/2007 | Colleran et al. |
| 7,309,346 B2 | 12/2007 | Martinek |
| 7,329,272 B2 | 2/2008 | Burkhart et al. |
| 7,341,592 B1 | 3/2008 | Walters et al. |
| D569,973 S | 5/2008 | Oren et al. |
| 7,377,926 B2 | 5/2008 | Topper et al. |
| 7,381,212 B2 | 6/2008 | Topper et al. |
| 7,381,213 B2 | 6/2008 | Lizardi |
| 7,399,302 B2 | 7/2008 | Goble et al. |
| D576,277 S | 9/2008 | Oren et al. |
| 7,458,975 B2 | 12/2008 | May et al. |
| 7,465,308 B2 | 12/2008 | Sikora et al. |
| 7,500,990 B2 | 3/2009 | Whelan |
| 7,517,357 B2 | 4/2009 | Abrams et al. |
| 7,527,648 B2 | 5/2009 | May et al. |
| 7,530,999 B2 | 5/2009 | Clark et al. |
| 7,556,640 B2 | 7/2009 | Foerster |
| 7,569,059 B2 | 8/2009 | Cerundolo |
| 7,585,305 B2 | 9/2009 | Dreyfuss |
| 7,585,311 B2 | 9/2009 | Green et al. |
| 7,588,587 B2 | 9/2009 | Barbieri et al. |
| 7,588,595 B2 | 9/2009 | Miller et al. |
| 7,594,917 B2 | 9/2009 | Whittaker et al. |
| 7,608,084 B2 | 10/2009 | Oren et al. |
| 7,625,386 B2 | 12/2009 | Abe et al. |
| 7,637,926 B2 | 12/2009 | Foerster et al. |
| 7,651,495 B2 | 1/2010 | McDevitt et al. |
| 7,655,011 B2 | 2/2010 | Whittaker et al. |
| 7,662,171 B2 | 2/2010 | West et al. |
| 7,674,275 B2 | 3/2010 | Martin et al. |
| 7,674,290 B2 | 3/2010 | McKernan et al. |
| 7,678,134 B2 | 3/2010 | Schmieding et al. |
| 7,682,374 B2 | 3/2010 | Foerster et al. |
| 7,695,494 B2 | 4/2010 | Foerster |
| 7,713,286 B2 | 5/2010 | Singhatat |
| 7,713,300 B2 | 5/2010 | Meridew et al. |
| 7,749,237 B2 | 7/2010 | Chan |
| 7,771,441 B2 | 8/2010 | Cerundolo |
| 7,803,173 B2 | 9/2010 | Burkhart et al. |
| 7,819,898 B2 | 10/2010 | Stone et al. |
| 7,833,230 B2 | 11/2010 | Cerundolo |
| 7,833,244 B2 | 11/2010 | Cerundolo |
| 7,837,710 B2 | 11/2010 | Lombardo et al. |
| 7,837,718 B2 | 11/2010 | Clark et al. |
| 7,842,050 B2 | 11/2010 | Diduch et al. |
| 7,867,251 B2 | 1/2011 | Colleran et al. |
| 7,867,264 B2 | 1/2011 | McDevitt et al. |

(56) References Cited

U.S. PATENT DOCUMENTS

| | | |
|---|---|---|
| 7,868,251 B2 | 1/2011 | Gladd et al. |
| 7,879,046 B2 | 2/2011 | Weinert et al. |
| 7,879,048 B2 | 2/2011 | Bain et al. |
| 7,883,519 B2 | 2/2011 | Oren et al. |
| 7,892,256 B2 | 2/2011 | Grafton et al. |
| 7,896,907 B2 | 3/2011 | McDevitt et al. |
| 7,896,917 B2 | 3/2011 | Walters et al. |
| 7,905,903 B2 | 3/2011 | Stone et al. |
| 7,931,657 B2 | 4/2011 | Walters et al. |
| 7,938,847 B2 | 5/2011 | Fanton et al. |
| 7,942,878 B2 | 5/2011 | Fernandez |
| 7,942,914 B2 | 5/2011 | Cerundolo |
| 7,955,341 B2 | 6/2011 | Cerundolo |
| 7,959,649 B2 | 6/2011 | Burkhart |
| 7,959,650 B2 | 6/2011 | Kaiser et al. |
| 7,963,972 B2 | 6/2011 | Foerster et al. |
| 7,963,983 B2 | 6/2011 | Cerundolo |
| RE42,526 E | 7/2011 | Reiser et al. |
| 7,976,565 B1 | 7/2011 | Meridew |
| 7,981,140 B2 | 7/2011 | Burkhart |
| 7,988,697 B2 | 8/2011 | Miller et al. |
| 7,993,369 B2 | 8/2011 | Dreyfuss et al. |
| 8,012,171 B2 | 9/2011 | Schmieding |
| 8,012,172 B2 | 9/2011 | Grafton et al. |
| 8,012,174 B2 | 9/2011 | Elattrache et al. |
| 8,029,537 B2 | 10/2011 | West et al. |
| 8,038,652 B2 | 10/2011 | Morrison et al. |
| 8,043,308 B2 | 10/2011 | Bittenson |
| 8,062,295 B2 | 11/2011 | McDevitt et al. |
| 8,080,013 B2 | 12/2011 | Whittaker et al. |
| 8,083,769 B2 | 12/2011 | Cauldwell et al. |
| 8,088,146 B2 | 1/2012 | Wert et al. |
| 8,100,942 B1 | 1/2012 | Green et al. |
| 8,105,343 B2 | 1/2012 | White et al. |
| 8,109,966 B2 | 2/2012 | Ritchart et al. |
| 8,109,969 B1 | 2/2012 | Green et al. |
| 8,114,128 B2 | 2/2012 | Cauldwell et al. |
| 8,118,835 B2 | 2/2012 | Weisel et al. |
| 8,128,634 B2 | 3/2012 | Whittaker et al. |
| 8,133,258 B2 | 3/2012 | Foerster et al. |
| 8,137,360 B2 | 3/2012 | Whittaker et al. |
| 8,137,381 B2 | 3/2012 | Foerster et al. |
| 8,137,383 B2 | 3/2012 | West et al. |
| 8,147,505 B2 | 4/2012 | Delli-Santi |
| 8,162,978 B2 | 4/2012 | Lombardo et al. |
| 8,167,906 B2 | 5/2012 | Cauldwell et al. |
| 8,177,796 B2 | 5/2012 | Akyuz et al. |
| 8,202,295 B2 | 6/2012 | Kaplan |
| 8,202,296 B2 | 6/2012 | Burkhart |
| 8,202,297 B2 | 6/2012 | Burkhart |
| 8,226,716 B2 | 7/2012 | McKernan et al. |
| 8,231,653 B2 | 7/2012 | Dreyfuss |
| 8,262,675 B2 | 9/2012 | Cropper et al. |
| 8,267,964 B2 | 9/2012 | Green et al. |
| 8,277,451 B2 | 10/2012 | Fernandez |
| 8,277,458 B2 | 10/2012 | Schneider |
| 8,277,464 B2 | 10/2012 | Bittenson |
| 8,277,484 B2 | 10/2012 | Barbieri et al. |
| 8,282,643 B2 | 10/2012 | Dross |
| 8,282,659 B2 | 10/2012 | Oren et al. |
| 8,298,262 B2 | 10/2012 | Stone et al. |
| 8,317,829 B2 | 11/2012 | Foerster et al. |
| 8,317,862 B2 | 11/2012 | Troger et al. |
| 8,328,843 B2 | 12/2012 | Oren et al. |
| 8,348,975 B2 | 1/2013 | Dreyfuss |
| 8,361,079 B2 | 1/2013 | Pandya |
| 8,372,124 B2 | 2/2013 | Paulk et al. |
| 8,382,835 B2 | 2/2013 | Meridew et al. |
| 8,383,188 B2 | 2/2013 | Mazzocca et al. |
| 8,388,654 B2 | 3/2013 | Snyder et al. |
| 8,394,112 B2 | 3/2013 | Nason |
| 8,394,123 B2 | 3/2013 | Cauldwell et al. |
| 8,409,204 B2 | 4/2013 | Martin et al. |
| 8,409,225 B2 | 4/2013 | Bull et al. |
| 8,419,794 B2 | 4/2013 | Elattrache et al. |
| 8,425,536 B2 | 4/2013 | Foerster et al. |
| 8,430,909 B2 | 4/2013 | Dreyfuss et al. |
| 8,435,264 B2 | 5/2013 | Sojka et al. |
| 8,444,672 B2 | 5/2013 | Foerster |
| 8,444,674 B2 | 5/2013 | Kaplan |
| 8,449,552 B2 | 5/2013 | Sanders |
| 8,454,654 B2 | 6/2013 | Ferragamo et al. |
| 8,460,340 B2 | 6/2013 | Sojka et al. |
| 8,465,521 B2 | 6/2013 | Cook et al. |
| 8,465,522 B2 | 6/2013 | Burkhart |
| 8,469,998 B2 | 6/2013 | Sojka et al. |
| 8,475,436 B1 | 7/2013 | Jordan |
| 8,491,595 B2 | 7/2013 | Volpi et al. |
| 8,491,600 B2 | 7/2013 | McDevitt et al. |
| 8,506,596 B2 | 8/2013 | Stone et al. |
| 8,512,378 B2 | 8/2013 | Green et al. |
| 8,518,091 B2 | 8/2013 | McDevitt et al. |
| 8,523,902 B2 | 9/2013 | Heaven et al. |
| 8,529,577 B2 | 9/2013 | Hirt et al. |
| 8,529,601 B2 | 9/2013 | Green et al. |
| 8,535,350 B2 | 9/2013 | Lizardi et al. |
| 8,540,732 B2 | 9/2013 | Weinert et al. |
| 8,540,737 B2 | 9/2013 | Chudik |
| 8,551,123 B2 | 10/2013 | Pandya |
| 8,556,911 B2 | 10/2013 | Mehta et al. |
| 8,579,974 B2 | 11/2013 | Pandya |
| 8,591,580 B2 | 11/2013 | McKernan et al. |
| 8,597,328 B2 | 12/2013 | Cauldwell et al. |
| 8,613,756 B2 | 12/2013 | Lizardi et al. |
| 8,617,186 B2 | 12/2013 | White et al. |
| 8,617,219 B2 | 12/2013 | Oren et al. |
| 8,623,032 B2 | 1/2014 | Diduch et al. |
| 8,652,171 B2 | 2/2014 | Stone et al. |
| 8,657,854 B2 | 2/2014 | Foerster et al. |
| 8,663,279 B2 | 3/2014 | Burkhart et al. |
| 8,663,280 B2 | 3/2014 | Kaplan |
| 8,672,954 B2 | 3/2014 | Oren et al. |
| 8,672,966 B2 | 3/2014 | Wert et al. |
| 8,672,967 B2 | 3/2014 | Dimatteo et al. |
| 8,672,970 B2 | 3/2014 | Ferragamo et al. |
| 8,685,060 B2 | 4/2014 | Foerster |
| 8,690,915 B2 | 4/2014 | Hootstein |
| 8,696,688 B2 | 4/2014 | Stone |
| 8,702,752 B2 | 4/2014 | Schmieding et al. |
| 8,702,754 B2 | 4/2014 | Dimatteo et al. |
| 8,709,040 B2 | 4/2014 | Anderhub et al. |
| 8,709,395 B2 | 4/2014 | Boutros |
| 8,721,650 B2 | 5/2014 | Fanton et al. |
| 8,740,913 B2 | 6/2014 | Schneider |
| 8,747,469 B2 | 6/2014 | Wang et al. |
| 8,764,798 B2 | 7/2014 | Housman |
| 8,771,315 B2 | 7/2014 | Lunn et al. |
| 8,771,351 B2 | 7/2014 | Elattrache et al. |
| 8,777,990 B2 | 7/2014 | Van et al. |
| 8,784,449 B2 | 7/2014 | Snyder et al. |
| 8,784,489 B2 | 7/2014 | Walters et al. |
| 8,790,370 B2 | 7/2014 | Spenciner et al. |
| 8,808,326 B2 | 8/2014 | Gagliano |
| 8,814,905 B2 | 8/2014 | Sengun et al. |
| 8,828,029 B2 | 9/2014 | White et al. |
| 8,834,495 B2 | 9/2014 | White et al. |
| 8,834,521 B2 | 9/2014 | Pinto et al. |
| 8,834,543 B2 | 9/2014 | McDevitt et al. |
| 8,858,560 B2 | 10/2014 | Bradley et al. |
| 8,870,877 B2 | 10/2014 | Koogle, Jr. |
| 8,881,635 B2 | 11/2014 | Martin |
| 8,882,801 B2 | 11/2014 | Dimatteo et al. |
| 8,906,060 B2 | 12/2014 | Hart |
| 8,926,663 B2 | 1/2015 | Green et al. |
| 8,936,620 B2 | 1/2015 | Kaiser et al. |
| 8,943,941 B2 | 2/2015 | Dow et al. |
| 8,951,292 B2 | 2/2015 | Paulk et al. |
| 8,961,576 B2 | 2/2015 | Hodge et al. |
| 8,986,345 B2 | 3/2015 | Denham et al. |
| 8,986,346 B2 | 3/2015 | Dreyfuss |
| 8,986,347 B2 | 3/2015 | Housman |
| 8,992,573 B2 | 3/2015 | Van et al. |
| 9,005,246 B2 | 4/2015 | Burkhart et al. |
| 9,017,381 B2 | 4/2015 | Kaiser et al. |

(56) References Cited

U.S. PATENT DOCUMENTS

| | | |
|---|---|---|
| 9,023,083 B2 | 5/2015 | Foerster et al. |
| 9,034,014 B2 | 5/2015 | Catania et al. |
| 9,044,222 B2 | 6/2015 | Dross |
| 9,044,226 B2 | 6/2015 | Green et al. |
| 9,107,653 B2 | 8/2015 | Sullivan |
| 9,113,859 B2 | 8/2015 | Dooney et al. |
| 9,144,425 B2 | 9/2015 | Kaplan |
| 9,149,268 B2 | 10/2015 | Graul et al. |
| 9,155,542 B2 | 10/2015 | Markarian |
| 9,161,750 B2 | 10/2015 | Zirps et al. |
| 9,179,907 B2 | 11/2015 | Elattrache et al. |
| 9,198,649 B2 | 12/2015 | Karapetian et al. |
| 9,226,742 B2 | 1/2016 | Wolf et al. |
| 9,265,496 B2 | 2/2016 | Sojka et al. |
| 9,307,979 B1 | 4/2016 | Bennett et al. |
| 9,445,805 B2 | 9/2016 | Snell et al. |
| 9,498,232 B2 | 11/2016 | Perez, III |
| 9,782,165 B2 | 10/2017 | Murphy et al. |
| 10,154,868 B2 | 12/2018 | Fallin et al. |
| 10,219,813 B2 | 3/2019 | Okuno et al. |
| 10,258,401 B2 | 4/2019 | Fallin et al. |
| 10,426,460 B2 | 10/2019 | Taber et al. |
| 2001/0016747 A1 | 8/2001 | Romano et al. |
| 2002/0029066 A1 | 3/2002 | Foerster |
| 2002/0065526 A1 | 5/2002 | Oren et al. |
| 2003/0105524 A1 | 6/2003 | Paulos et al. |
| 2003/0171778 A1 | 9/2003 | Lizardi |
| 2003/0195528 A1 | 10/2003 | Ritchart |
| 2003/0195563 A1 | 10/2003 | Foerster |
| 2003/0229362 A1 | 12/2003 | Chan et al. |
| 2004/0010286 A1 | 1/2004 | Gieringer |
| 2004/0082956 A1 | 4/2004 | Baldwin et al. |
| 2004/0088004 A1 | 5/2004 | Rosch |
| 2004/0098051 A1 | 5/2004 | Fallin et al. |
| 2004/0098053 A1 | 5/2004 | Tran |
| 2004/0116843 A1 | 6/2004 | Chan |
| 2004/0172062 A1 | 9/2004 | Burkhart |
| 2004/0267317 A1 | 12/2004 | Higgins et al. |
| 2005/0033362 A1 | 2/2005 | Grafton |
| 2005/0033364 A1 | 2/2005 | Gregoire et al. |
| 2005/0149122 A1 | 7/2005 | McDevitt et al. |
| 2005/0245932 A1 | 11/2005 | Fanton et al. |
| 2005/0277986 A1 | 12/2005 | Foerster et al. |
| 2006/0074438 A1 | 4/2006 | Chan |
| 2006/0079904 A1 | 4/2006 | Thal |
| 2006/0142784 A1 | 6/2006 | Kontos |
| 2006/0149258 A1 | 7/2006 | Sousa |
| 2006/0155328 A1 | 7/2006 | Foerster |
| 2006/0235413 A1* | 10/2006 | Denham ............ A61B 17/0401 606/907 |
| 2006/0241658 A1 | 10/2006 | Cerundolo |
| 2006/0247641 A1 | 11/2006 | Re et al. |
| 2006/0271060 A1 | 11/2006 | Gordon |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2006/0293691 A1 | 12/2006 | Mitra et al. |
| 2007/0005067 A1 | 1/2007 | Dross |
| 2007/0005068 A1 | 1/2007 | Sklar |
| 2007/0016251 A1 | 1/2007 | Roby |
| 2007/0021751 A1 | 1/2007 | Reay-Young et al. |
| 2007/0027475 A1 | 2/2007 | Pagedas |
| 2007/0088362 A1 | 4/2007 | Bonutti et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0167950 A1 | 7/2007 | Tauro et al. |
| 2007/0173845 A1 | 7/2007 | Kim |
| 2007/0203498 A1 | 8/2007 | Gerber et al. |
| 2007/0213730 A1 | 9/2007 | Martinek et al. |
| 2007/0213770 A1 | 9/2007 | Dreyfuss |
| 2007/0219557 A1 | 9/2007 | Bourque et al. |
| 2007/0219558 A1 | 9/2007 | Deutsch |
| 2007/0288023 A1 | 12/2007 | Pellegrino et al. |
| 2008/0009904 A1 | 1/2008 | Bourque et al. |
| 2008/0033460 A1* | 2/2008 | Ziniti ............ A61B 17/0401 606/148 |
| 2008/0033486 A1 | 2/2008 | Whittaker et al. |
| 2008/0057838 A1 | 3/2008 | Huang et al. |
| 2008/0077161 A1 | 3/2008 | Kaplan |
| 2008/0103528 A1 | 5/2008 | Zirps et al. |
| 2008/0125815 A1 | 5/2008 | Heaven et al. |
| 2008/0188936 A1 | 8/2008 | Ball et al. |
| 2008/0208253 A1 | 8/2008 | Dreyfuss et al. |
| 2008/0234730 A1 | 9/2008 | Cotton et al. |
| 2008/0243174 A1 | 10/2008 | Oren et al. |
| 2008/0243177 A1 | 10/2008 | Oren et al. |
| 2008/0243178 A1 | 10/2008 | Oren et al. |
| 2008/0275453 A1 | 11/2008 | Lafosse et al. |
| 2008/0287992 A1 | 11/2008 | Tornier et al. |
| 2008/0300629 A1 | 12/2008 | Surti |
| 2009/0018561 A1 | 1/2009 | Schwartz et al. |
| 2009/0018581 A1 | 1/2009 | Anderson et al. |
| 2009/0036905 A1 | 2/2009 | Schmieding |
| 2009/0048623 A1 | 2/2009 | Lafosse et al. |
| 2009/0062819 A1 | 3/2009 | Burkhart et al. |
| 2009/0099598 A1 | 4/2009 | McDevitt et al. |
| 2009/0138002 A1 | 5/2009 | Fenton |
| 2009/0149884 A1 | 6/2009 | Snyder et al. |
| 2009/0171360 A1 | 7/2009 | Whelan |
| 2009/0187216 A1 | 7/2009 | Schmieding et al. |
| 2009/0192546 A1 | 7/2009 | Schmieding et al. |
| 2009/0222039 A1 | 9/2009 | Dreyfuss et al. |
| 2009/0287246 A1 | 11/2009 | Cauldwell et al. |
| 2009/0292313 A1 | 11/2009 | Anspach et al. |
| 2009/0312782 A1 | 12/2009 | Park |
| 2009/0312794 A1 | 12/2009 | Nason et al. |
| 2009/0318960 A1 | 12/2009 | Burkhart |
| 2010/0004683 A1 | 1/2010 | Hoof et al. |
| 2010/0087872 A1 | 4/2010 | Morihara et al. |
| 2010/0100129 A1 | 4/2010 | West et al. |
| 2010/0106194 A1 | 4/2010 | Bonutti et al. |
| 2010/0121337 A1 | 5/2010 | Pandya |
| 2010/0121348 A1 | 5/2010 | Van et al. |
| 2010/0121375 A1 | 5/2010 | Pandya |
| 2010/0137889 A1 | 6/2010 | Oren et al. |
| 2010/0179573 A1 | 7/2010 | Levinsohn et al. |
| 2010/0198235 A1 | 8/2010 | Pierce et al. |
| 2010/0249835 A1 | 9/2010 | Schwartz et al. |
| 2010/0262184 A1 | 10/2010 | Dreyfuss |
| 2010/0292732 A1 | 11/2010 | Hirotsuka et al. |
| 2010/0318125 A1 | 12/2010 | Gerber et al. |
| 2010/0318139 A1 | 12/2010 | Beauchamp |
| 2010/0324575 A1 | 12/2010 | Chan |
| 2011/0009867 A1 | 1/2011 | Oren et al. |
| 2011/0009884 A1 | 1/2011 | Kaplan |
| 2011/0022087 A1 | 1/2011 | Cerundolo |
| 2011/0028997 A1 | 2/2011 | Gregoire et al. |
| 2011/0071550 A1 | 3/2011 | Diduch et al. |
| 2011/0106013 A1 | 5/2011 | Whittaker et al. |
| 2011/0106124 A1 | 5/2011 | Beauchamp |
| 2011/0112550 A1 | 5/2011 | Heaven et al. |
| 2011/0112576 A1 | 5/2011 | Nguyen et al. |
| 2011/0118757 A1 | 5/2011 | Pierce |
| 2011/0152928 A1 | 6/2011 | Colleran et al. |
| 2011/0190815 A1 | 8/2011 | Saliman |
| 2011/0208198 A1 | 8/2011 | Anderson et al. |
| 2011/0224726 A1 | 9/2011 | Lombardo et al. |
| 2011/0238111 A1 | 9/2011 | Frank |
| 2011/0238112 A1 | 9/2011 | Kim et al. |
| 2011/0238113 A1 | 9/2011 | Fanton et al. |
| 2011/0245869 A1 | 10/2011 | Burkhart |
| 2011/0295279 A1 | 12/2011 | Stone et al. |
| 2011/0301622 A1 | 12/2011 | Oren et al. |
| 2012/0041484 A1 | 2/2012 | Briganti et al. |
| 2012/0059415 A1 | 3/2012 | Sklar |
| 2012/0116451 A1 | 5/2012 | Tepic |
| 2012/0143224 A1 | 6/2012 | Chan |
| 2012/0150225 A1 | 6/2012 | Burkhart et al. |
| 2012/0150235 A1 | 6/2012 | Snyder et al. |
| 2012/0158051 A1 | 6/2012 | Foerster |
| 2012/0165868 A1 | 6/2012 | Burkhart et al. |
| 2012/0179200 A1 | 7/2012 | Cauldwell et al. |
| 2012/0197296 A1 | 8/2012 | Mayer et al. |

(56) References Cited

U.S. PATENT DOCUMENTS

| | | |
|---|---|---|
| 2012/0209279 A1 | 8/2012 | Snyder et al. |
| 2012/0209325 A1 | 8/2012 | Gagliano et al. |
| 2012/0245634 A1 | 9/2012 | Kaplan |
| 2012/0265219 A1 | 10/2012 | Rushdy et al. |
| 2012/0272816 A1 | 11/2012 | Ueda et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035720 A1 | 2/2013 | Perriello et al. |
| 2013/0053959 A1 | 2/2013 | Lizardi et al. |
| 2013/0060280 A1 | 3/2013 | Wolf et al. |
| 2013/0103083 A1 | 4/2013 | Baird |
| 2013/0123809 A1 | 5/2013 | Murphy et al. |
| 2013/0123842 A1 | 5/2013 | Chan et al. |
| 2013/0123843 A1 | 5/2013 | Chan et al. |
| 2013/0144335 A1 | 6/2013 | Sandow |
| 2013/0150885 A1 | 6/2013 | Dreyfuss |
| 2013/0165972 A1 | 6/2013 | Sullivan |
| 2013/0178854 A1 | 7/2013 | Sholev et al. |
| 2013/0190782 A1 | 7/2013 | Nason |
| 2013/0197578 A1 | 8/2013 | Gregoire et al. |
| 2013/0204253 A1 | 8/2013 | Oren et al. |
| 2013/0204299 A1 | 8/2013 | Mantovani et al. |
| 2013/0211429 A1 | 8/2013 | Snyder et al. |
| 2013/0218273 A1 | 8/2013 | Bull et al. |
| 2013/0226231 A1 | 8/2013 | Weinert et al. |
| 2013/0267998 A1 | 10/2013 | Vijay et al. |
| 2013/0296936 A1 | 11/2013 | Burkhart |
| 2013/0325011 A1 | 12/2013 | Cleveland et al. |
| 2013/0338710 A1 | 12/2013 | Heaven et al. |
| 2013/0345711 A1 | 12/2013 | Mehta et al. |
| 2013/0345749 A1 | 12/2013 | Sullivan et al. |
| 2013/0345750 A1 | 12/2013 | Sullivan |
| 2014/0046369 A1 | 2/2014 | Heaven et al. |
| 2014/0046443 A1 | 2/2014 | McKernan et al. |
| 2014/0081320 A1 | 3/2014 | Sengun et al. |
| 2014/0107672 A1 | 4/2014 | Dross |
| 2014/0107700 A1 | 4/2014 | Baird et al. |
| 2014/0114317 A1 | 4/2014 | Oren et al. |
| 2014/0114411 A1 | 4/2014 | Baird et al. |
| 2014/0121467 A1 | 5/2014 | Vayser et al. |
| 2014/0134802 A1 | 5/2014 | Lin et al. |
| 2014/0135802 A1 | 5/2014 | Mantovani |
| 2014/0163612 A1 | 6/2014 | Hootstein |
| 2014/0171948 A1 | 6/2014 | Griffiths et al. |
| 2014/0172016 A1 | 6/2014 | Housman |
| 2014/0186416 A1 | 7/2014 | Boutros |
| 2014/0186418 A1 | 7/2014 | Boutros |
| 2014/0194906 A1 | 7/2014 | Topper et al. |
| 2014/0207189 A1 | 7/2014 | Foerster et al. |
| 2014/0214038 A1 | 7/2014 | Sholev et al. |
| 2014/0222072 A1 | 8/2014 | Gerber et al. |
| 2014/0243892 A1 | 8/2014 | Choinski |
| 2014/0257384 A1 | 9/2014 | Dreyfuss et al. |
| 2014/0276984 A1 | 9/2014 | Burbank et al. |
| 2014/0277129 A1* | 9/2014 | Arai .................. A61B 17/0401 606/232 |
| 2014/0288594 A1 | 9/2014 | Shaefers et al. |
| 2014/0303625 A1 | 10/2014 | Sholev et al. |
| 2014/0324100 A1 | 10/2014 | Burkhart |
| 2014/0343605 A1 | 11/2014 | Lunn et al. |
| 2014/0364876 A1 | 12/2014 | White et al. |
| 2014/0364905 A1 | 12/2014 | Lunn et al. |
| 2014/0364907 A1 | 12/2014 | White et al. |
| 2014/0379027 A1 | 12/2014 | Dreyfuss et al. |
| 2014/0379028 A1 | 12/2014 | Lo |
| 2015/0005773 A1 | 1/2015 | Oren et al. |
| 2015/0005817 A1 | 1/2015 | Snyder et al. |
| 2015/0005818 A1 | 1/2015 | McDevitt et al. |
| 2015/0025552 A1 | 1/2015 | Stoll |
| 2015/0032155 A1 | 1/2015 | Dreyfuss et al. |
| 2015/0032157 A1 | 1/2015 | Dooney et al. |
| 2015/0045795 A1 | 2/2015 | Sholev et al. |
| 2015/0051645 A1 | 2/2015 | Green et al. |
| 2015/0066079 A1 | 3/2015 | Schmieding |
| 2015/0066080 A1 | 3/2015 | Olson et al. |
| 2015/0066081 A1 | 3/2015 | Martin |
| 2015/0088196 A1 | 3/2015 | Kaplan |
| 2015/0119937 A1 | 4/2015 | Lunn et al. |
| 2015/0141998 A1 | 5/2015 | Kiapour et al. |
| 2015/0150551 A1 | 6/2015 | Paulk et al. |
| 2015/0157312 A1 | 6/2015 | Burkhart et al. |
| 2015/0196388 A1 | 7/2015 | Housman et al. |
| 2015/0216522 A1 | 8/2015 | Ticker |
| 2015/0216542 A1 | 8/2015 | Libby et al. |
| 2015/0223926 A1 | 8/2015 | Foerster et al. |
| 2015/0245831 A1 | 9/2015 | Sullivan |
| 2015/0297211 A1 | 10/2015 | Sullivan et al. |
| 2015/0297274 A1 | 10/2015 | Dreyfuss et al. |
| 2015/0313586 A1 | 11/2015 | Burkhart et al. |
| 2015/0327849 A1 | 11/2015 | Dooney et al. |
| 2015/0335327 A1 | 11/2015 | Ferguson et al. |
| 2015/0351752 A1 | 12/2015 | Rousseau et al. |
| 2015/0359533 A1 | 12/2015 | Kaplan |
| 2016/0015380 A1 | 1/2016 | Sholev et al. |
| 2016/0296224 A1 | 10/2016 | Snell et al. |
| 2016/0338689 A1 | 11/2016 | Baird |
| 2016/0338693 A1 | 11/2016 | Graul et al. |
| 2017/0042533 A1 | 2/2017 | Lunn et al. |
| 2017/0065273 A1 | 3/2017 | Hart et al. |
| 2017/0100182 A1 | 4/2017 | Shah et al. |
| 2018/0078251 A1 | 3/2018 | Copple et al. |
| 2019/0167251 A1 | 6/2019 | Fallin et al. |
| 2021/0177394 A1 | 6/2021 | Rippe et al. |

FOREIGN PATENT DOCUMENTS

| | | |
|---|---|---|
| WO | 03/65904 A1 | 8/2003 |
| WO | 2004/049958 A1 | 6/2004 |
| WO | 2009/018565 A1 | 2/2009 |
| WO | 2009/042951 A1 | 4/2009 |
| WO | 2009/055800 A1 | 4/2009 |
| WO | 2009/076526 A1 | 6/2009 |
| WO | 2010/005749 A1 | 1/2010 |
| WO | 2010/009217 A1 | 1/2010 |
| WO | 2010/056786 A2 | 5/2010 |
| WO | 2010/056787 A2 | 5/2010 |
| WO | 2011/056701 A1 | 5/2011 |
| WO | 2011/059995 A2 | 5/2011 |
| WO | 2011/060022 A2 | 5/2011 |
| WO | 2011/060437 A1 | 5/2011 |
| WO | 2011/133233 A1 | 10/2011 |
| WO | 2012/024446 A2 | 2/2012 |
| WO | 2012/052891 A1 | 4/2012 |
| WO | 2012/129388 A1 | 9/2012 |
| WO | 2013/014553 A1 | 1/2013 |
| WO | 2013/027210 A1 | 2/2013 |
| WO | 2013/052128 A1 | 4/2013 |
| WO | 2013/112449 A1 | 8/2013 |
| WO | 2013/151817 A1 | 10/2013 |
| WO | 2013/181212 A1 | 12/2013 |
| WO | 2014/018946 A1 | 1/2014 |
| WO | 2014/051930 A2 | 4/2014 |
| WO | 2014/055678 A1 | 4/2014 |
| WO | 2014/059378 A1 | 4/2014 |
| WO | 2014/066116 A1 | 5/2014 |
| WO | 2014/071052 A1 | 5/2014 |
| WO | 2014/071066 A1 | 5/2014 |
| WO | 2015/005951 A1 | 1/2015 |
| WO | 2015/008176 A2 | 1/2015 |
| WO | 2015/017426 A1 | 2/2015 |
| WO | 2015/031559 A1 | 3/2015 |
| WO | 2016/148941 A1 | 9/2016 |

OTHER PUBLICATIONS

Achilles SpeedBridge Surgical Technique, Arthrex, Inc., www.arthrex.com, 2013, 6 pp.

Achilles SutureBridge Surgical Technique, Arthrex, Inc., www.arthrex.com, 2014, 6 pp.

ALLThread Knotless Suture Anchor, Double Row Rotator Cuff Repair, Biomet Orthopedics, www.biomet.com, 2012, 12 pp.

(56) References Cited

OTHER PUBLICATIONS

Arthrex is Reaching New Heights in Rotator Cuff Repair, Arthrex, Inc., www.arthrex.com, 2007, 8 pp.
Arthrex SpeedBridge and Tornier Arthro Tunneler Biomechanical Cadavar Testing, Arthrex, Inc., 2010, 2 pp.
Arthroscopic and Mini-Open Rotator Cuff Repair Using JuggerKnot Soft Anchor—2.9 mm with ALLthread Knotless Anchor Surgical Technique, Biomet Sports Medicine, www.biomet.com, 2013, 16 pp.
Arthroscopic Shoulder Repair Using the Smith & Nephew Footpring PK Suture Anchor, Smith & Nephew, Inc., www.smith-nephew.com, 2008, 12 pp.
ArthroTunneler TunnelPro System, Transosseous Rotator Cuff Repair, Tornier, Inc., www.tornier.com, 2012, 6 pp.
Biceps Tenodesis SwiveLock System Surgical Technique, Arthrex, Inc., www.arthrex.com, 2012, 6 pp.
BioRaptor Knotless Suture Anchor, Smith & Nephew, Inc., www.smith-nephew.com, 2010, 6 pp.
Carter, Sally L., et al, "Suture Performance in Standard Arthroscopic Knots-Effects of Material and Design" Smith & Nephew, Inc., www.smith-nephew.com, 2004, 4 pp.
Chu, T., et al., "Biomechanical Evaluation of Knotless Fixation Systems for Rotator Cuff Repairs", 56th Annual Meeting of the Orthopaedic Research Society, Post No. 1791, 1 pp.
Cinch Lock SS (Sports Sheath) Knotless Labrum Restoration, Stryker Corporation, www.stryker.com, 6 pp, accessed online on Jun. 22, 2022.
Comprehensive Product Offerings for your Rotator Cuff Repair, Smith & Nephew, Inc., www smith-nephew.com, 2015, 12 pp.
DeFranco, Michael J., et al., "Arthroscopic Rotator Cuff Repair Failure Resulting from Decorticiation of the Rotator Cuff Footprint: A Case Report", The American Journal of Orthopedics, Dec. 2009, pp. 32-33.
Double Row Rotator Cuff Repair using the Bio-Corkscrew Ft Surgical Technique, Arthrex, Inc., www.arthrex.com, 2007, 6 pp.
Dr. S. D. Gerber Double Row Method Surgical Technique, Stryker Corporation, www.stryker.com, 2010, 12 pp.
Efird, Chad, et al., "Knotless Single-Row Rotator Cuff Repair: A Comparative Biomechanical Study of 2 Knotless Suture Anchors", Healio.com/Orthopedics, Aug. 2013, 5 pp.
Flores, Steve, "Comparison of the Pull-Back Effect of Rotator Cuff Anchors", Arthrex, Inc., 2007, 2 pp.
Halbrecht, Jeffrey, "Versalok A New Technique for Arthroscopic Knotless Rotator Cuff Repair", 44 pp, accessed online on Jun. 22, 2022.
Introducing tie Healix Advance Family of Suture Anchors, DePuy Mitek, Inc, 2012, 4 pp.
Knotless SutureTak Instability Repair Surgical Technique, Arthrex, Inc., www.arthex.com, 2017, 6 pp.
Knotless SutureTak Instability Repair Surgical Technique, Arthrex, Inc., www.arthrex.com, 2015, 6 pp.
Mall, Nathan A., et al., "Transosseous-Equivalent Rotator Cuff Repair: A Systematic Review on the Biomechanical Importance of Tying the Medial Row", Arthroscopy: The Journal of Arthroscopic and Related Surgery, vol. 29, No. 2, Feb. 2013, pp. 377-386.
Massive Rotator Cuff Repair and Augmentation using the SpeedBridge and ArthroFlex Dermal Matrix Surgical Technique, Arthrex, Inc., www.arthrex.com, 2012, 4 pp.
Multifix's PEEK 5.5mm and 6.5mm Knotless Implants Technique Guide, ArthroCare Corporation, www.smith-nephew.com, 2015, 8 pp.
Nho, Shane J., et al.,. "Bioabsorbable Anchors in Glenohumeral Shoulder Surgery", Arthrscopy: The Journal of Arthroscopic and Related Surgery, vol. 25, No. 7, Jul. 2009, pp. 788-793.
Opus AutoCuff Magnum X Knotless Fixation Implant with Independent Tensioning, ArthroCare Sports Medicine, www.arthrocaresportsmedicine.com, 2009, 2 pp.
Pull-Out Strength Comparison of Arthrex to Mitek Suture Anchors, Arthrex Research and Development, Arthrex, Inc., 2010, 1 pp.
Quattro Shoulder System—Innovative Rotator Cuff Solutions, https://www.zimmerbiomet.com/en/products-and-solutions/specialties/sports-medicine/quattro-x-suture-anchors.html#04-Info, 12 pp, accessed online Jun. 22, 2022.
Quattro Shoulder System—Innovative Rotator Cuff Solutions, Cayenne Medical, Inc., www.cayennemedical.com, 6 pp.
Quickdraw Knotless Suture Anchor System Surgical Technique, Writght Medical Technology, Inc. www.wmt.com, 2011, 28 pp.
ReelX STT Knotless Anchor System, Stryker Corporation, www.stryker.com, 2010, 4 pp.
Revolutionizing Orthopedic Surgery, FiberWire Braided Composite Suture, Arthrex, Inc., www.arthrex.com, 2012, 8 pp.
Shoulder Restoration System, ConMed Linvatec, wwww.linvatec.com, 2014, 20 pp.
Shoulder Restoration System, PopLok Knotless Suture Anchor, ConMed Linvatec, www.linvatec.com, 8 pp, 2013.
SpeedBridge and SpeedFix Knotless Rotator Cuff Repair using the SwiveLock C and FiberTape Surgical Technique, Arthrex, Inc., www.arthrex.com, 2013, 8 pp.
Supplementary European Search Report dated Jun. 26, 2019 for corresponding European Application No. EP16833705.
Surgical Technique Sharc-FT and Taylor Stitcher Transosseus Devices for Fast Rotator Cuff Repair, NCS Lab Medical Devices Factory, 14 pp., accessed online Jun. 22, 2022, https://ncs-company.com/en/medical-devices/sport-medicine/.
SutureBridge Double Row Rotator Cuff Repair Surgical Technique, Arthrex, Inc., www.arthrex.com, 2013, 6 pp.
SwiveLock and FiberChain Knotless Rotator Cuff Repair Surgical Technique, Arthrex, Inc, www.arthrex.com, 2011, 8 pp.
The DoublePlay Biocomposite Suture Anchor, ArthroCare Sports Medicine, www.arthrocaresportsmedicine.com, 2009, 12 pp.
The Fully Threaded Family of Soft Tissue Repair Anchors, Arthrex, Inc., www.arthrex.com, 2012, 6 pp.
The Next Generation in Rotator Cuff Repair, DePuy Mitek, Inc., 2007, 18 pp.
The Next Generation in Shoulder & Elbow Repair and Reconstruction Technology, Arthrex, Inc., www.arthrex.com, 2014, 56 pp.
The Next Generation in Shoulder & Elbow Repair and Reconstruction Technology, Arthrex, Inc., www.arthrex.com, 2015, 56 pp.
The Opus AutoCuff System for Rotator Cuff Repair, ArthroCare Sports Medicine, www.arthrocaresportsmedicine.com, 2006, 8 pp.
The Opus TwinLock Knotless Fixation System, ArthroCare Sports Medicine, www.arthrocaresportsmedicine.com, 2010, 2 pp.
Versalok PEEK, the New, 100% Radiolucent, Self-Punching, Knotless Anchor, DePuy Mitek, Inc., 2010, 4 pp.
Versalok, The Next Generation in Rotator Cuff Repair, DePuy Mitek, 18 pp., 2007.

* cited by examiner

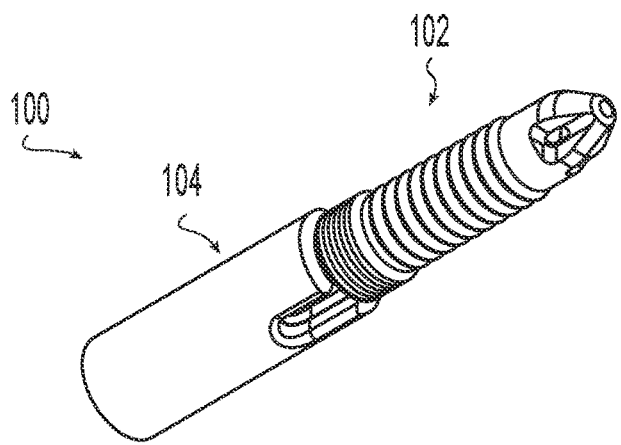
Fig. 1
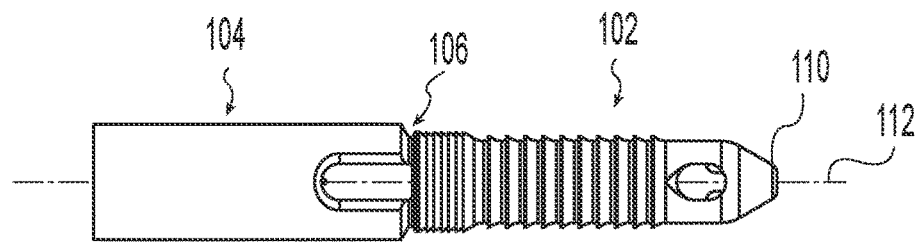
Fig. 2
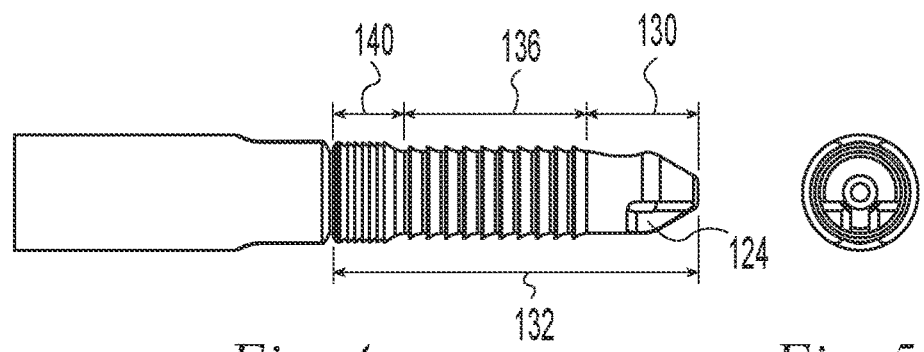
Fig. 3    Fig. 4    Fig. 5
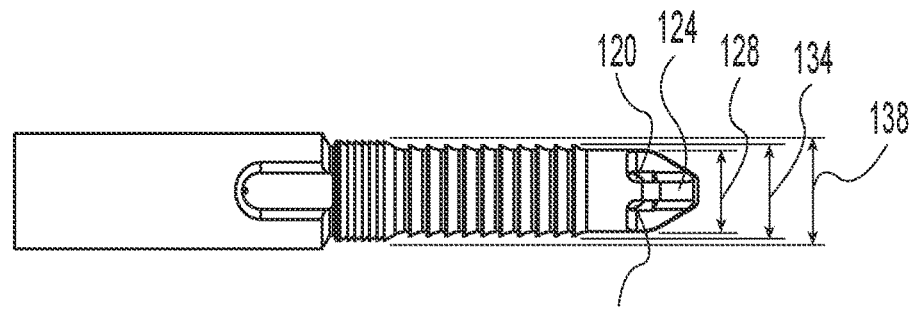
Fig. 6

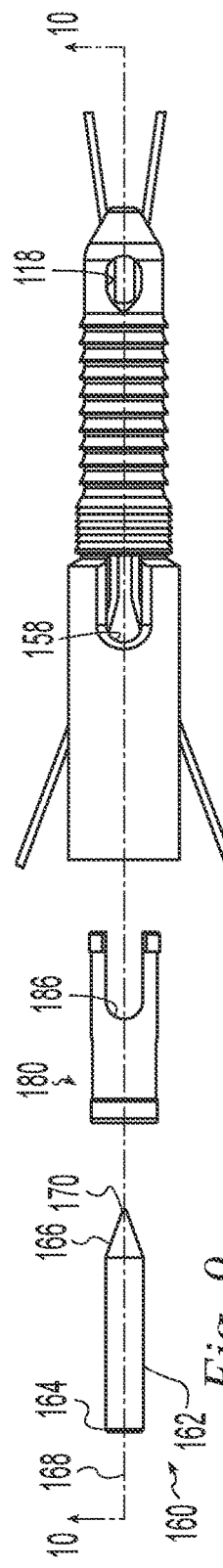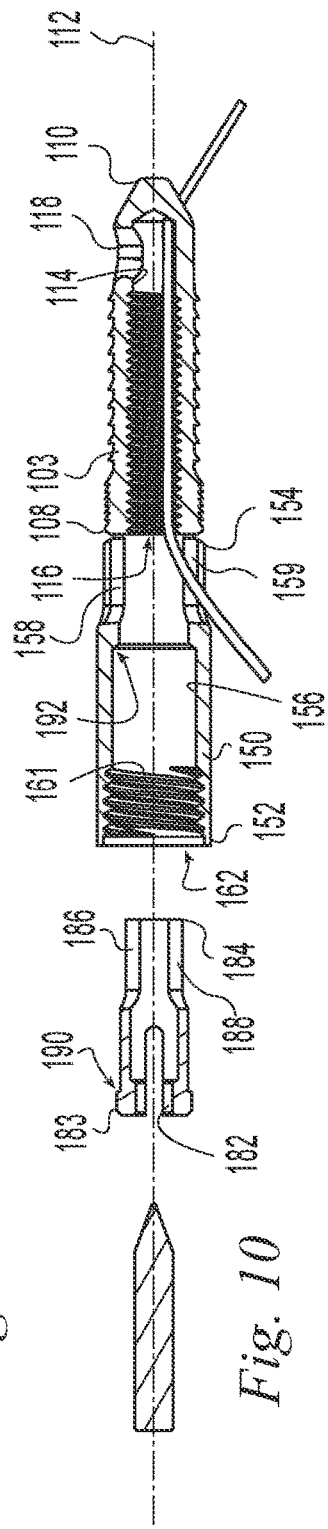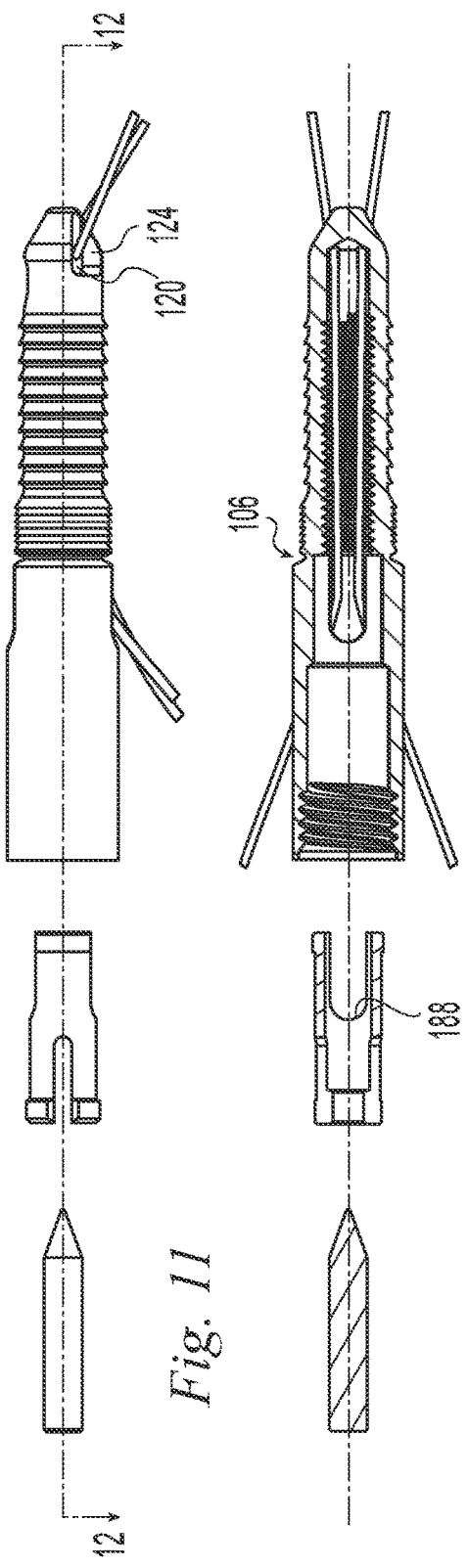
Fig. 9
Fig. 10
Fig. 11
Fig. 12

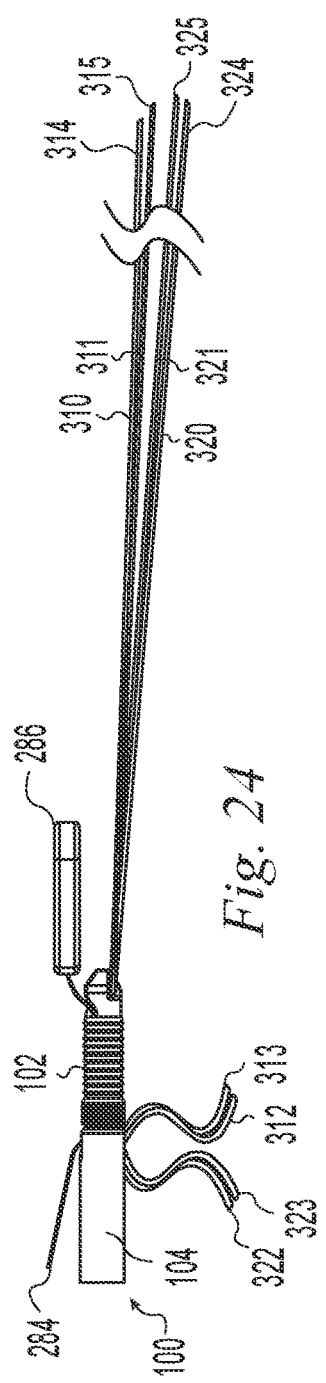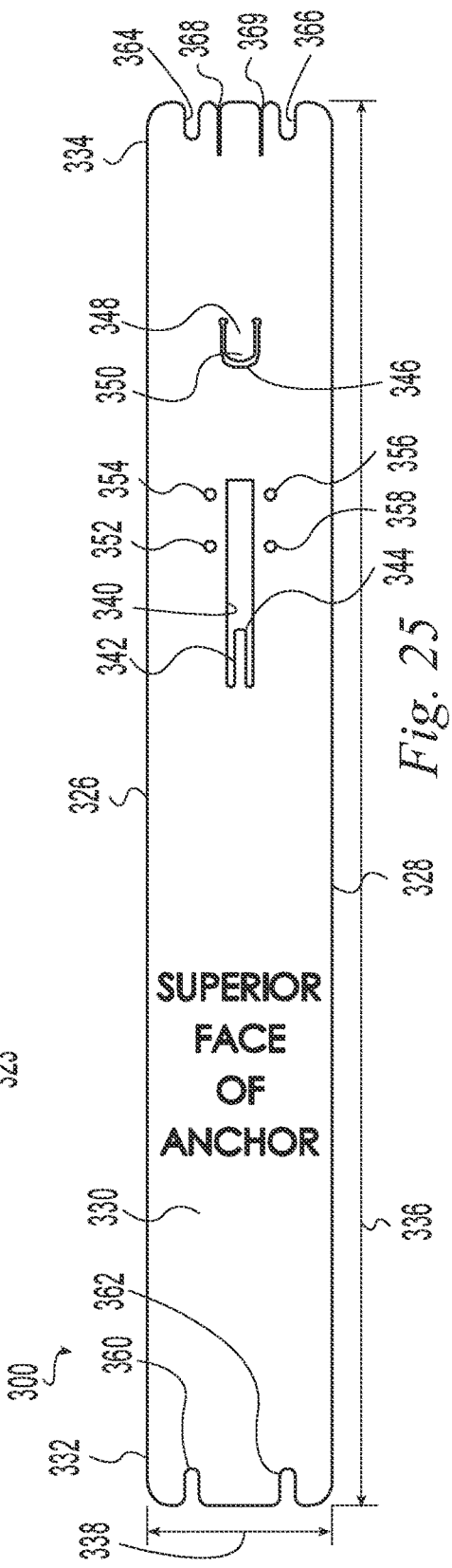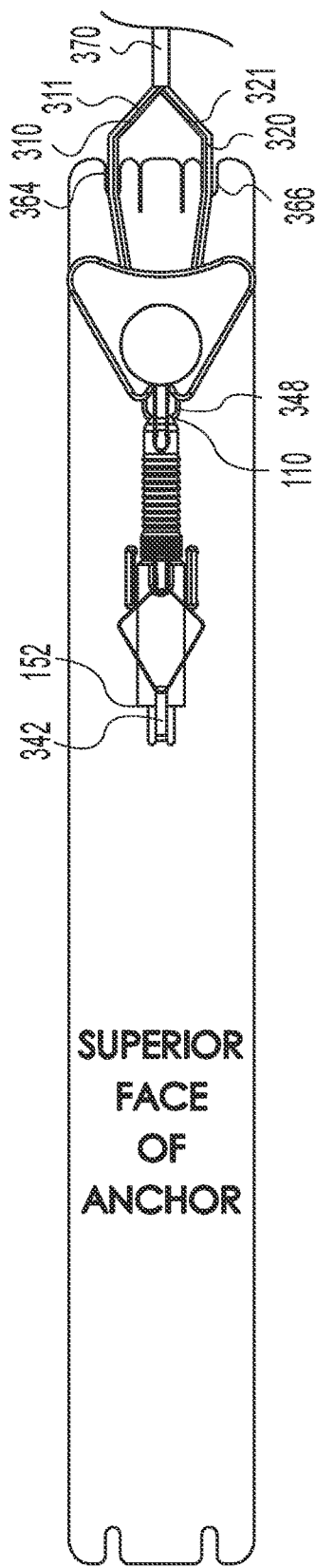

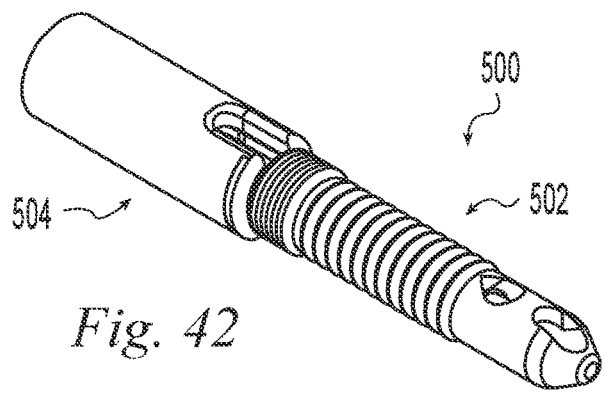
Fig. 42
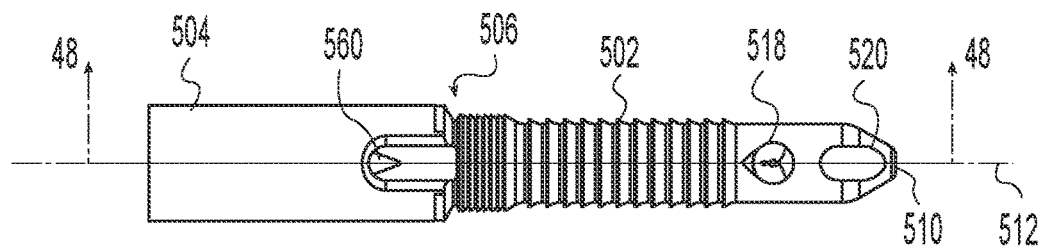
Fig. 43
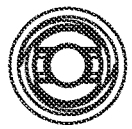 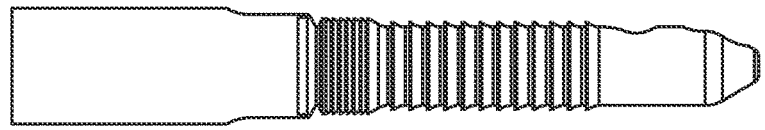 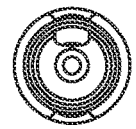
Fig. 44   Fig. 45   Fig. 46
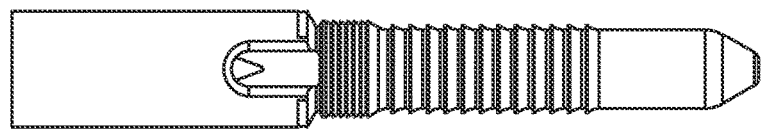
Fig. 47
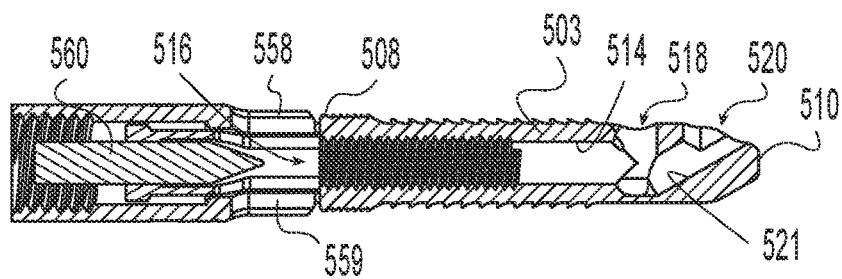
Fig. 48

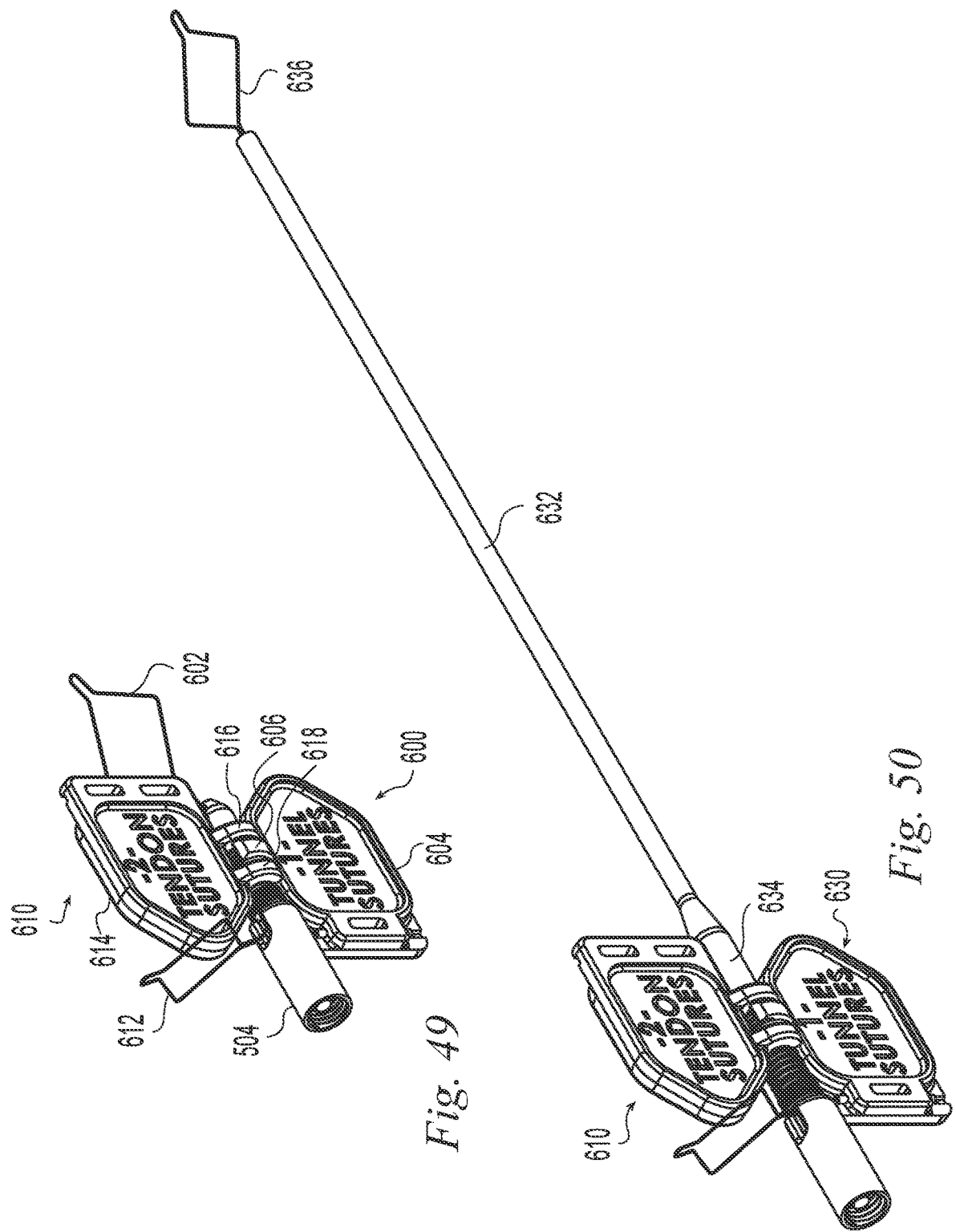

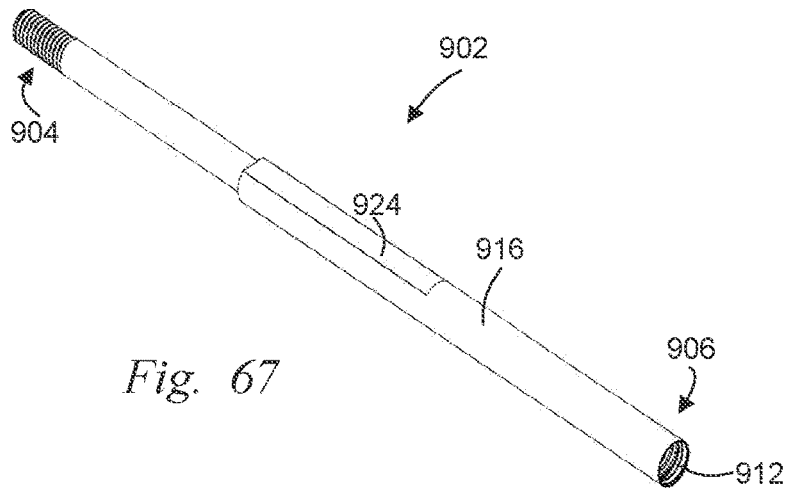
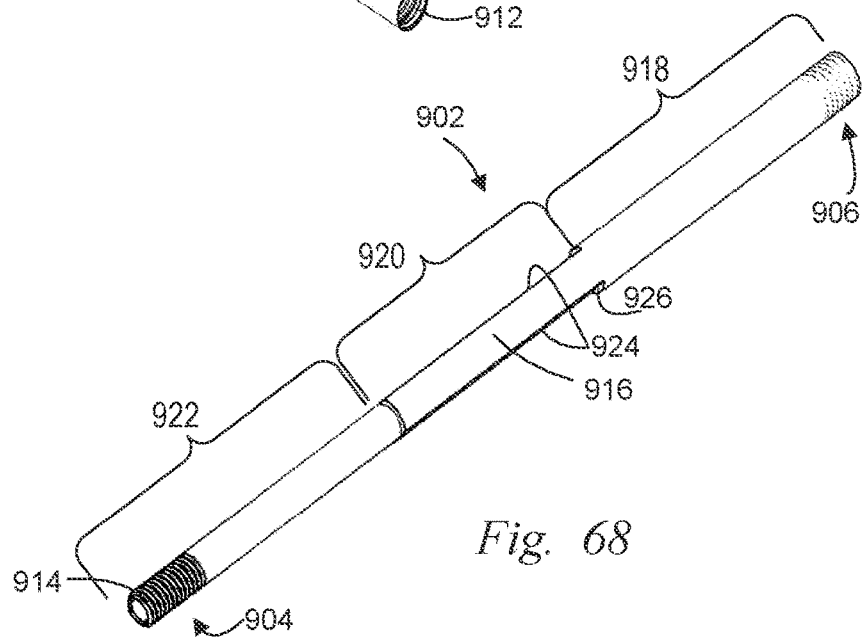
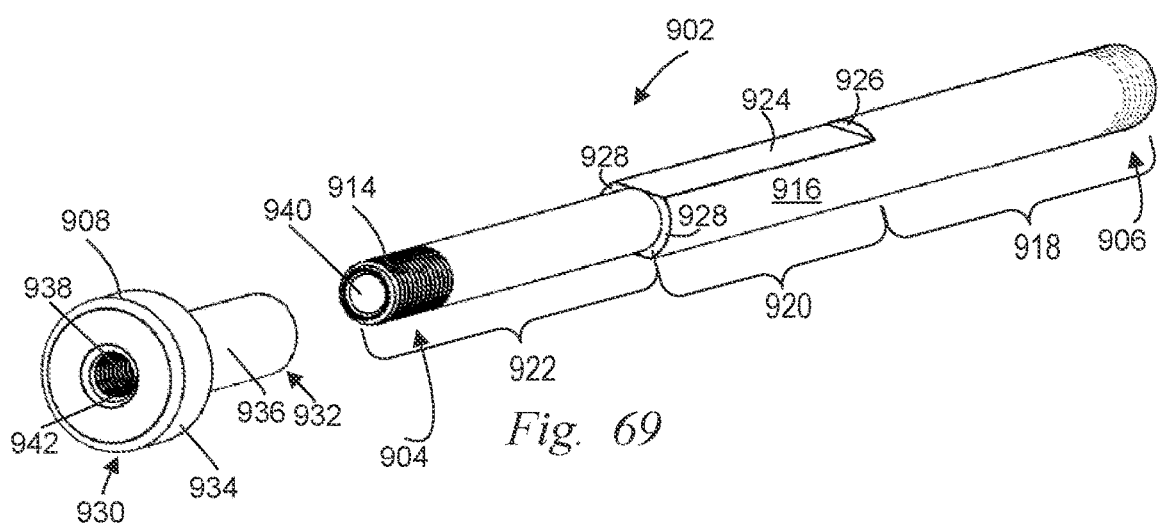

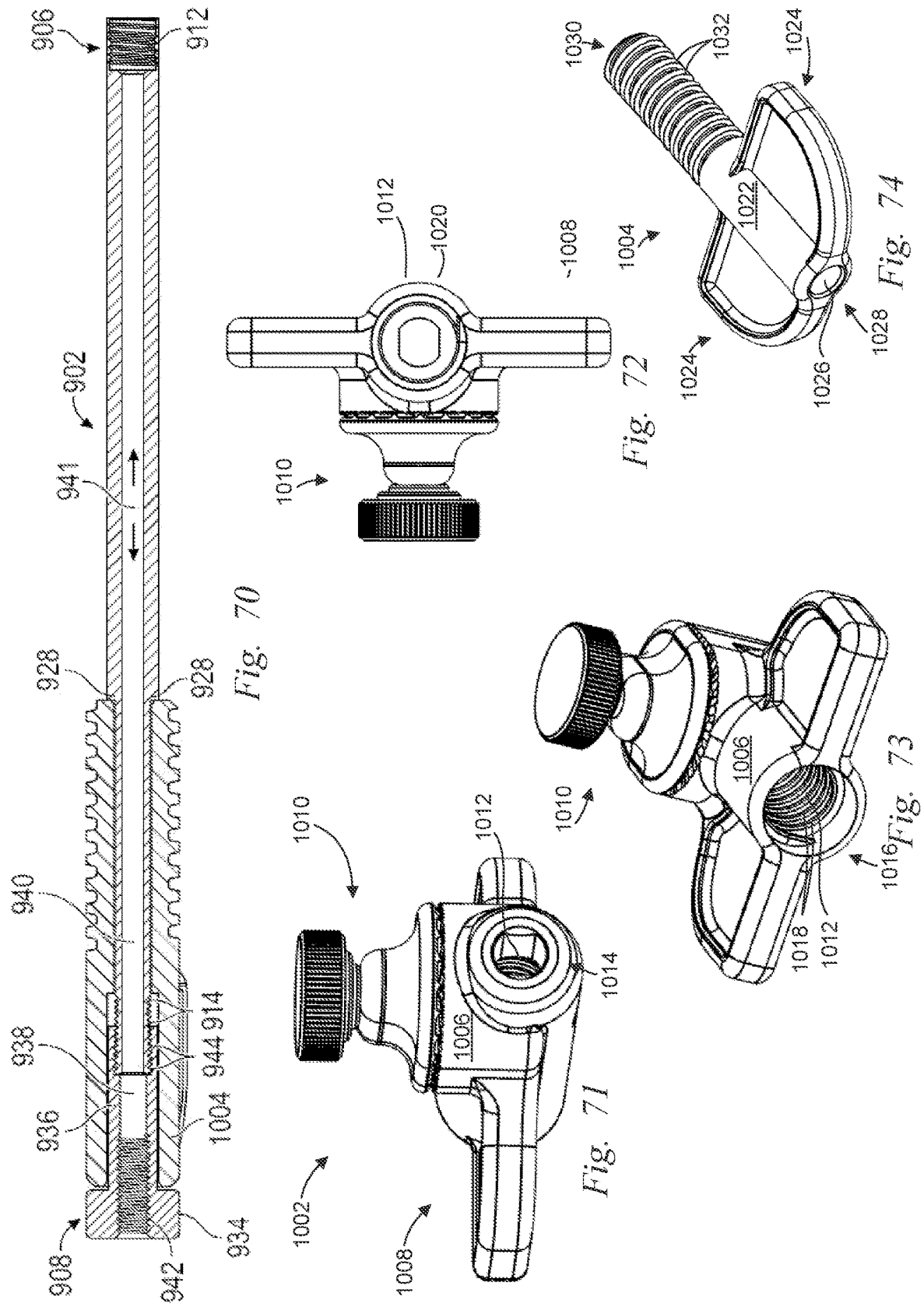

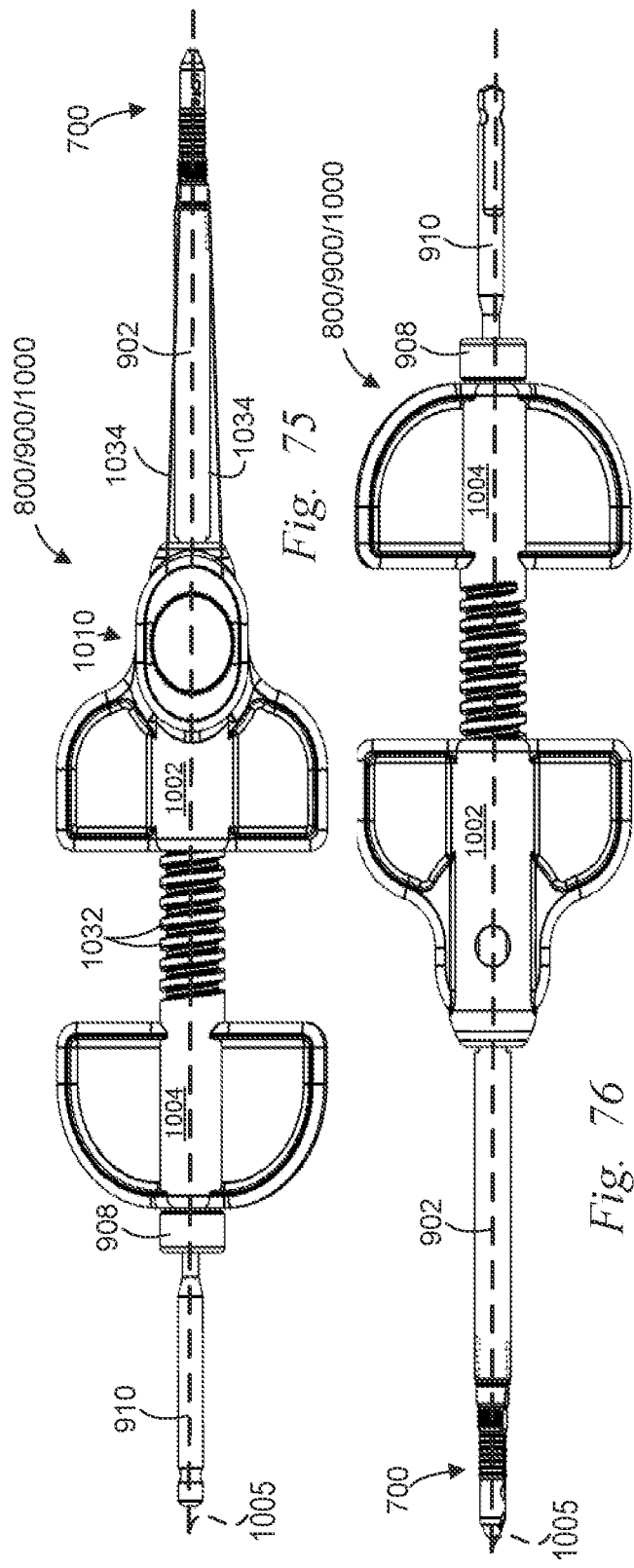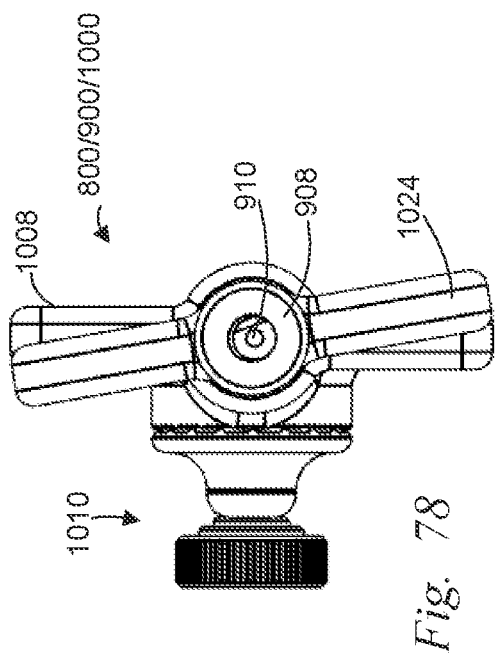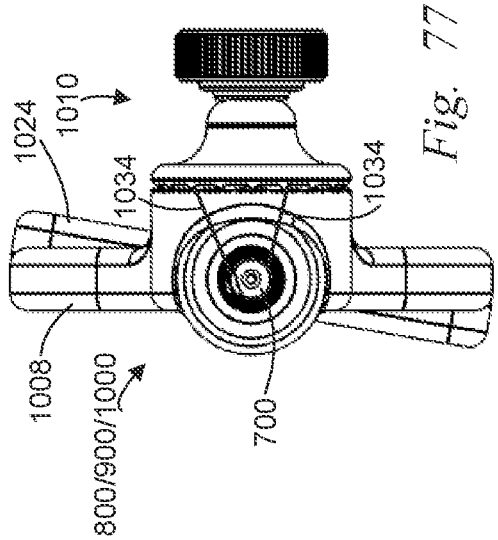

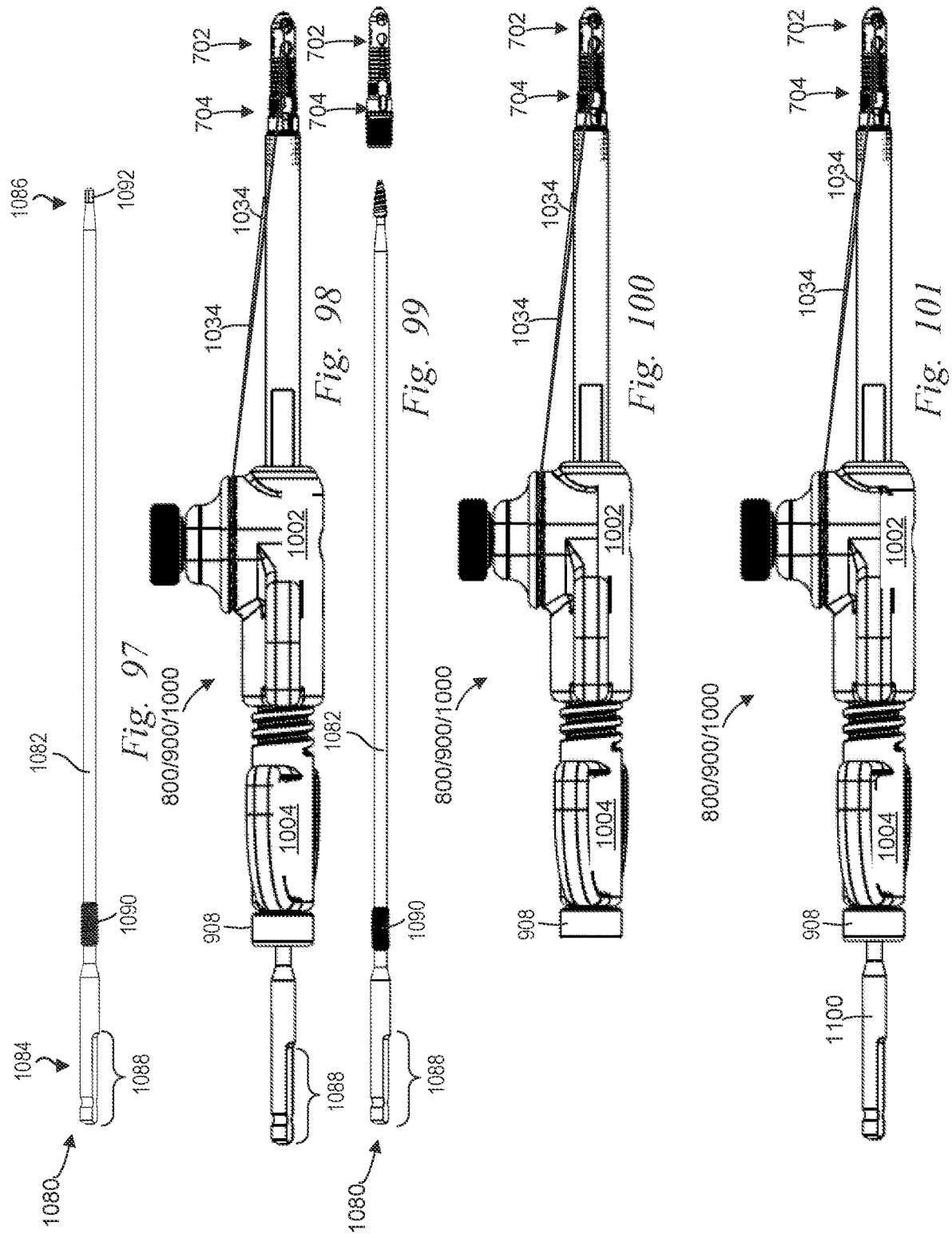

SUTURE ANCHOR

CROSS-REFERENCE TO RELATED APPLICATIONS

This application is a continuation-in-part of U.S. patent application Ser. No. 16/268,973 filed on Feb. 6, 2019, entitled "Transosseous Suture Anchor", which is a continuation of U.S. patent application Ser. No. 15/224,273 filed on Jul. 29, 2016, entitled "Transosseous Suture Anchor", now issued as U.S. Pat. No. 10,226,243 on Mar. 12, 2019, which claims the benefit of U.S. Provisional Application No. 62/200,696, filed Aug. 4, 2015, which are hereby incorporated by reference in their entirety. This application is also a continuation-in-part of U.S. patent application Ser. No. 16/545,371 filed on Aug. 20, 2019, entitled "Extra Joint Stabilization Construct", which is a continuation of U.S. patent application Ser. No. 15/641,592 filed on Jul. 5, 2017 entitled "Extra Joint Stabilization Construct", now issued as U.S. Pat. No. 10,426,459 on Oct. 1, 2019, which claims the benefit of U.S. Provisional Application No. 62/458,975, filed Feb. 14, 2017, U.S. Provisional Application No. 62/456,217, filed Feb. 8, 2017, U.S. Provisional Application No. 62/425,560, filed Nov. 22, 2016, and U.S. Provisional Application No. 62/358,231, filed Jul. 5, 2016, which are hereby incorporated by reference in their entirety. This application is also a continuation-in-part of U.S. patent application Ser. No. 16/871,485 filed on May 11, 2020, entitled "Intra Joint Stabilization Construct", which is a continuation of U.S. patent application Ser. No. 15/641,573 filed on Jul. 5, 2017 entitled "Intra Joint Stabilization Construct", now U.S. Pat. No. 10,682,131 issued on Jun. 16, 2020, which also claims the benefit of U.S. Provisional Application No. 62/458,975, filed Feb. 14, 2017, U.S. Provisional Application No. 62/456,217, filed Feb. 8, 2017, U.S. Provisional Application No. 62/425,560, filed Nov. 22, 2016, and U.S. Provisional Application No. 62/358,231, filed Jul. 5, 2016, which are hereby incorporated by reference in their entirety.

TECHNICAL FIELD

Examples of the present disclosure relate to implants, instruments and methods for surgical transosseous attachment to a bone and/or surgical attachment to soft or hard tissue. More particularly, examples of the present disclosure relate to knotless suture anchors.

BACKGROUND

A variety of surgical procedures require the attachment of something relative to a surgical site. For example, in surgery relating to the skeletal system, it is often advantageous to attach soft tissue, suture, implants, and/or other items in or adjacent to a bone. For example, soft tissues such as ligaments, tendons, fascia, other capsular material, and/or muscle may be attached to a bone. Such soft tissues may be adjacent bones at skeletal joints including but not limited to the joints of the hands and feet, ankle, wrist, knee, elbow, hip, shoulder, and spine. For example, it is often advantageous to pass a suture through a portion of a bone to form a transosseous attachment to the bone.

SUMMARY

The various apparatus, devices, systems, and/or methods of the present disclosure have been developed in response to the present state of the art, and in particular, in response to the problems and needs in the art that have not yet been fully solved by currently available suture anchors and related instrumentation. One general aspect of the present disclosure can include, a knotless suture anchor system that includes an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a distal opening communicating with the longitudinal passageway nearer the distal end; an interference member insertable distally into the longitudinal passageway to secure a portion of a suture within the longitudinal passageway by compressing the portion of the suture between the interference member and the anchor body, and a frangible connection that joins a proximal member to the anchor body.

Implementations may include one or more of the following features. The knotless suture anchor system may include a driver operable to urge the interference member into the anchor body, and operable to move the interference member out of the anchor body. The driver may include: a drive shaft having a proximal end and a distal end; a drive coupler connected to the drive shaft at the proximal end; a drive feature connected to the drive shaft at the distal end; and external drive threads between the proximal end and the distal end, the external drive threads configured to engage internal drive threads of an inserter. The driver is configured to apply a torque to the interference member that engages at least one external helical thread of the interference member with an internal thread of the anchor body. The proximal end of the anchor body includes internal helical threads, and the interference member may include a set screw having external helical threads configured to interface with the internal helical threads in a clearance fit having a length of thread engagement shorter than a length of the external helical threads.

The external helical threads of the set screw may include knuckle threads having an external helical thread pitch different from an internal helical thread pitch of the internal helical threads. The knotless suture anchor system may include a tensioner operable to engage the proximal member and secure a suture extending from the anchor body. The shaft, carriage, and second handle are coaxial with the longitudinal axis and include an inserter longitudinal passageway in communication with the longitudinal passageway of the anchor body. The suture grip member may include: a superior grip plate having ridges; an inferior grip plate having ridges; and a fastener that compresses the superior grip plate against the inferior grip plate and secure a portion of the suture between the superior grip plate and inferior grip plate.

The fastener may include a thumb screw and the superior grip plate may include a recess that accepts a boss of the inferior grip plate, the boss having ridges. The knotless suture anchor system may include an inserter operable to engage the proximal member in an axial force transmitting relationship in a first direction, the inserter having a pushrod mounted for axial translation within the inserter, the pushrod operable to engage one of the interference member and the anchor body in an axial force transmitting relationship in a second direction opposite the first direction and break the frangible connection between the proximal member and the anchor body in response to axial translation of the pushrod relative to the inserter.

One general aspect of the present disclosure can include the knotless suture anchor system having an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a first distal opening communicating with the longitudinal passageway nearer the distal end; and a tensioner connected to the anchor body and operable to engage the proximal end, secure a suture extending from the anchor body, and apply tension to the suture.

Implementations may include one or more of the following features. The knotless suture anchor system may include an interference member insertable distally into the longitudinal passageway to secure a portion of a suture within the longitudinal passageway by compressing the portion of the suture between the interference member and the anchor body. The knotless suture anchor system may include a proximal member connected to the proximal end of the anchor body by a frangible connection. The knotless suture anchor system may include an inserter operable to engage the proximal member in an axial force transmitting relationship in a first direction, the inserter having a pushrod mounted for axial translation within the inserter, the pushrod operable to engage the interference member in an axial force transmitting relationship in a second direction opposite the first direction and break the frangible connection between the proximal member and the anchor body in response to axial translation of the pushrod relative to the inserter.

The inserter may include a shaft having a proximal end and a distal end, the shaft operable to engage the proximal member at the distal end of the shaft, the shaft coupled to a tensioner may include: a carriage having a suture grip member that removably secures a portion of the suture to the carriage, the carriage having first threads; a puller connected to the shaft near the proximal end of the shaft, the puller having second threads that engage the first threads; where the shaft, carriage, and puller are coaxial with the longitudinal axis and include an inserter longitudinal passageway in communication with the longitudinal passageway of the anchor body. The proximal member may include external helical threads configured to engage internal helical threads of the shaft.

One general aspect of the present disclosure can include the knotless suture anchor system having an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a first distal opening communicating with the longitudinal passageway nearer the distal end; a proximal member joined to the anchor body, the proximal member having external threads at a proximal end of the proximal member; a set screw insertable distally into the longitudinal passageway to releasably secure a first portion of a suture within the longitudinal passageway by compressing the first portion of the suture between external knuckle threads of the set screw and internal helical threads at the proximal end of the anchor body; a frangible connection that joins the proximal member to the anchor body; and a tensioner connected to an inserter operable to engage the proximal member, the tensioner operable to secure a second portion of the suture contiguous to the first portion and extending from the anchor body, the tensioner also operable to apply tension to the second portion of the suture.

Implementations may include one or more of the following features. The knotless suture anchor system where the inserter is operable to engage the proximal member in an axial force transmitting relationship in a first direction, the inserter having a pushrod mounted for axial translation within the inserter, the pushrod operable to engage the set screw in an axial force transmitting relationship in a second direction opposite the first direction and break the frangible connection to separate the anchor body from the proximal member in response to axial translation of the pushrod relative to the inserter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1 is a perspective view of an implant according to one embodiment;

FIG. 2 is a top view of the implant of FIG. 1;

FIG. 3 is a left side view of the implant of FIG. 1;

FIG. 4 is a front view of the implant of FIG. 1;

FIG. 5 is a right side view of the implant of FIG. 1;

FIG. 6 is a bottom view of the implant of FIG. 1;

FIG. 9 is an exploded top view of the implant of FIG. 1;

FIG. 10 is an exploded section view taken along line 10-10 of FIG. 9;

FIG. 11 is an exploded front view of the implant of FIG. 1;

FIG. 12 is an exploded section view taken along line 12-12 of FIG. 11;

FIG. 24 is a side view of the implant of FIG. 1 preloaded with suture and a suture passer according to one embodiment;

FIG. 25 is a top view of a suture keeper according to one embodiment;

FIGS. 26-31 are a sequence of top and bottom views of the implant of FIG. 1 preloaded as in FIG. 24 being loaded onto the suture keeper of FIG. 25;

FIG. 42 is a perspective view of an implant according to one embodiment;

FIG. 43 is a top view of the implant of FIG. 42;

FIG. 44 is a left side view of the implant of FIG. 42;

FIG. 45 is a front view of the implant of FIG. 42;

FIG. 46 is a right side view of the implant of FIG. 42;

FIG. 47 is a bottom view of the implant of FIG. 42;

FIG. 48 is a side section view of the implant of FIG. 42 taken along line 48-48 of FIG. 43;

FIG. 49 is a perspective view of the implant of FIG. 42 preloaded with suture passers according to one embodiment;

FIG. 50 is a perspective view of the implant of FIG. 42 preloaded with suture passers and a suture management tube according to one embodiment;

FIG. 67 is a distal perspective view of a shaft of the system of FIG. 66 according to one embodiment;

FIG. 68 is a proximal perspective view of a shaft of the system of FIG. 66 according to one embodiment;

FIG. 69 is a proximal perspective view of a shaft and a collar of the system of FIG. 66 according to one embodiment;

FIG. 70 is a section view of a collar and a puller on a shaft of the system of FIG. 66 according to one embodiment;

FIG. 71 is a perspective view of a carriage of the system of FIG. 66 according to one embodiment;

FIG. 72 is a right side view of a carriage of the system of FIG. 66 according to one embodiment;

FIG. 73 is a left side perspective view of a carriage of the system of FIG. 66 according to one embodiment;

FIG. 74 is a left side perspective view of a puller of the system of FIG. 66 according to one embodiment;

FIG. 75 is a top view of the system of FIG. 66 according to one embodiment;

FIG. 76 is a bottom view of the system of FIG. 66 according to one embodiment;

FIG. 77 is a right side view of the system of FIG. 66 according to one embodiment;

FIG. 78 is a left side view of the system of FIG. 66 according to one embodiment;

FIG. 97 is a perspective view of a driver for use with the system of FIG. 66 and the implant of FIG. 52 according to one embodiment;

FIG. 98 is a perspective view illustrating use of the system of FIG. 66 and the implant of FIG. 52 according to one embodiment in another stage of the sequence illustrated in FIGS. 93-96;

FIG. 99 is a perspective view of a driver for use within the system of FIG. 66 and the implant of FIG. 52 according to one embodiment;

FIGS. 100-101 are a sequence of perspective views illustrating use of the system of FIG. 66 and the implant of FIG. 52 according to one embodiment;

DETAILED DESCRIPTION

Figure 7:
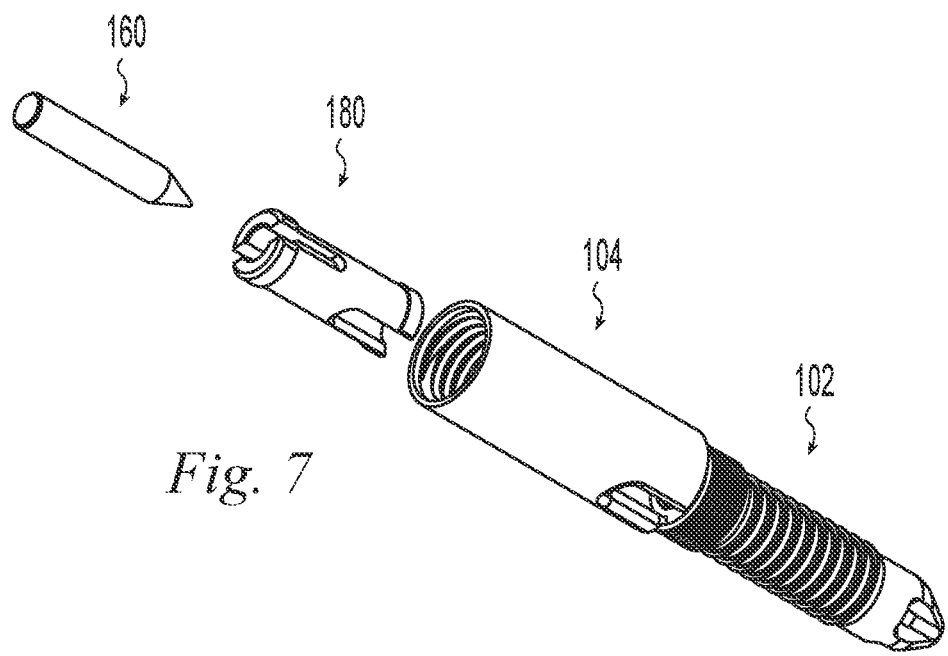
FIG. 7 is an exploded perspective view of the implant of FIG. 1.
Figure 8:
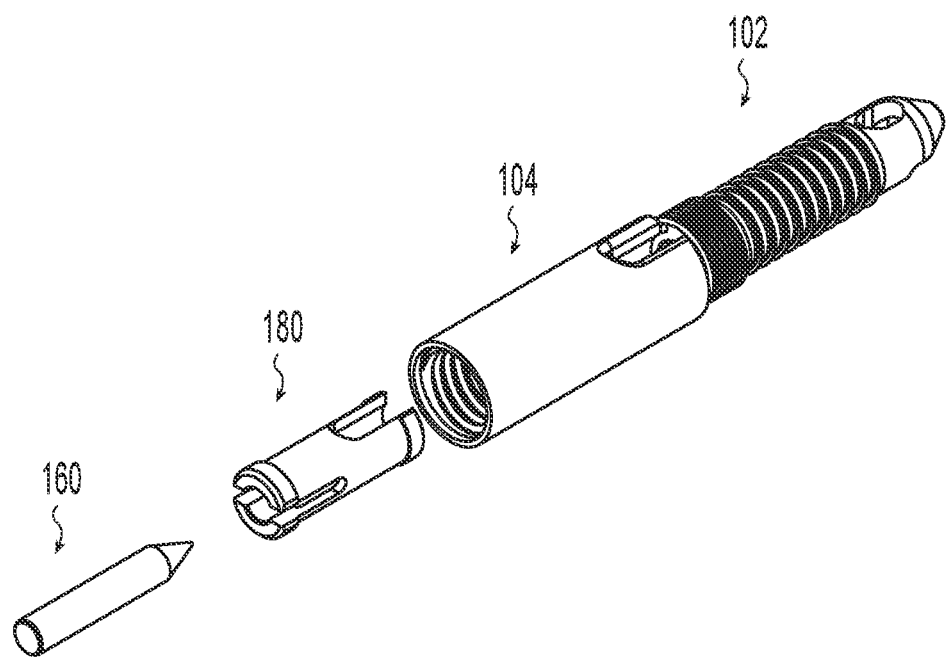
FIG. 8 is an exploded perspective view of the implant of FIG. 1.

The following illustrative examples depict implants, instruments and methods to anchor a suture to a bone. The illustrative examples depict anchoring a round suture in a bone tunnel to attach soft tissue to the bone. However, examples of instruments and methods of the present disclosure may be used to anchor other elements in a bone tunnel including suture tapes, cables, soft tissues, grafts, and other elements. While illustrative examples of methods depict the attachment of the soft tissue of the rotator cuff to a humeral bone, it will be understood that examples of instruments and methods of the present disclosure may be used to anchor any member in any bone, at surgical sites anywhere in a patient's body, and for any purpose.

Standard medical planes of reference and descriptive terminology are employed in this specification. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular. Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body.

Proximal means toward the trunk of the body. Proximal may also mean toward a user or operator. Distal means away from the trunk. Distal may also mean away from a user or operator. Dorsal means toward the top of the foot. Plantar means toward the sole of the foot. Antegrade means forward moving from a proximal location/position to a distal location/position or moving in a forward direction. Retrograde means backward moving from a distal location/position to a proximal location/position or moving in a backwards direction.

The terms "suture" and/or "suture strand" are used herein to mean any strand or flexible member, natural or synthetic, able to be anchored in a bone tunnel and useful in a surgical procedure. In certain embodiments, "suture" and/or "suture strand" refers to a flexible line or flexible member of natural material, natural biological material, biomaterial, biomimetic materials, manmade material, or a combination of these either in a single structure, a composite structure, or a plurality of tissue structures that extend in parallel and/or may be woven or bonded together. In certain embodiments, a suture may be long and thin. In certain embodiments, a suture may be planar or may be elastic or inelastic. Examples of a suture include, but are not limited to, a thread, a suture, suture tape, a woven structure, a fibrous material, a cord, and/or any of these in combination with each other, and the like. The term "transverse" is used herein to mean to cross at an angle; i.e. not parallel. The term includes but is not limited to right angles.

FIGS. 1-12 depict an illustrative example of a suture anchor. The anchor 100 has an anchor body 102, a proximal member 104 joined to the anchor body 102 by a frangible connection 106 and a suture locking member 160. The frangible connection may include, for example, a thin wall (as shown), a perforated section, an intermediate material such as an adhesive, and/or other suitable frangible constructions. In the illustrative example of FIGS. 1-12, the anchor body 102 is generally cylindrical and has a sidewall 103 (FIG. 10) defining an exterior surface, a proximal end 108, a distal end 110, and a longitudinal axis 112 extending between the proximal and distal ends 108, 110. An interior longitudinal passageway 114 extends at least partway from the proximal end 108 toward the distal end 110. A proximal opening communicates with the longitudinal passageway nearer the proximal end 108 and a distal opening communicates with the longitudinal passageway nearer the distal end 110. In the illustrative embodiment of FIGS. 1-12, the proximal opening 116 communicates through the proximal end 108 of the anchor body 102 along the axis 112 with the passageway 114. The distal opening comprises a plurality of distal openings that communicate from the exterior surface of the anchor body 102 through the sidewall 103 to the passageway 114.

In the illustrative example of FIGS. 1-12, the distal openings include a single superior opening 118 and two inferior openings 120, 122. The superior opening 118 is formed through the sidewall 103 and centered over the longitudinal axis of the anchor body. The two inferior openings 120, 122 are formed through the sidewall 103 opposite the superior opening 118 and spaced on either side of the longitudinal axis and separated by a dividing wall 124. All of the superior and inferior distal openings 118, 120, 122 are spaced proximally away from the distal end 110 of the anchor body.

In the illustrative example of FIGS. 1-12, the anchor body 102 has a first exterior dimension 128, perpendicular to the longitudinal axis, over a first portion 130 of its exterior length 132; a second exterior dimension 134, perpendicular to the longitudinal axis, greater than the first dimension 128, over a second portion 136 of its exterior length 132; and a third exterior dimension 138, perpendicular to the longitudinal axis, greater than the second dimension 134, over a third portion 140 of its exterior length 132. For example, the first dimension 128 may be less than or equal to a radial dimension of a bone hole to ease alignment and initial insertion of the anchor body 102 into the bone hole. The second dimension 134 may be larger than the radial dimension of the bone hole to create a press fit of the second portion 136 within the bone hole to resist removal of the anchor body 102 from the bone hole. The third dimension 138 may create an even tighter press fit in the bone hole. The third portion 140 will require the greatest insertion force. By making the length of the third portion 140 relatively short, the total effort to insert the anchor body 102 will be lessened and the maximum insertion force will only be required to insert the relatively short third portion. The second and third portions 136, 140 may also have ribbed surfaces to further resist removal of the anchor body 102 from the bone hole. The spacing, or pitch, of the ribs may vary. For example, the second portion 136 may have ribs with relatively wider spacing for positioning in a relatively wide band of cancellous bone and the third portion 140 may have ribs with relatively narrower spacing for positioning in a relatively narrow band of cortical bone.

In the illustrative example of FIGS. 1-12, the proximal member 104 is generally cylindrical and has a sidewall 150 (FIG. 10) defining an exterior surface, a proximal end 152, a distal end 154, and a longitudinal axis coaxial with the anchor body longitudinal axis 112 extending between the proximal and distal ends 152, 154. An axial through bore 156 extends through the proximal member 104 from the proximal end 152 to the distal end 154 and communicates with the longitudinal passageway 114 of the anchor body 102. At least one opening formed through the sidewall 150 of the proximal member 104 allows one or more sutures to be routed through the anchor body 102 without passing through the proximal end of the proximal member axial through bore 156. In the illustrative example of FIGS. 1-12, a first, superior "U"-shaped opening 158 is formed through the sidewall 150 near the distal end 154 and a second, inferior "U"-shaped opening 159 is formed through the sidewall 150 near the distal end 154 opposite the first opening 158. The "U"-shaped openings intersect the frangible connection 106. While the proximal member 104 and anchor body 102 are joined, the "U"-shaped openings 158, 159 each have a closed perimeter. When the proximal member 104 and anchor body 102 are separated at the frangible connection 106, the distal perimeter of each opening 158, 159 is removed such that separation of the proximal member 104 and anchor body 102 at the frangible connection 106 transforms the opening 158, 159 into open, "U"-shaped slots with the open side facing distally. The proximal member 104 includes an engagement portion for engaging a driver. In the illustrative example of FIGS. 1-12, the engagement portion includes an internal helical thread 161 operable to engage a driver in axial force transmitting relationship.

In the illustrative example of FIGS. 1-12, the suture locking member 160 is in the form of an interference member operable to axially slide into the longitudinal passageway 114 of the anchor body 102 to secure a suture within the longitudinal passageway 114 by compressing the suture between the locking member 160 and the anchor body 102. In the illustrative example of FIGS. 1-12, the suture locking member 160 has an elongate cylindrical body 162 having a proximal end 164, a distal end 166, and a longitudinal axis 168 extending between the proximal and distal ends 164, 166. The body 162 has a dimension perpendicular to the longitudinal axis 168 less than or equal to the diameter of the anchor body passageway 114. Preferably the body 162 tapers distally. More preferably the body 162 tapers to a point 170.

In the illustrative example of FIGS. 1-12, the suture locking member 160 is mounted in the axial through bore 156 of the proximal member 104 in axial sliding relationship so that it may be pressed out of the proximal member 104 and into the anchor body 102 to lock a suture in the anchor body 102.

In the illustrative example of FIGS. 1-12, the suture locking member 160 is retained in the proximal member 104 by a retainer 180 having an outer surface engaging the axial through bore 156 of the proximal member in axial sliding relationship and an axial aperture 182 receiving the locking member 160 in axial sliding relationship. The retainer 180 is also arranged to engage the anchor body 102 in axial force transmitting relationship. In the illustrative example of FIGS. 1-12, the retainer 180 is generally cylindrical and the axial aperture 182 extends through the retainer 180 from a proximal end 183 to a distal end 184. The outer diameter of the distal end 184 of the retainer 180 is larger than the diameter of the passageway 114 in the implant body 102. The distal end of the retainer 180 is operable to engage the proximal end of the implant body 102. The retainer 180 includes opposed superior and inferior "U"-shaped slots 186, 188 opening distally and aligning with the superior and inferior "U"-shaped openings 158, 159 in the proximal member 104 when the retainer 180 is seated in the proximal member 104. The retainer 180 includes a distal facing shoulder 190 operable to engage a proximal facing shoulder 192 formed in the through bore 156 of the proximal member to prevent the retainer from being completely expelled distally from the proximal member 104.

Figure 13:
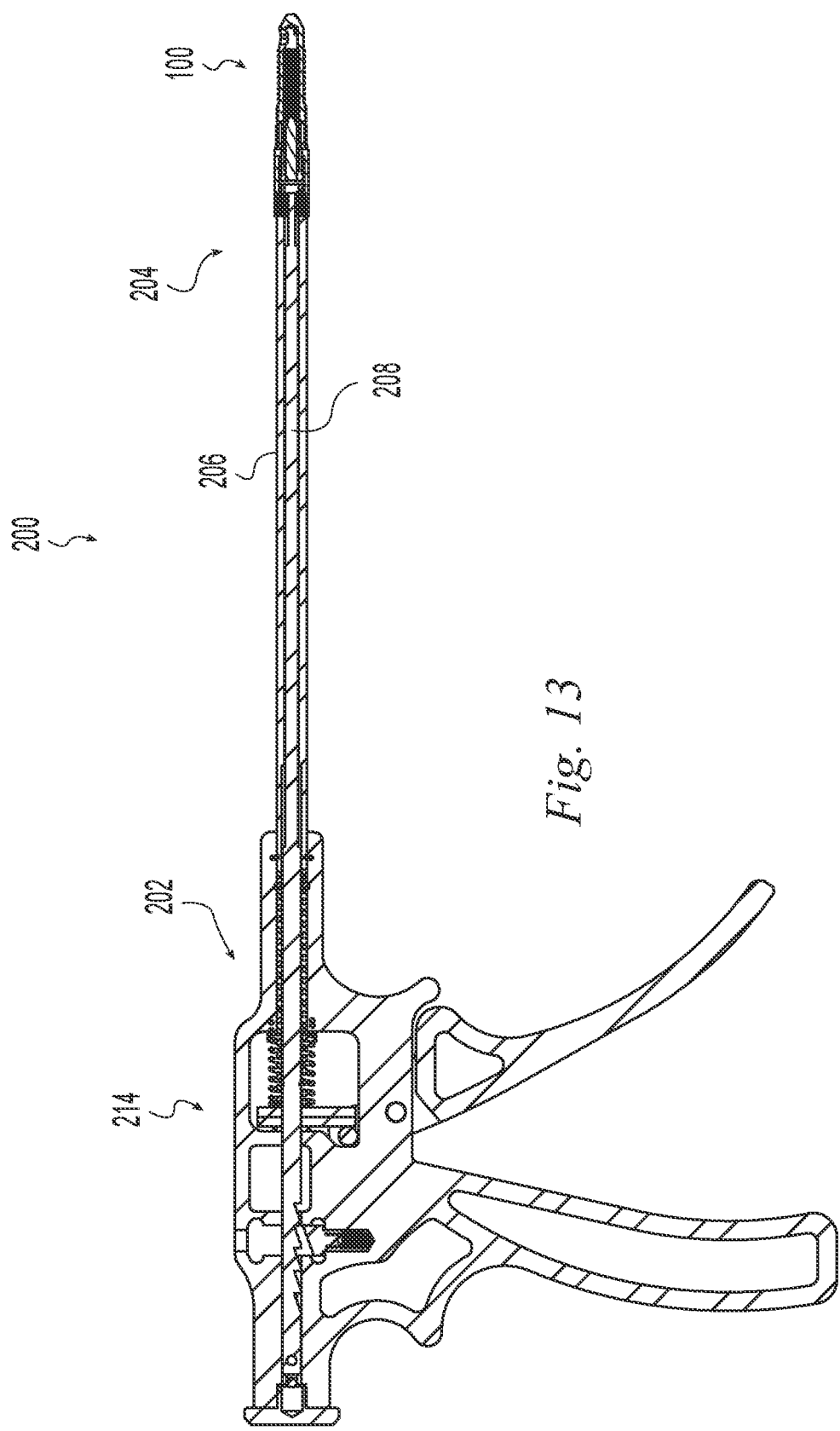
FIG. 13 is a side section view of an instrument useable with the implant of FIG. 1 according to one embodiment.
Figure 14:
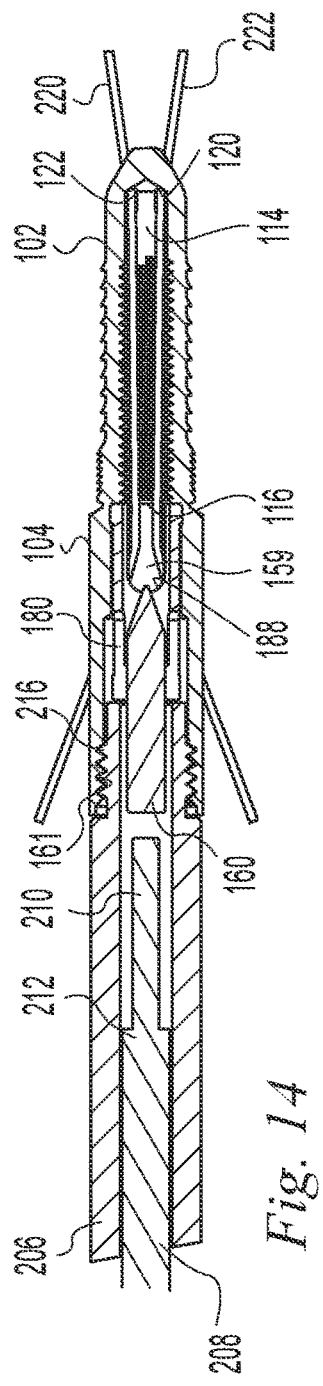
FIGS. 14-16 are a sequence of detail top section views illustrating the interaction of the implant of FIG. 1 with the system of FIG. 13 according to one embodiment.

FIG. 13 depicts an illustrative example of an inserter 200 for use with the suture anchor 100. FIGS. 14-19 depict the inserter 200 in use with the suture anchor 100. The inserter 200 extends from a proximal end 202 to a distal end 204. The inserter 200 has an elongated hollow shaft 206 and an elongated pushrod 208 mounted for axial translation within the hollow shaft. The shaft 206 includes an engagement feature at its distal end operable to engage the proximal member 104 of the suture anchor 100 in axial force transmitting relationship. In the illustrative example of FIG. 13, the shaft 206 includes an external helical thread 216 engageable with the internal helical thread 161 of the proximal member 104 (FIG. 14). The distal end of the pushrod 208 has a first portion 210 sized to engage the proximal end of the suture locking member 160 in axial force transmitting relationship while being operable to slide through the aperture 182 of the retainer 180. The distal end of the pushrod 208 has a second portion 212 sized to engage the proximal end of the retainer 180 in axial force transmitting relationship. The first portion 210 extends distally from the second portion 212. An advancement mechanism 214 at the proximal end of the inserter 200 is operable to advance the pushrod 208 distally relative to the shaft 206. For example, the advancement mechanism 214 may include any pushrod advancement mechanism such as those well known in the art for advancing plungers in syringe injectors, bone cement injectors, and other liquid and paste dispensers. The example of FIG. 13 illustrates such a mechanism including a trigger mounted to a base member in pivoting relationship. The pushrod is slidingly engaged with the base member and a pair of advancement plates. When the trigger is actuated, it presses on the advancement plates causing them to tilt and bind on the pushrod. Further actuation of the trigger advances the advancement plates and the pushrod distally together. When the trigger is released, a spring straightens the advancement plates and moves the advancement plates and the trigger proximally back to their initial positions. A ratchet mechanism prevents the pushrod from moving proximally. The ratchet mechanism includes ratchet teeth cut into the proximal end of the pushrod and a spring loaded ratchet pawl mounted in the base member at the rear of the pushrod. An actuator (not shown) may be actuated to disengage the ratchet pawl so that the pushrod may be moved proximally and reset to its initial position.

Referring to FIGS. 14-19 one or more sutures are threaded through the anchor body 102 between the proximal and distal openings. In the illustrative example of FIGS. 14-19, separate suture limbs 220, 222 are threaded through each of the inferior distal openings 120, 122 of the anchor body 102, through the longitudinal passageway 114 of the anchor body 102, out the proximal opening 116 of the anchor body 102 and down through the inferior "U"-shaped slot 188 of the retainer 180 and the inferior "U"-shaped opening 159 of the proximal member 104. The suture locking member 160 is retained within the retainer 180 which is received in the proximal member 104. The shaft 206 of the inserter 200 is threadingly engaged with the proximal end of the proximal member 104.

Figure 15:
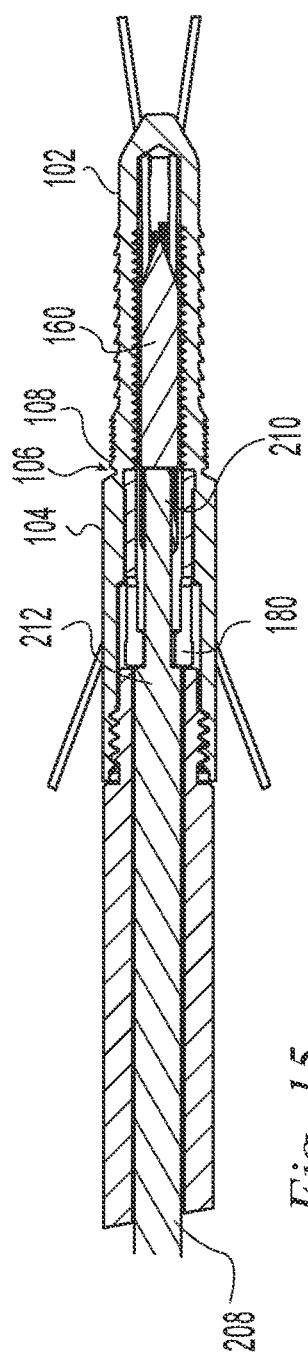
Figure 16:
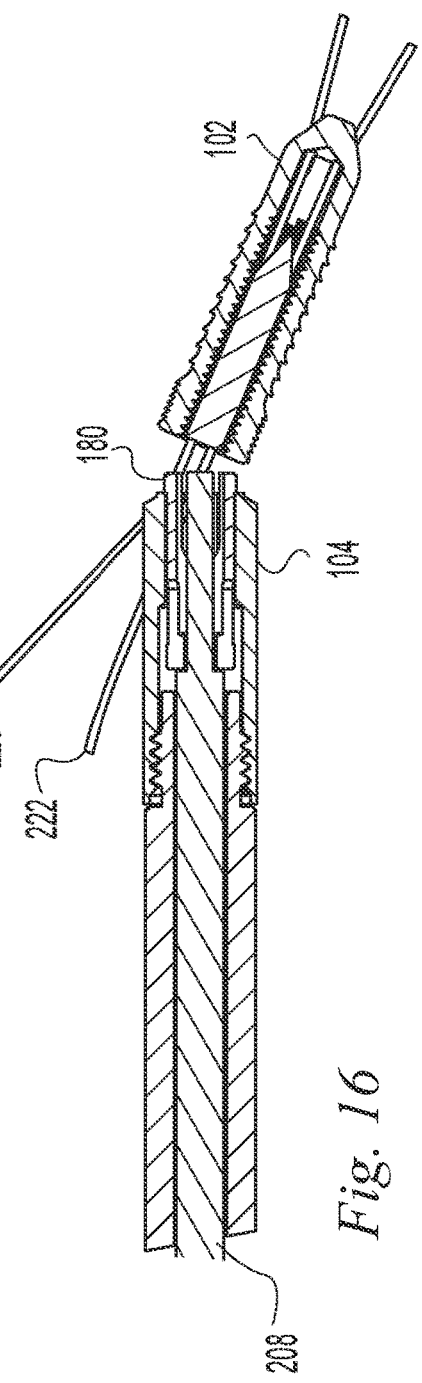
Figure 17:
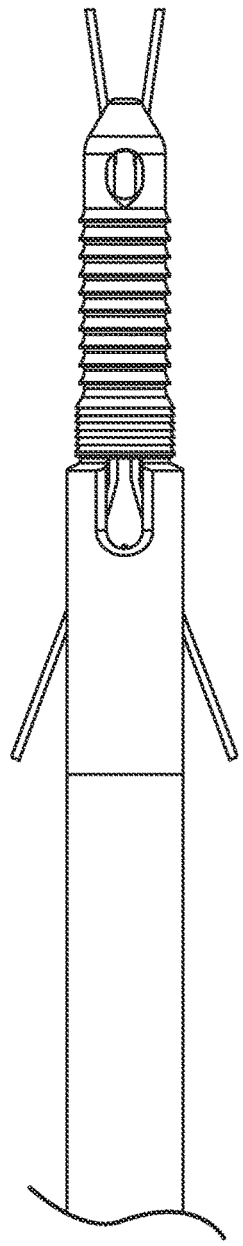
FIGS. 17-19 are a sequence of detail top views illustrating the sequence of FIGS. 14-16.
Figure 18:
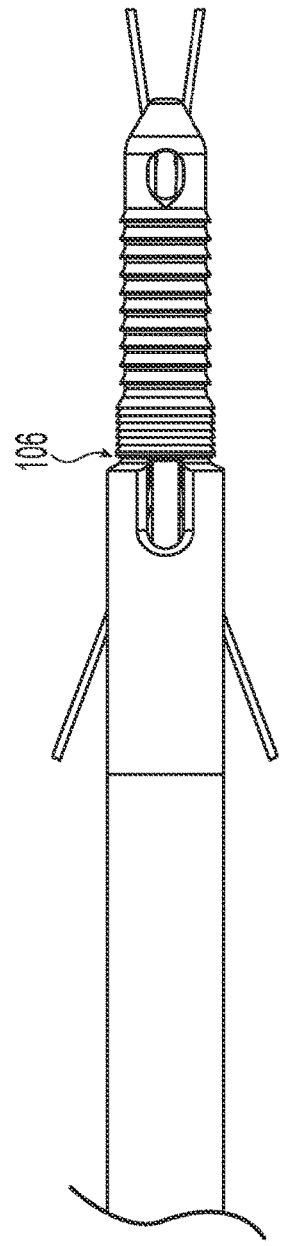
Figure 19:
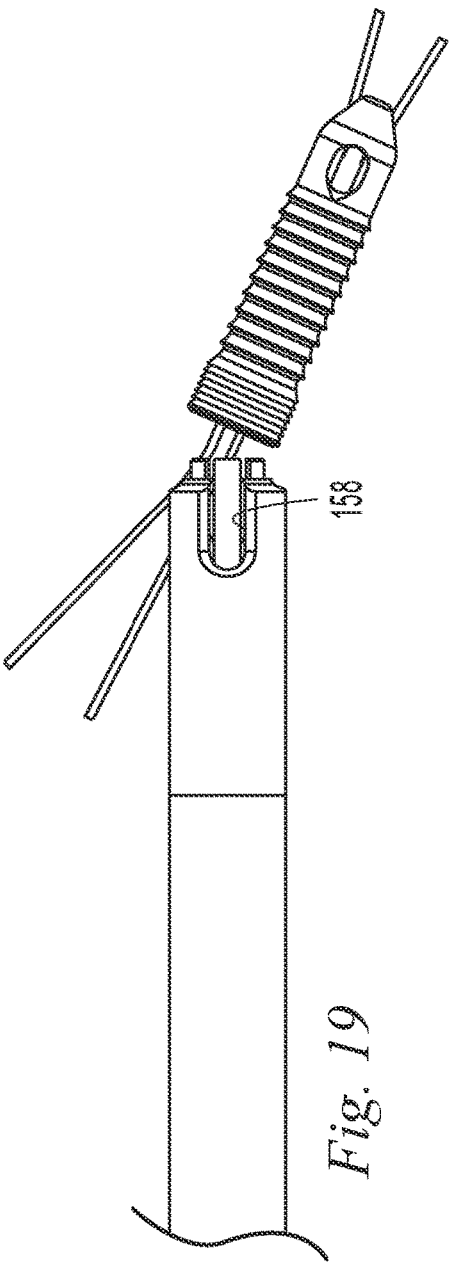

In FIG. 15, the advancement mechanism 214 has been operated to advance the pushrod 208 so that it has pushed the suture locking member 160 out of the proximal member 104 and into the anchor body 102 to secure the suture limbs 220, 222 within the anchor body 102. Preferably, the first portion 210 of the pushrod 208 extends sufficiently far distally from the second portion 212 of the pushrod 208 that the suture locking member 160 is fully inserted into the anchor body 102 before the second portion 212 of the pushrod begins to transmit axial force through the retainer 180 to the proximal end 108 of the anchor body 102. Once the suture locking member 160 is fully inserted, further operation of the advancement mechanism 214 presses the second portion 212 of the pushrod against the retainer 180 which presses against the anchor body 102 causing anchor body 102 to separate from the proximal member 104 at the frangible connection 106 as shown in FIG. 16. Separation of the members transforms the "U"-shaped openings 158, 159 of the proximal member 104 into distally open "U"-shaped slots that will release the suture limbs 220, 222 sideways out of the slots without the need for the ends of the suture limbs to be pulled through the openings 158, 159. In this way, the suture limbs 220, 222 will be released from the proximal member 104 even if the ends of the suture limbs 220, 222 are attached at another location or otherwise inaccessible.

Figure 20:
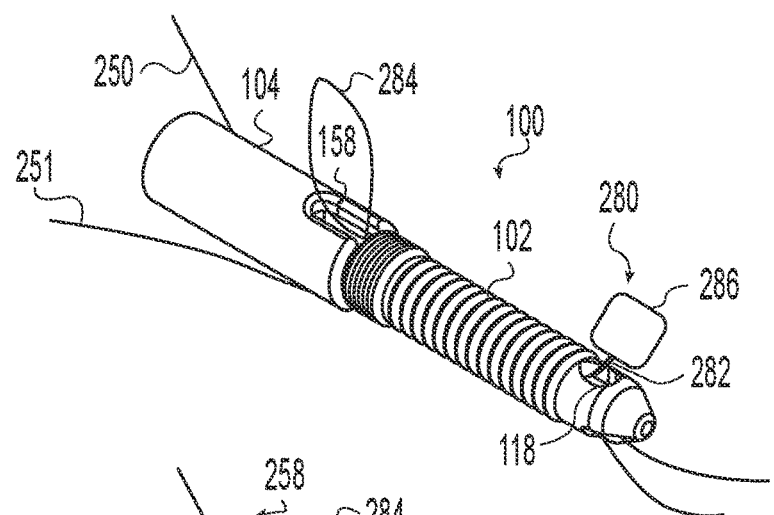
FIGS. 20-22 are a sequence of perspective views illustrating the threading of suture through the implant of FIG. 1 according to one embodiment.
Figure 21:
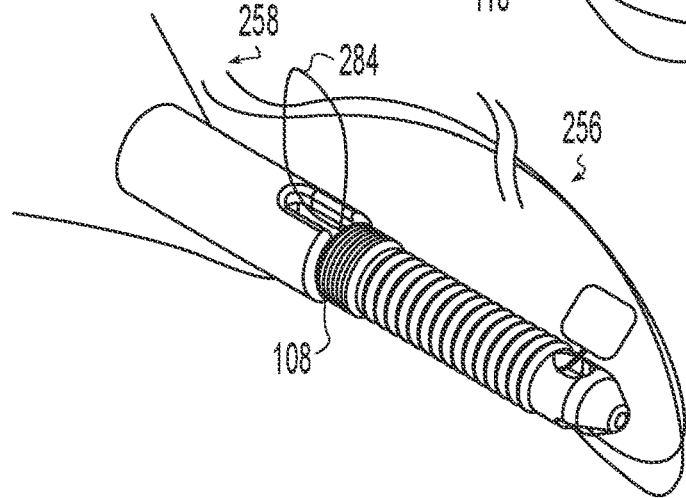
Figure 22:
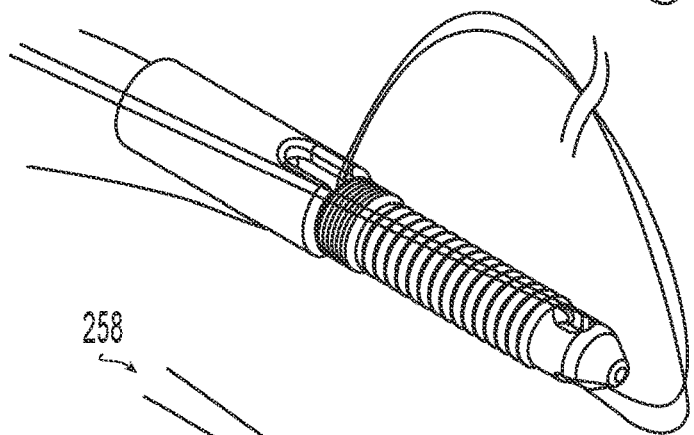
Figure 23:
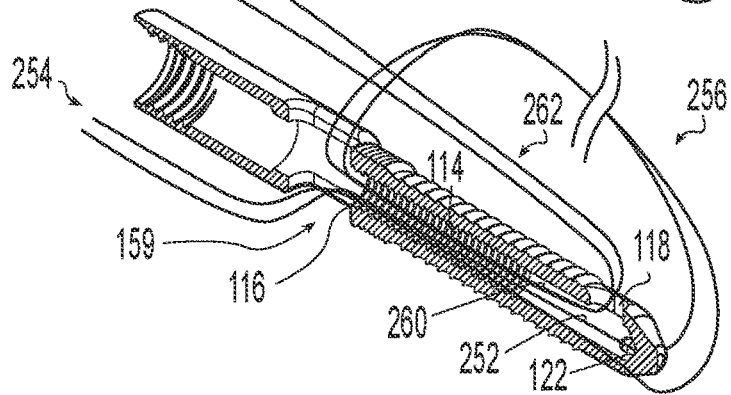
FIG. 23 is a perspective section view illustrating the suture and implant after threading the suture according to the example of FIGS. 20-22.

FIGS. 20-23 depict an illustrative example of a suture routing through the suture anchor 100. A suture threader 280 is pre-loaded into the anchor body 102. The suture threader includes a filament 282 forming a distal loop portion 284 and a proximal grip portion 286 joined to the loop portion. The suture threader 280 is inserted through the longitudinal passageway of the anchor body from the superior distal opening 118 to the proximal opening 116 with at least part of the loop portion 284 extending up and out of the superior "U"-shaped opening 158 of the proximal member 104 and the grip portion 286 extending out of the distal opening 118. In the illustrative example of FIGS. 20-23, two sutures 250, 251 are depicted. Any number of sutures may be utilized in accordance with the present disclosure and each of the depicted sutures may represent multiple sutures that are routed together. For simplicity, the suture locking member 160 and retainer 180 have been omitted from FIGS. 20-23 and the routing of only one suture 250 of the illustrated sutures will be described in detail. The suture 250 is threaded through an inferior distal opening 122 of the anchor body 102, with a first portion 252 extending through the longitudinal passageway 114 of the anchor body 102 between the proximal opening 116 and the distal opening. A proximal end 254 of the suture 250 extends out the proximal opening 116 of the anchor body 102 and down through the inferior "U"-shaped slot 188 of the retainer 180 (not shown) and the inferior "U"-shaped opening 159 of the proximal member 104. In FIG. 21, a second portion 256 of the suture 250 contiguous to the first portion 252 extends away from the anchor body 102. A distal end 258 of the suture 250 is inserted through the loop portion 284 of the threader 280. The threader 280 is pulled distally through the anchor body 102 to route the distal end 258 of the suture 250 back through the anchor body 102 so that a third portion 260 of the suture contiguous to the second portion 256 extends within the longitudinal passageway 114 between the proximal opening 116 and the superior distal opening 118. The distal end 258 of the suture is then pulled proximally so that a fourth portion 262 of the suture contiguous to the third portion 260 extends along the exterior surface of the anchor body 102 between the distal opening 118 and the proximal end 108. The suture locking member 160 may then be inserted into the anchor body to secure the first portion 252 of the suture and the third portion 260 of the suture within the longitudinal passageway by compressing the suture portions between the suture locking member 160 and the anchor body 102. For example, the suture may be compressed between the sides of the suture locking member and the interior sidewall of the anchor body as shown in FIGS. 15 and 16. In an example according to the present disclosure, the suture 250, 251 and threader may be provided preloaded to the anchor as shown in the configuration of FIG. 20.

FIGS. 24-31 illustrate a suture keeper 300 for managing the suture anchor 100 and sutures in storage and use. Referring to FIG. 24, the suture anchor 100 is prepared as in FIG. 20 with the threader 280 inserted into the suture anchor 100 with the grip portion 286 extending out of the superior distal opening 118 and the loop portion 284 extending out of the superior "U"-shaped opening 158. Four suture strands are loaded in the suture anchor. Preferably each suture strand is uniquely identifiable such as by color, pattern, or otherwise. A first pair of suture strands 310, 311 extends through the longitudinal passageway 114 with proximal ends 312, 313 extending from the inferior "U"-shaped opening 159 and distal ends 314, 315 extending from the first inferior distal opening 120. A second pair of suture strands 320, 321 extends through the longitudinal passageway 114 with proximal ends 322, 323 extending from the inferior "U"-shaped opening 159 and distal ends 324, 325 extending from the second inferior distal opening 122.

Referring to FIG. 25, the suture keeper 300 includes an elongate, generally planar body 330 extending from a proximal end 332 to a distal end 334 and having a length 336 between the proximal and distal ends 332, 334 and a width 338 between first and second sides 326, 328. A first slot 340 formed in the body 330 defines a first, proximal, cantilevered tab 342 free at its distal end 344. Preferably the first slot 340 is narrower than the suture anchor 100 so that the suture anchor can lie in the first slot 340 without passing through the first slot 340. A second slot 346 defines a second, distal, cantilevered tab 348 free at its proximal end 350. Four holes are formed through the body 330 adjacent the first slot 340 with a first pair of holes 352, 354 adjacent a side of the first slot 340 nearer the first side 326 of the body 330 and a second pair of holes 356, 358 adjacent an opposite side of the first slot 340 nearer the second side 328 of the body 330. First and second spaced apart proximal notches 360, 362 are formed into the proximal end 332 of the body 330 with the notches 360, 362 being nearer the first and second sides 326, 328 of the body 330 respectively. First and second spaced apart distal notches 364, 366 are formed into the distal end 334 of the body 330 with the notches 364, 366 being nearer the first and second sides 326, 328 of the body respectively. First and second spaced apart distal slits 368, 369 are formed in the distal end 334 of the body 330 with the slits 368, 369 being nearer the first and second sides 326, 328 of the body respectively. Preferably the distal slits 368, 369 are located between the distal notches 364, 366. In the illustrative example of FIG. 25, the suture keeper is made from a thin, flexible sheet of material.

Figure 27:
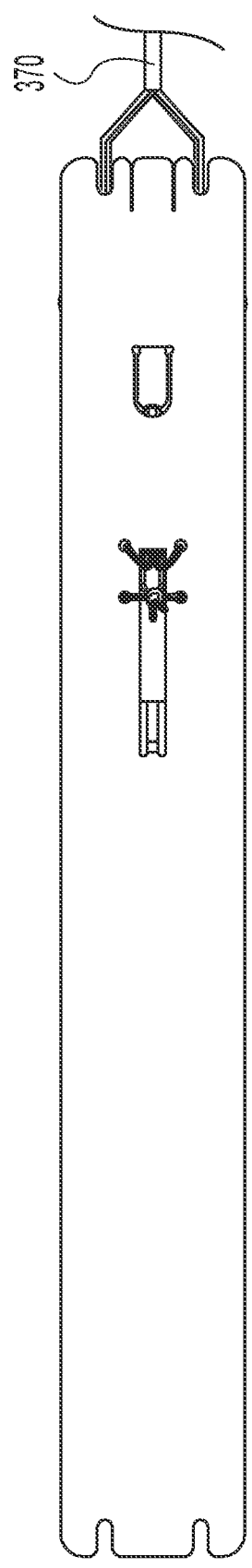

Referring to FIG. 26, a tube 370 is placed over the distal ends of the suture strands of the suture anchor 100 of FIG. 24. Optionally, the tube may be a dual lumen tube so that each pair of suture strands passes through a separate lumen in the tube further isolating the first and second pairs from one another. Preferably, the tube 370 is frangible so that it may be torn from the sutures. For example, a thin walled tube 370 may be torn along its length to split the tube and remove it laterally away from the sutures. One or more starter notches may be formed in the sidewall at one or both ends to facilitate tearing the tube. The proximal ends 312, 313, 322, 323 of the first and second suture pairs are passed through the first slot 340. The proximal ends 312, 313 of the first suture pair is passed through the distal most hole 354 of the first pair of holes and then through the proximal most hole 352 of the first pair of holes. The proximal ends 322, 323 of the second suture pair is passed through the distal most hole 356 of the second pair of holes and then through the proximal most hole 358 of the second pair of holes. The proximal ends 312, 313, 322, 323 are all tied together to join them to the suture keeper 300 (FIG. 27). Thus joined, the suture keeper prevents the proximal ends from being pulled back into the suture anchor 100. The suture anchor 100 is mounted on the suture keeper 300 by bending the proximal and distal tabs 342, 348 upwardly and inserting the suture anchor 100 into the first slot 340 between the tabs with the proximal tab 342 pressing against the proximal end 152 of the proximal member 104 and the distal tab 348 pressing against the distal end 110 of the anchor body 102 to releasably hold the suture anchor 100. The first pair of suture strands 310, 311 is positioned in the first distal notch 364 and the second pair of suture strands 320, 321 is positioned in the second distal notch 366.

FIG. 27 is a rear view of the configuration of FIG. 26.

Figure 28:
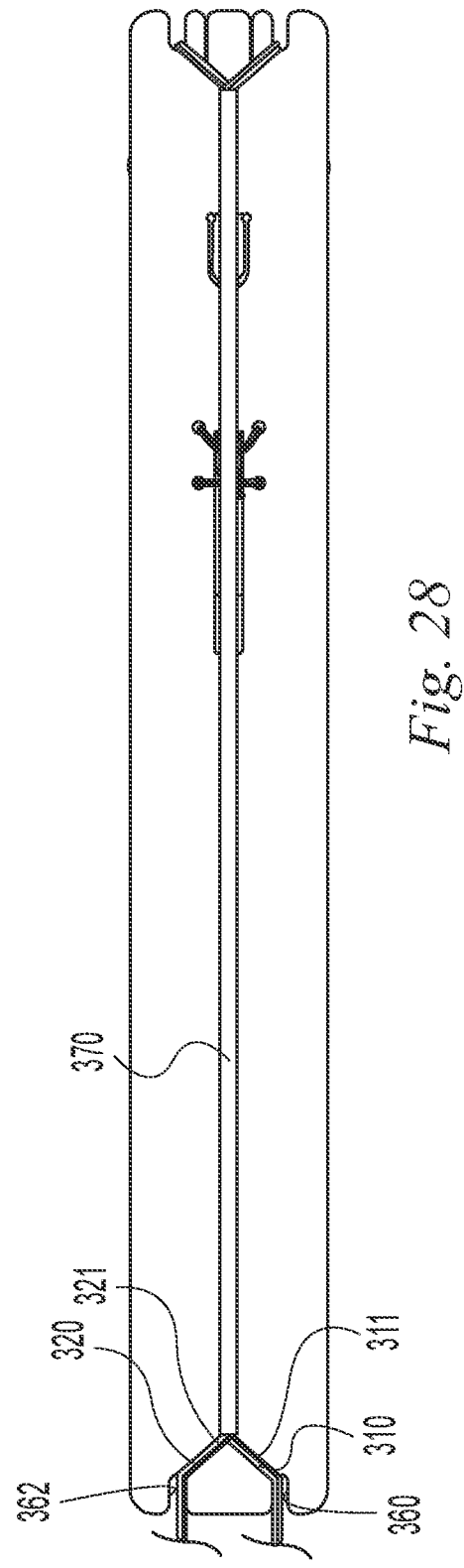

Referring to FIG. 28, the suture strands are folded back through the distal notches so that the suture strands and tube 370 lie along the back of the suture keeper 300. The first pair of suture strands 310, 311 is positioned in the first proximal notch 360 and the second pair of suture strands 320, 321 is positioned in the second proximal notch 362.

Figure 29:
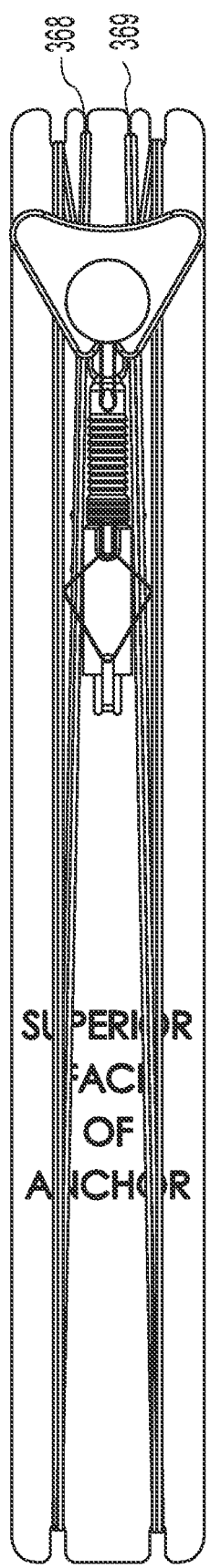

Referring to FIG. 29, the suture strands are wrapped around the suture keeper 300 between the proximal and distal notches as many times as necessary to contain the length of the suture strands while keeping the first pair of strands together on the first side and the second pair of strands together on the second side. The ends of the sutures are pulled into the slits 368, 369 to secure the sutures to the suture keeper 300.

Figure 30:
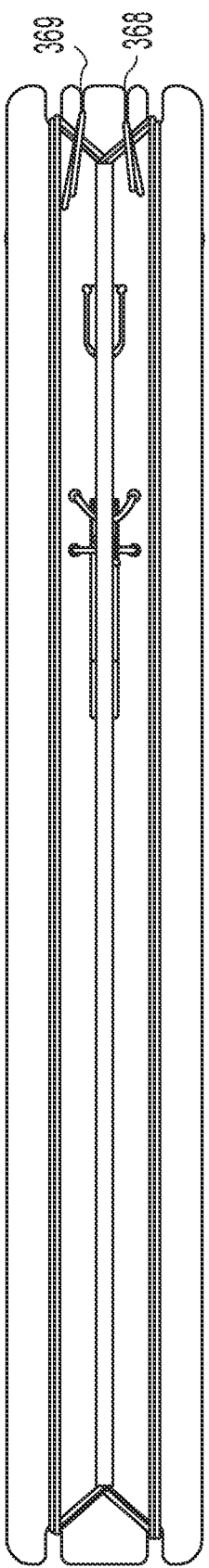

FIG. 30 is a rear view of the configuration of FIG. 29.

Figure 31:
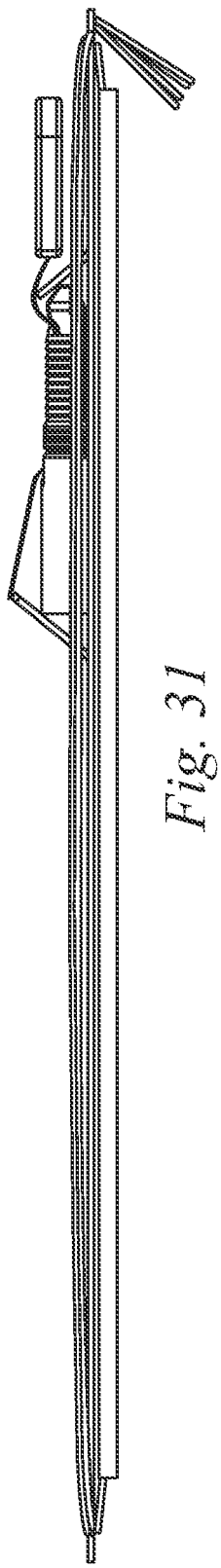

FIG. 31 is a side view of the configuration of FIG. 29.

FIGS. 32-41 illustrate a transosseous surgical repair method using the components illustrated in FIGS. 1-31. The illustrative method of FIGS. 32-41 depicts a rotator cuff repair. However, the implants, instruments, and method illustrated may be used to form transosseous attachments at other locations and for other purposes.

Figure 32:
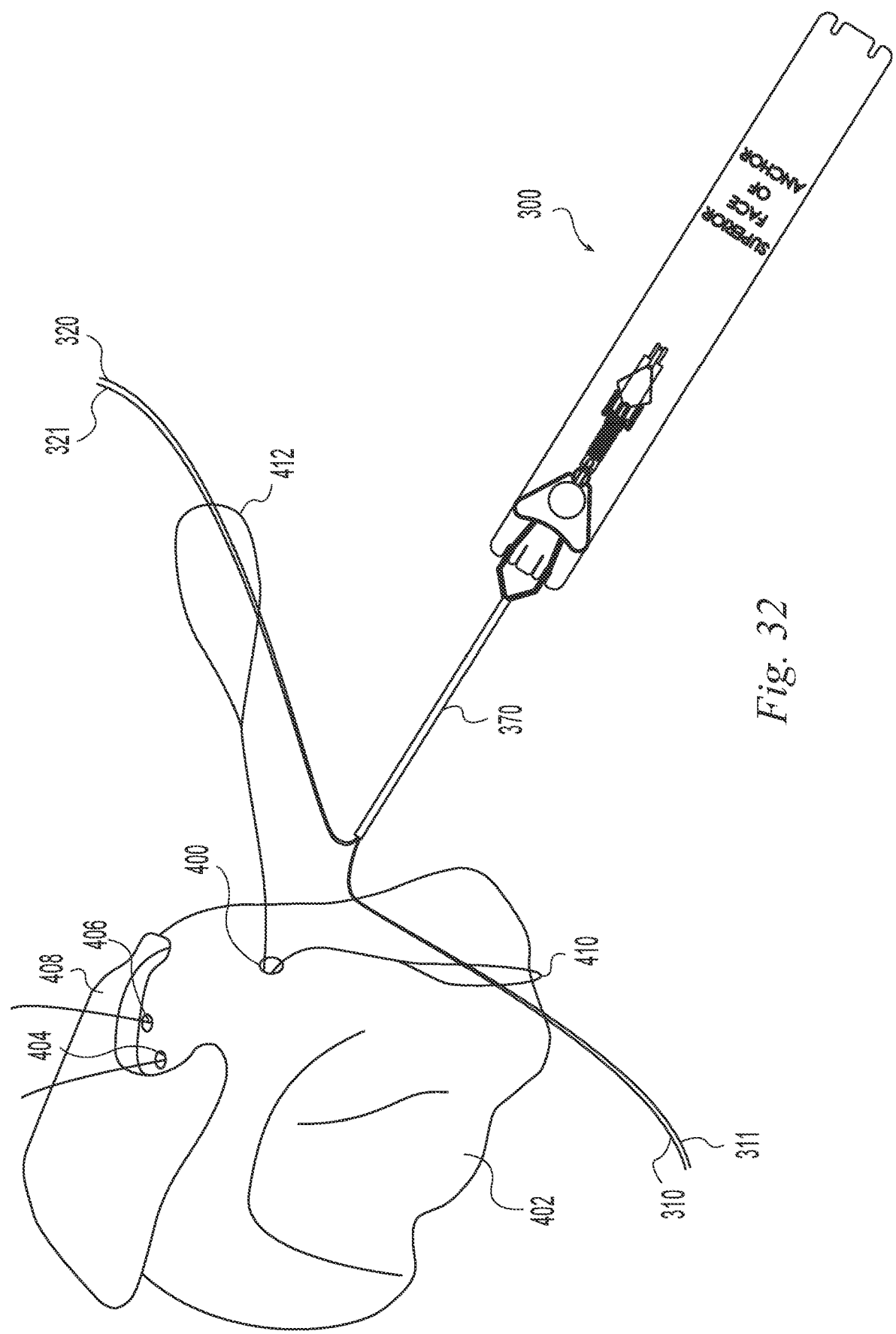
FIGS. 32-41 are a sequence of perspective views illustrating a transosseous surgical repair technique according to one embodiment.

Referring to FIG. 32, a lateral tunnel 400 has been formed into a humerus 402. First and second medial tunnels 404, 406 have been formed into the humerus 402. The medial tunnels 404, 406 are spaced apart at the surface of the bone near the rotator cuff 408 and the medial tunnels 404, 406 intersect the lateral tunnel 400 inside the humerus 402. First and second suture shuttles 410, 412 are inserted into the medial tunnels 404, 406 and exit the bone through the lateral tunnel 400. The sutures are unwound from the suture keeper and the first pair of suture strands 310, 311 is engaged with the first suture shuttle 410 and the second pair of suture strands 320, 321 is engaged with the second suture shuttle 412. By utilizing the suture keeper 300 to manage the sutures, the various strands of sutures may be easily isolated to prevent tangling and to facilitate independent manipulation of a desired suture strand. The tube 370 may be positioned within a surgical portal (not shown) and acts to confine the suture strands to prevent them from entangling one another and/or instruments and other items passed through the portal.

Figure 33:
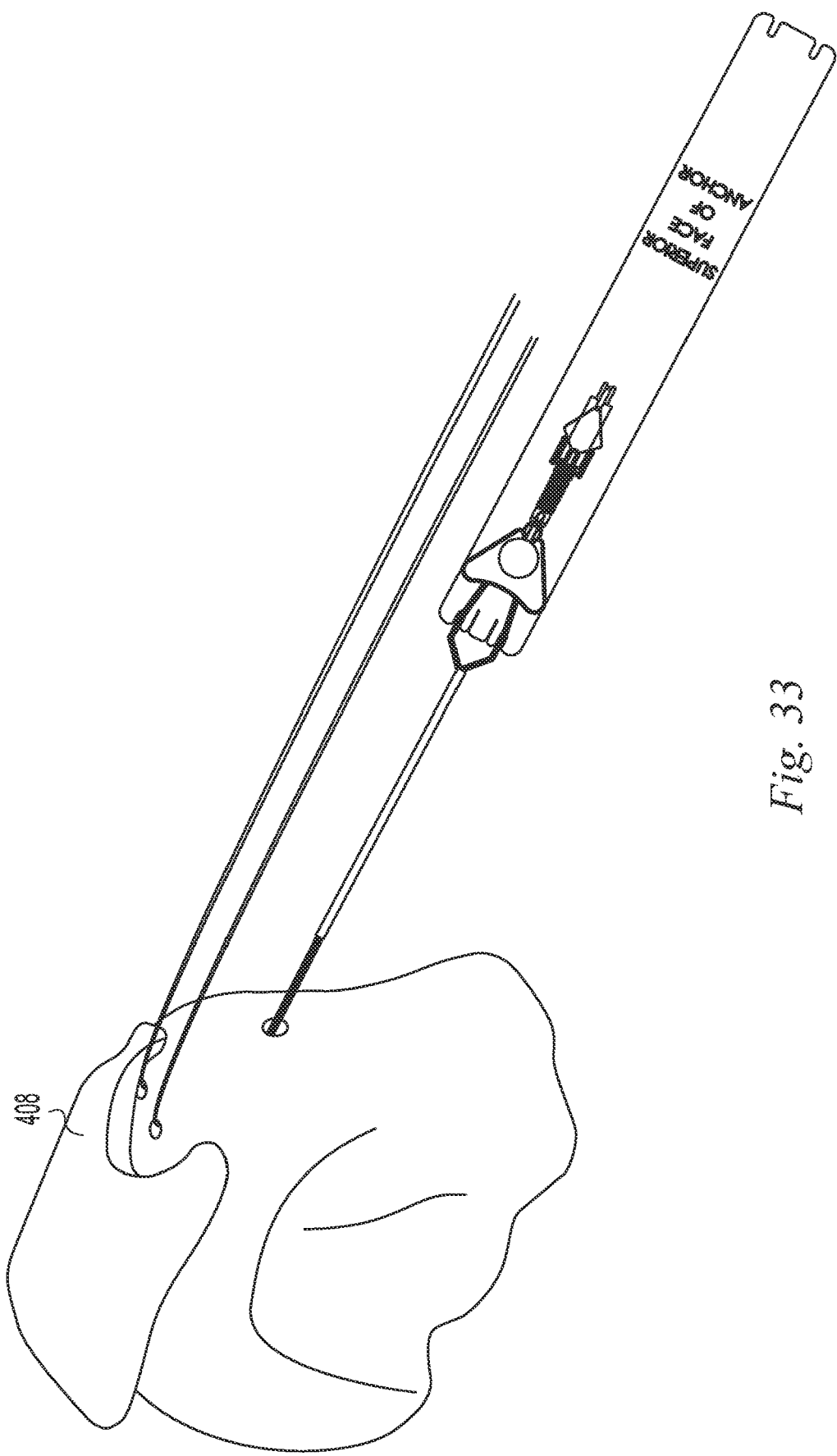

Referring to FIG. 33, the suture shuttles 410, 412 have been pulled to shuttle the suture strands through the bone tunnels.

Figure 34:
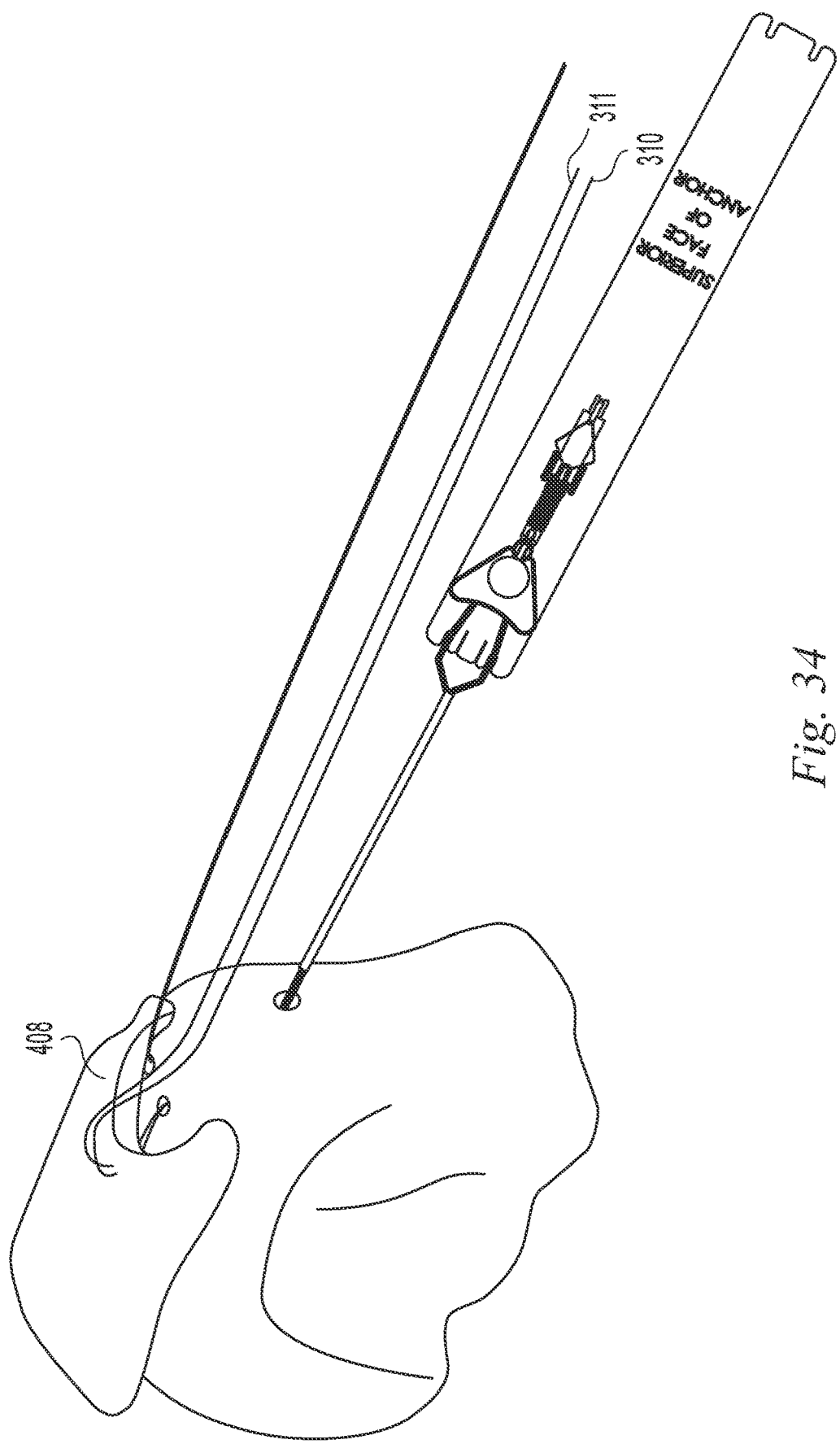

Referring to FIG. 34, the first pair of suture strands 310, 311 has been passed through the rotator cuff 408.

Figure 35:
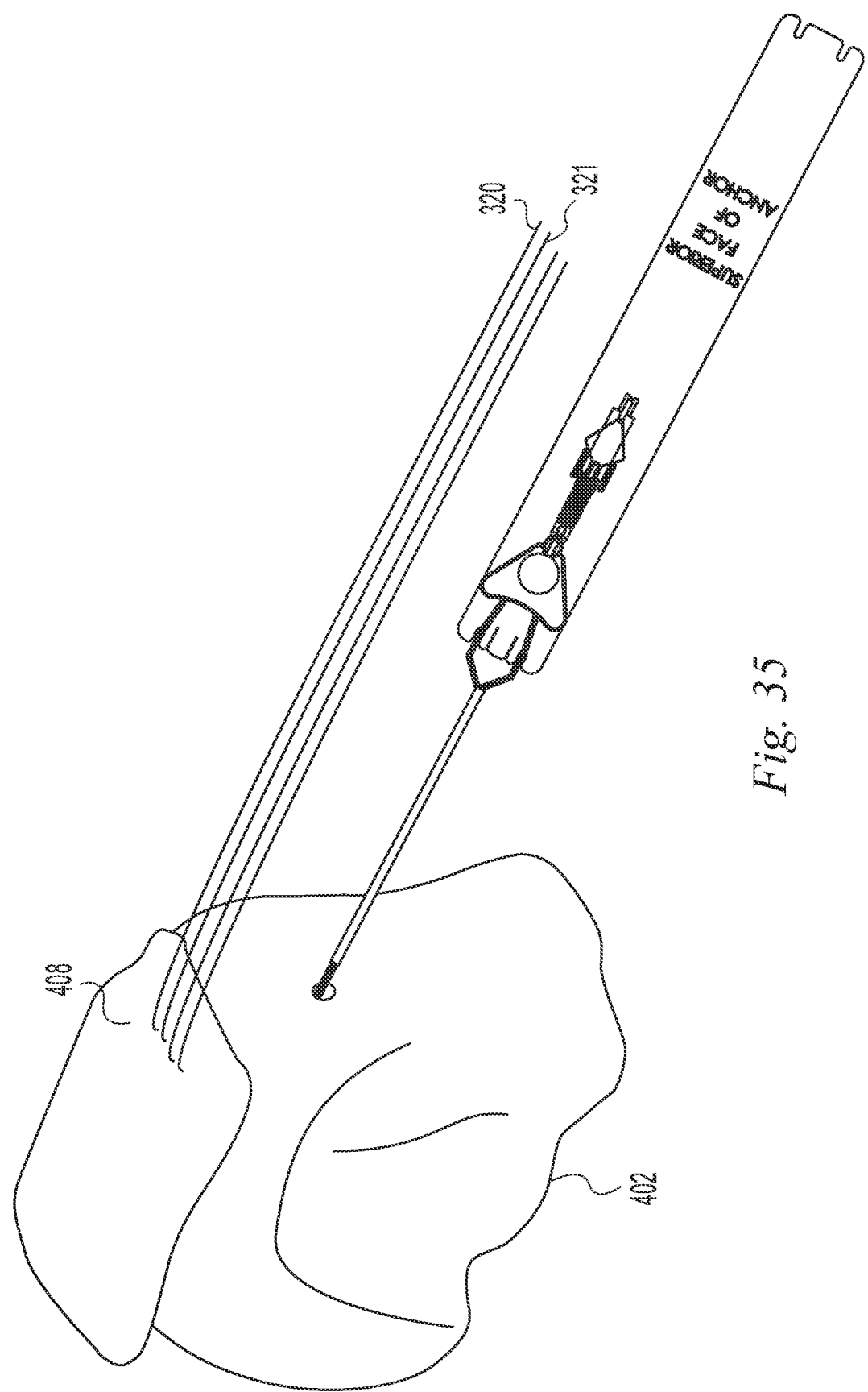

Referring to FIG. 35, the second pair of suture strands 320, 321 has been passed through the rotator cuff 408 and the rotator cuff 408 has been repositioned to a desired lateral margin of the humerus.

Figure 36:
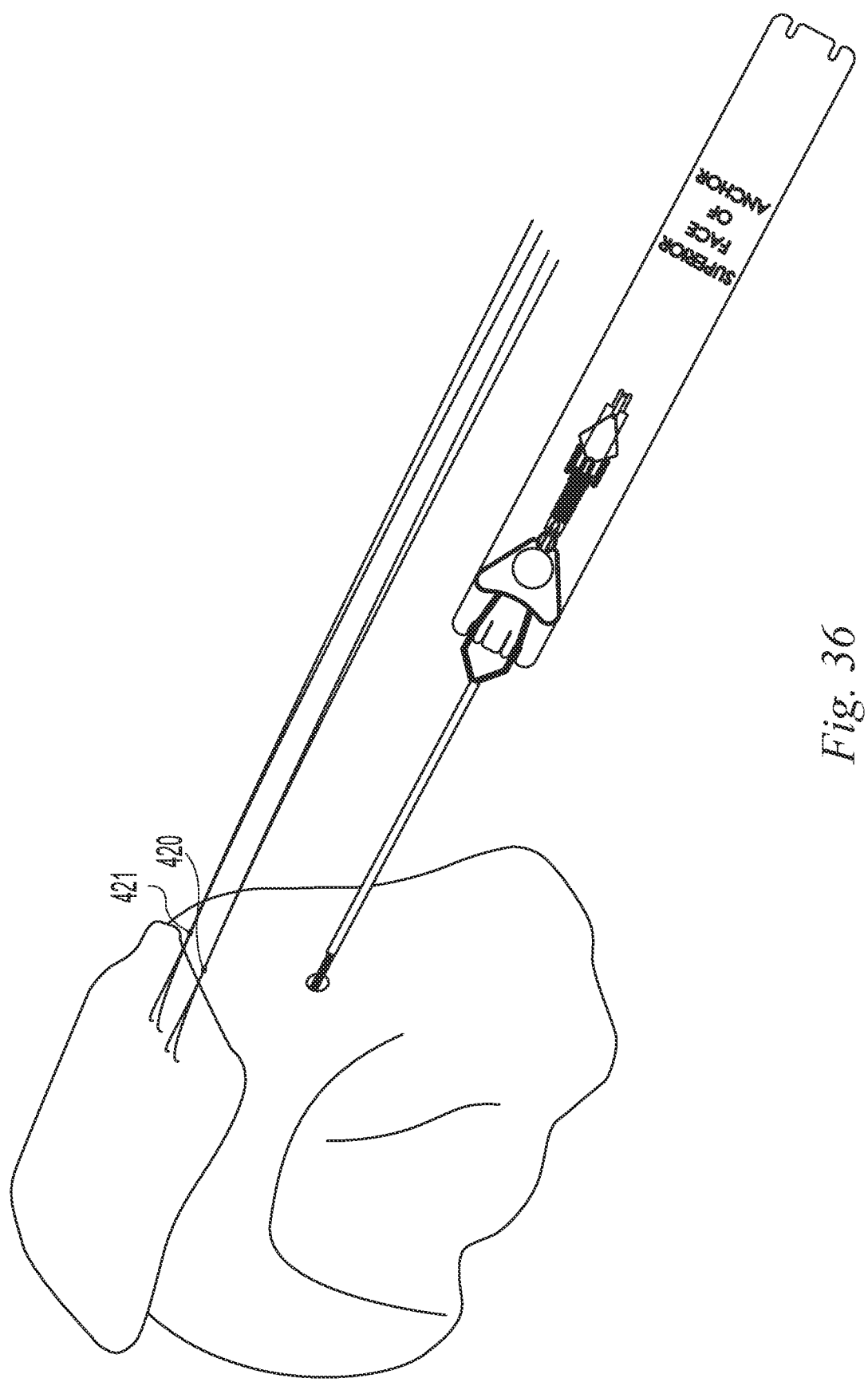

Referring to FIG. 36, a simple overhand knot 420, 421 has been tied in each suture pair. This may be done easily outside the cannula, outside of the patient's body without the need for arthroscopic knot tying techniques.

Figure 37:
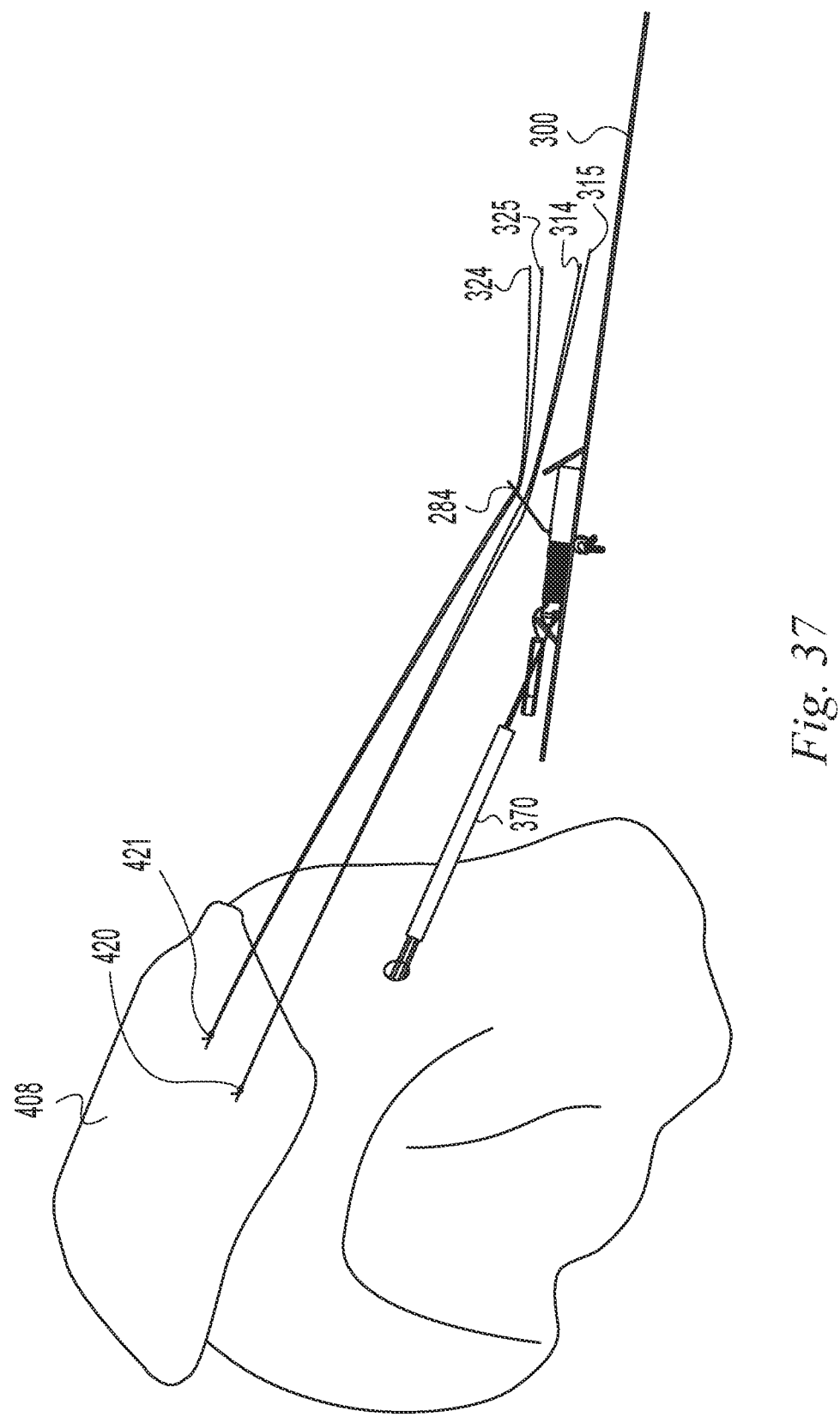

Referring to FIG. 37, the proximal portions of the sutures may be pulled to move the knots 420, 421 into the patient to a position adjacent to the rotator cuff 408. Since the suture strands have been kept separate by the suture keeper 300 and the surgical technique, the knots 420, 421 may be independently positioned and tensioned to provide precise control over the final position and tension of the rotator cuff 408. The distal ends 314, 315, 324, 325 of the suture pairs are passed through the loop 284 of the suture threader 280.

Figure 38:
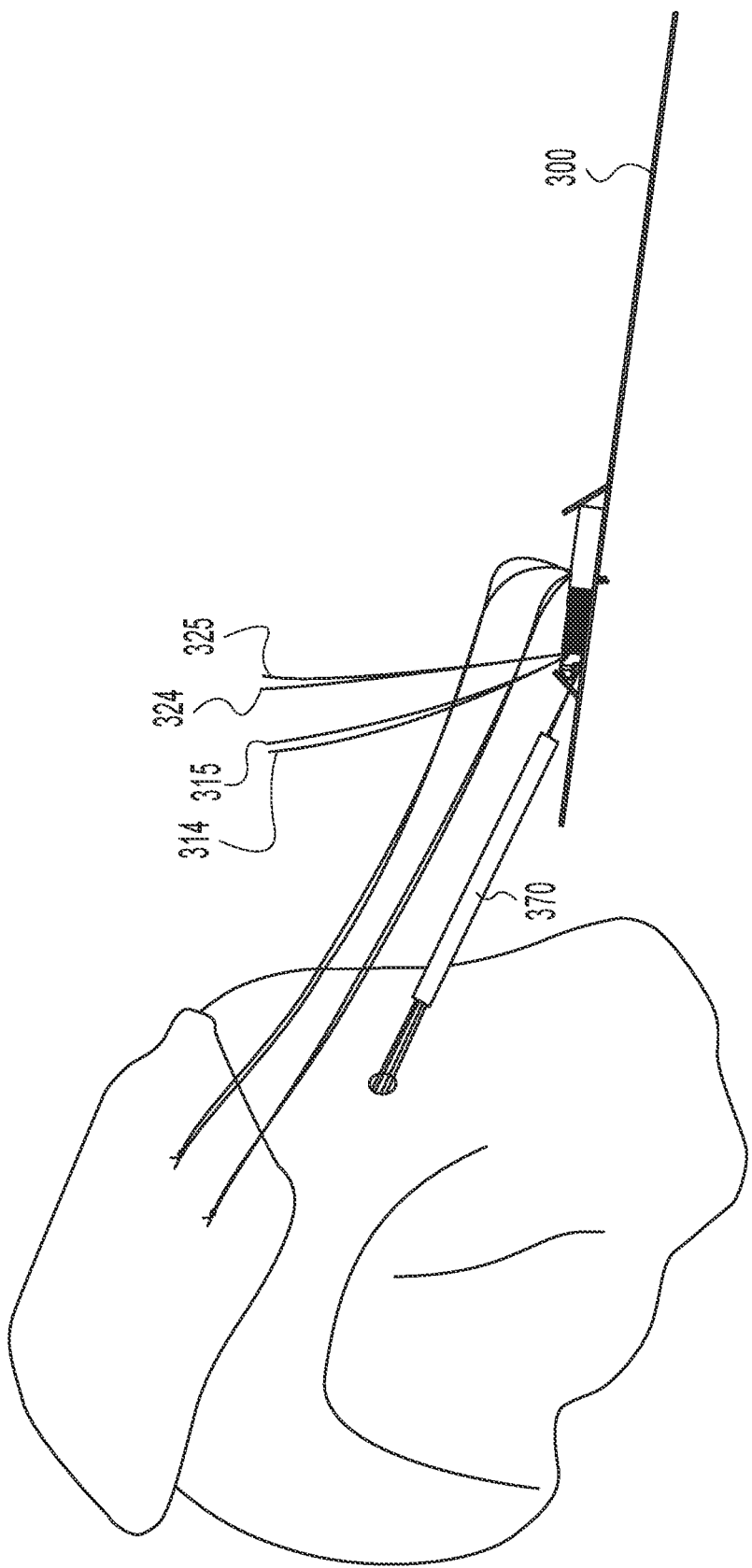

Referring to FIG. 38, the suture threader 280 is pulled out the distal end of the suture anchor 100 to thread the suture strands back through the suture anchor 100 as shown in FIGS. 20-23. The protective tube 370 is split and removed laterally away from the sutures.

Figure 39:
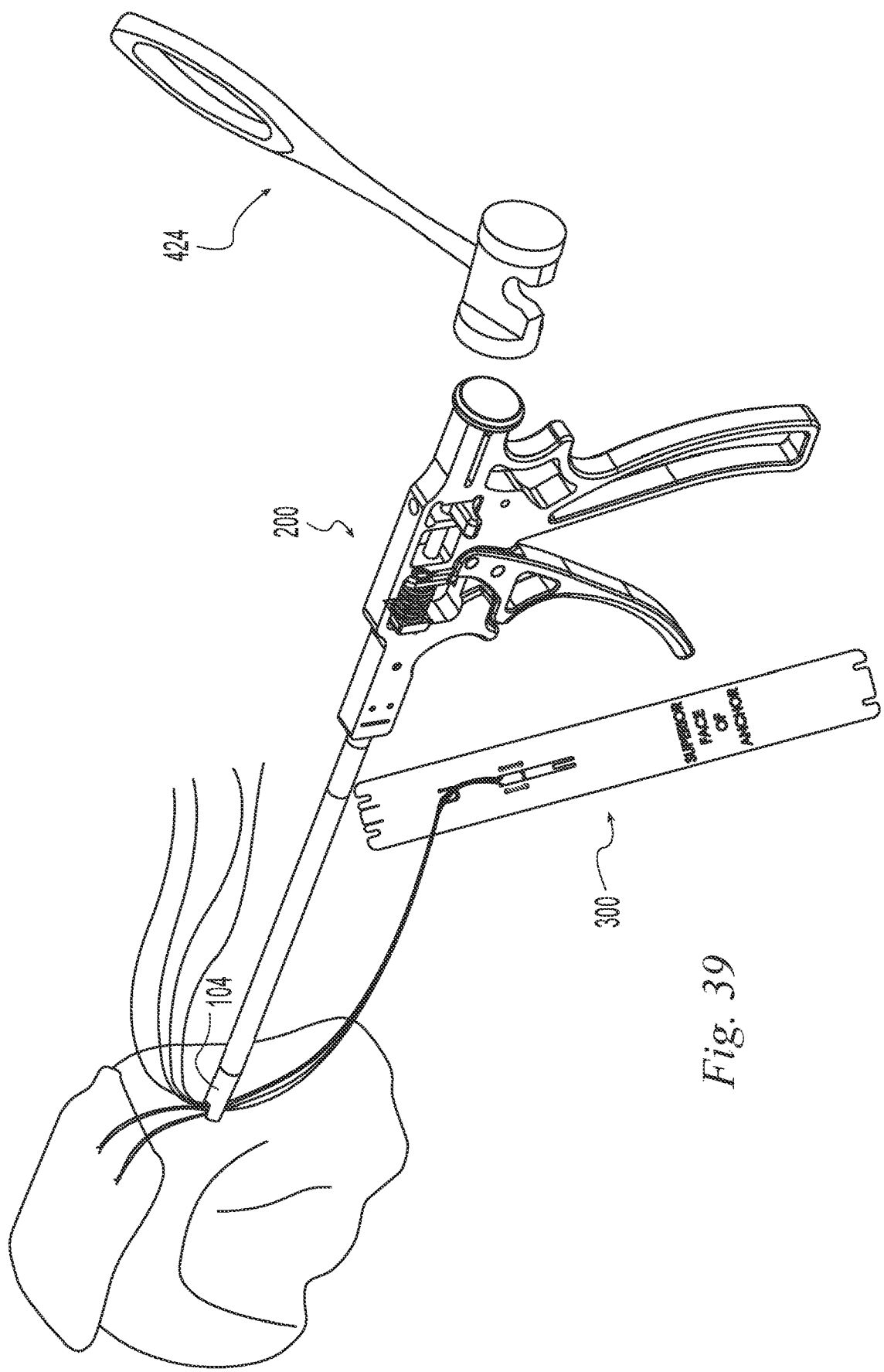

Referring to FIG. 39, the inserter 200 is engaged with the proximal member 104 of the suture anchor 100. Any slack in the suture strands may be pulled through the suture anchor 100 by pulling on the proximal ends of the suture strands retained by the suture keeper 300. The suture anchor 100 is inserted into the lateral bone tunnel 400. A mallet 424 may be used to impact the end of the inserter 200 to urge the suture anchor into the lateral bone tunnel 400.

Figure 40:
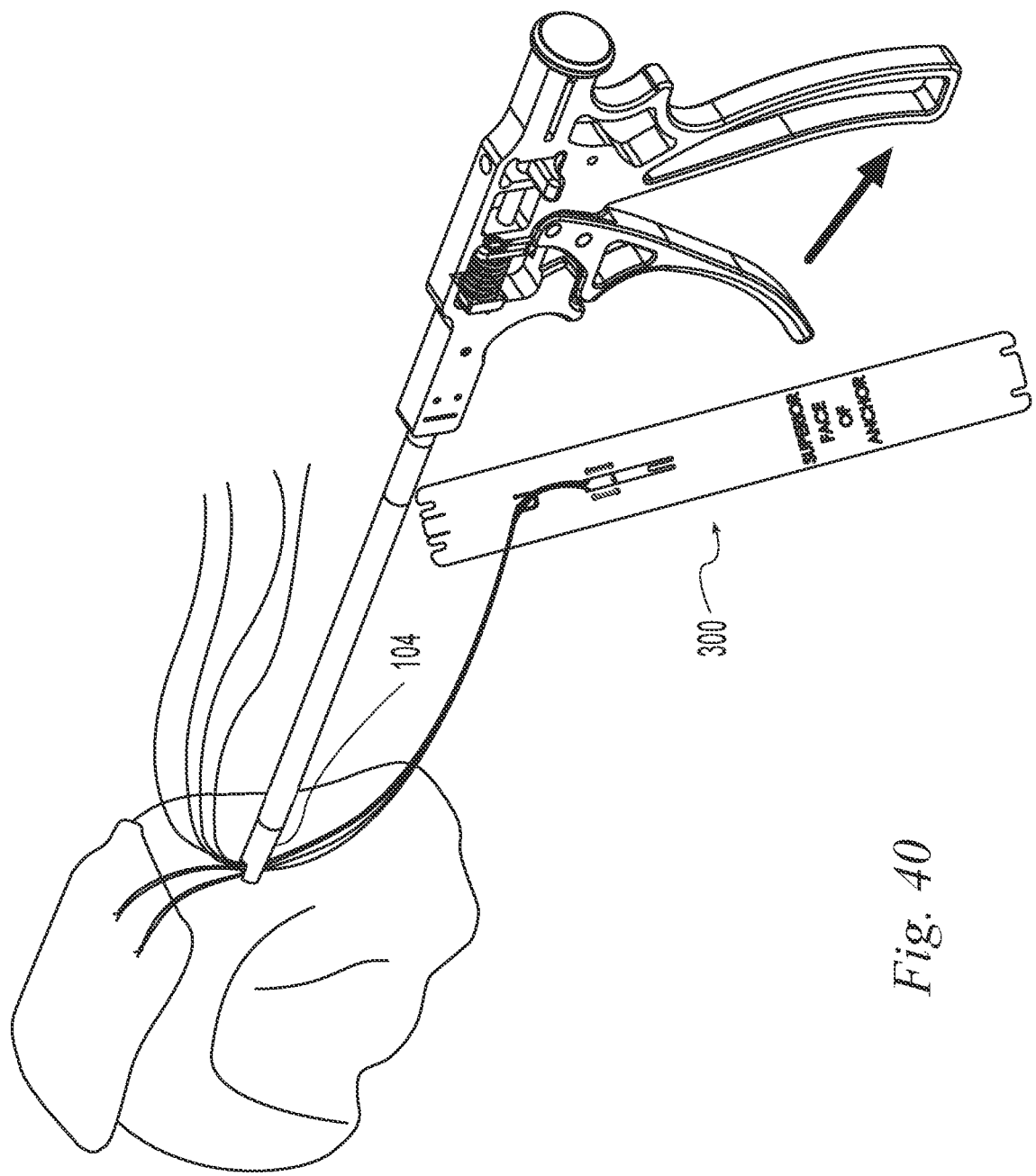

Referring to FIG. 40, the distal portions of the suture strands have passed through the anchor body twice and have been pulled back proximally along the outside of the anchor body so that they are compressed between the anchor body and the bone tunnel wall. The proximal portions of the sutures have passed through the anchor body once, exited outwardly through the inferior distal openings, and then been pulled superiorly through the medial tunnels. This suture routing provides sufficiently low friction that the friction may be overcome by a user to independently pull each suture strand through the anchor body 102 to adjust the position and tension of the soft tissue yet sufficiently high friction that when the suture strands are released the imparted position and tension are maintained so the user can evaluate the repair and determine if further adjustments are needed. The inserter 200 may be used to provide an axial counterforce to keep the anchor body 102 in the bone tunnel while adjustments are made. Once the sutures are adjusted as desired, the inserter 200 is actuated to press the suture locking member 160 into the suture anchor 100 and secure the sutures to the suture anchor 100. The inserter 200 is further actuated to press the retainer 180 against the proximal end of the anchor body 102 and separate the proximal member 104 from the anchor body 102. When the proximal end 104 separates from the anchor body 102, the "U"-shaped openings 158, 159 transform into distally opening slots and the sutures release distally from the slots as the proximal end 104 is pulled away from the bone.

If desired, the proximal ends 312, 313, 322, 323 of the suture strands may be separated from the suture keeper 300, such as by cutting the sutures, and the ends of the sutures may be passed through the soft tissue to form adjunctive stitches to further anchor the soft tissue. The proximal suture ends are preferably used since any loads carried by the proximal suture ends only act perpendicularly on the proximal end of the anchor and thus, they do not exert a significant axial force tending to dislodge the anchor body from the lateral tunnel 400.

Figure 41:
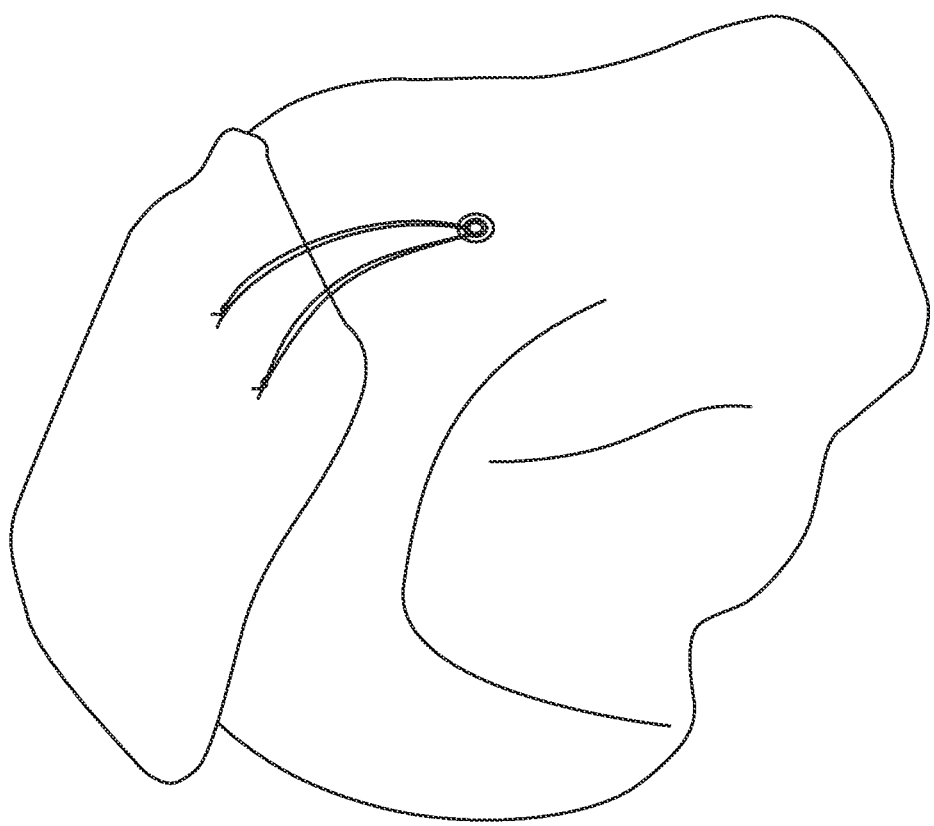

Referring to FIG. 41, any remaining suture ends are trimmed.

FIGS. 42-48 depict a suture anchor 500 according to an example of the present disclosure. The suture anchor 500 is the same as the suture anchor 100 of the example of FIGS. 1-12 except for the configuration of the distal openings. The anchor 500 has an anchor body 502, a proximal member 504 joined to the anchor body 502 by a frangible connection 506 and a suture locking member 560 all configured as in the example of FIGS. 1-12. The anchor body 502 is generally cylindrical and has a sidewall 503 defining an exterior surface, a proximal end 508, a distal end 510, and a longitudinal axis 512 extending between the proximal and distal ends 508, 510. An interior longitudinal passageway 514 extends at least partway from the proximal end 508 toward the distal end 510. A proximal opening 516 communicates through the proximal end 508 of the anchor body 502 along the axis 512 with the interior longitudinal passageway 514. The distal opening comprises a plurality of distal openings that communicate from the exterior surface of the anchor body 502 through the sidewall 503 to the interior longitudinal passageway 514. In the illustrative example of FIGS. 42-48, the distal openings include a first, more proximal superior opening 518 and a second, more distal superior opening 520. The first and second distal openings 518, 520 are formed through the sidewall 503 to communicate with the interior longitudinal passageway 514 and are centered over the longitudinal axis 512 on the same side of the anchor body. The first and second distal openings 518, 520 are spaced proximally away from the distal end 510 of the anchor body. In the example of FIGS. 42-48, the second opening 520 is elongated longitudinally and communicates with a proximally sloping passage 521 that connects it to the interior longitudinal passageway 514.

FIG. 49 depicts the anchor 500 of FIGS. 42-48 preloaded with first and second suture threaders 600, 610. The first threader 600 includes a proximal grip portion 604 and a filament forming a distal loop portion 602 joined to the grip portion. The first threader includes a semi-circular clip 606 sized to snap onto the anchor body to releasably secure the threader to the anchor body. The first suture threader 600 is engaged with the anchor by inserting the distal loop portion 602 through the inferior "U"-shaped opening 559 of the proximal member 504, through the proximal opening 516, along the longitudinal passageway 514, and out through the second superior opening 520. The grip portion is clipped to the anchor body. The second threader 610 includes a proximal grip portion 614 and a filament forming a distal loop portion 612 joined to the grip portion. The second threader includes a pair of semi-circular clips 616, 618 sized to snap onto the anchor body to releasably secure the threader to the anchor body. The second suture threader is engaged with the anchor by inserting the distal loop portion 602 through the first superior opening 518, along the proximally sloping passage 521, along the longitudinal passageway 514, through the proximal opening 516, and out the superior "U"-shaped opening 558 of the proximal member 504. The grip portion is clipped to the anchor body with the second suture threader clips 616, 618 straddling the first suture threader clip 606.

In the example of FIG. 49 the threaders are labeled to facilitate their use in a procedure to attach, for example, a tendon to a bone. The first suture threader 600 is labeled with a "1" and the message "TUNNEL SUTURES" to indicate that it is used, preferably first, to thread sutures extending from the bone tunnel in which the anchor will be seated through the anchor. The second suture threader 610 is labeled with a "2" and the message "TENDON SUTURES" to indicate that it is used, preferably second, to thread sutures extending from the soft tissue, tendon in this example, through the suture anchor.

FIG. 50 also depicts the anchor 500 of FIGS. 42-48 preloaded with first and second suture threaders 630, 610. In this example, the first threader 630 is extended and a tube 632, like the tube 370 of FIG. 26, is placed over the extended portion of the suture threader 630. The tube may, for example, be used to protect, confine, separate, or otherwise aid in suture management as previously described relative to the example of FIG. 26. In the example of FIG. 50, the proximal end of the tube includes an enlarged cylindrical portion 634 that is sized to press over the distal end of the anchor body to releasably join the tube 632 to the anchor. The distal loop portion 636 of the first threader extends out the distal end of the tube 632. As in the example of FIG. 26, the tube 632 is preferably frangible. For example, the tube is preferably longitudinally splittable.

FIGS. 49 and 50 are examples in which a suture anchor is provided for use without any sutures preloaded with the anchor. This provides maximum flexibility to the user to choose the type and number of sutures to be used and also allows for suture manipulation during the surgical procedure without the anchor potentially interfering with certain suture passing techniques. The threaders are pre-loaded to facilitate threading the sutures through the anchor once the sutures are selected and/or positioned in the bone and soft tissue. The configuration of the example of FIG. 49 is compact and may be more suitable for open or shallow minimally invasive surgical procedures. The configuration of the example of FIG. 50 may be more suitable for arthroscopic or otherwise deep surgical procedures in which suture management is more challenging.

Figure 51:
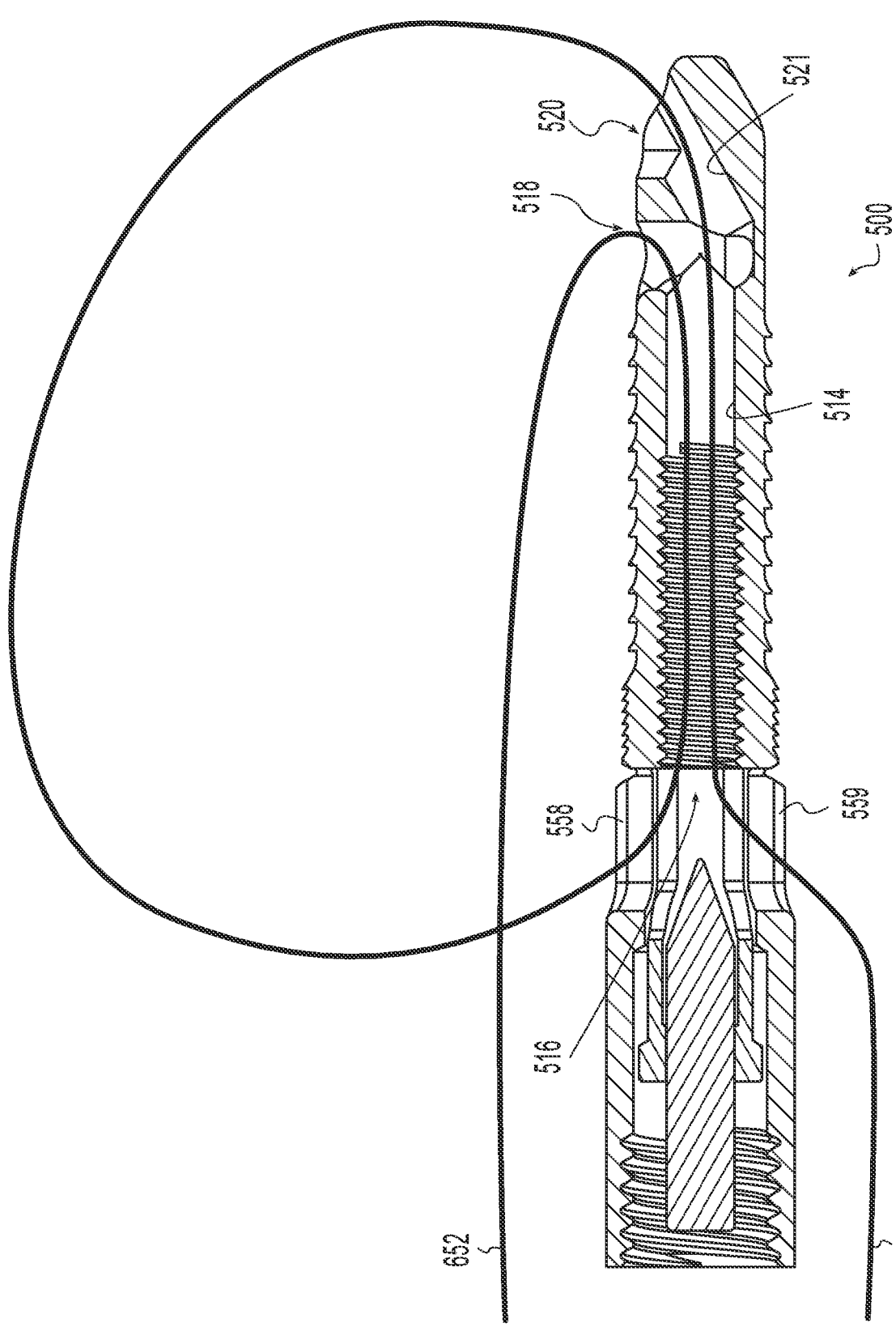
FIG. 51 is a side section view of the implant of FIG. 42 with a suture routed according to one embodiment.

FIG. 51 depicts an example of suture routing through the suture anchor 500 of FIGS. 42-48 such as for example using the threaders of FIG. 49 or 50. For example, in a transosseous soft tissue fixation procedure, one or more sutures may be extended through a bone tunnel with a first portion of the suture extending from a first opening of the bone tunnel and a second portion of the suture extending from a second opening of the bone tunnel. For example, in a rotator cuff repair procedure a first portion of suture may extend from a lateral opening of a tunnel formed in a humeral bone and a second portion of suture may extend from a medial opening at a desired attachment location for the soft tissue. The second portion may be passed through soft tissue, for example tissue of the rotator cuff, and extended away from the soft tissue.

The suture may be threaded through the anchor 500 using the suture threaders. In an example, the first portion of suture 650 is threaded through the distal loop portion 602 of the first suture threader 600. The grip portion 604 of the first suture threader is grasped and pulled to disengage the clip 606 from the anchor body and pull the first portion of suture 650 through the second superior opening 520 in the suture anchor body, proximally along the longitudinal passageway 514, through the proximal opening 516, and out through the inferior "U"-shaped opening 559. The second portion of suture 652 is threaded through the distal loop portion 612 of the second suture threader 610. The grip portion 614 of the second suture threader is grasped and pulled to disengage the clips 616, 618 from the anchor body and pull the second portion of suture 652 through the superior "U"-shaped opening 558, through the proximal opening 516, distally along the longitudinal passageway 514, and out through the first superior opening 518.

FIGS. 52-61 depict an illustrative example of a suture anchor 700. The suture anchor 700 has an anchor body 702, a proximal member 704 joined to the anchor body 702 by a frangible connection 706 and an interference member 770. The frangible connection may include, for example, a thin wall (as shown), a perforated section, an intermediate material such as an adhesive, and/or other suitable frangible constructions or structures.

In the illustrative example of FIGS. 52-61, the anchor body 702 is generally cylindrical and has a sidewall 750 (FIG. 61) defining an exterior surface, a proximal end 708, a distal end 710, and a longitudinal axis 712 extending between the proximal and distal ends 708, 710. An interior longitudinal passageway 714 extends at least partway from the proximal end 708 toward the distal end 710. A proximal opening communicates with the longitudinal passageway nearer the proximal end 708 and a distal opening communicates with the longitudinal passageway nearer the distal end 710. In the illustrative embodiment of FIGS. 52-61, the proximal opening 716 communicates through the proximal end 708 of the anchor body 702 along the axis 712 with the passageway 714. The distal opening comprises a plurality of distal openings that communicate from the exterior surface of the anchor body 702 through the sidewall 750 to the passageway 714.

In certain embodiments, the anchor body 702 includes a set of internal helical threads 717 near the proximal end 708 of the anchor body 702. In one embodiment, the internal helical threads 717 are in communication with the proximal opening 716. The internal helical threads 717 may serve to engage, partially engage, interface with or communicate with an interference member 770 positioned within the longitudinal passageway 714.

In the illustrative example of FIGS. 52-61, the distal openings include a first, more proximal superior opening 718 and a second, more distal superior opening 720. The first superior opening 718 and second superior opening 720 are formed through the sidewall 750 to communicate with the interior longitudinal passageway 714 and centered over the longitudinal axis of the anchor body 702. The first superior opening 718 and second superior opening 720 are spaced proximally away from the distal end 710 of the anchor body 702 and can be aligned with each other.

In the illustrative example of FIGS. 52-61, the proximal member 704 is generally cylindrical and has a sidewall 751 (FIG. 61) defining an exterior surface, a proximal end 752, a distal end 754, and a longitudinal axis coaxial with the anchor body longitudinal axis 712 extending between the proximal and distal ends 752, 754. An axial through bore 756 extends through the proximal member 704 from the proximal end 752 to the distal end 754 and communicates with the longitudinal passageway 714 of the anchor body 702.

At least one opening formed through the sidewall 751 of the proximal member 704 and/or through the sidewall 750 of the anchor body 702 allows one or more sutures to be routed through the anchor body 702 without passing through the proximal end of the proximal member axially through the axial through bore 756. In the illustrative example of FIGS. 52-61, a first, superior "U"-shaped opening 758 is formed through the sidewall 751 near the distal end 754 and a second, inferior "U"-shaped opening 759 is formed through the sidewall 751 near the distal end 754 which may be opposite the first opening 758.

The "U"-shaped openings intersect the frangible connection 706. While the proximal member 704 and anchor body 702 are joined, the "U"-shaped openings 758, 759 each have a closed perimeter. When the proximal member 704 and anchor body 702 are separated at the frangible connection 706, the distal perimeter of each opening 758, 759 is removed such that separation of the proximal member 704 and anchor body 702 at the frangible connection 706 transforms the opening 758, 759 into open, "U"-shaped slots with the open side facing distally.

The proximal member 704 includes an engagement portion for engaging a driver, inserter, tensioner, or other instrument. In the illustrative example of FIGS. 52-61, the engagement portion includes external helical threads 760 operable to engage a driver, inserter, tensioner, or other instrument for deployment of the suture anchor 700.

In the illustrative example of FIGS. 52-61, the interference member 770 is operable to axially slide into the longitudinal passageway 714 of the anchor body 702 to secure a suture within the longitudinal passageway 714 by compressing the suture between the interference member 770 and the anchor body 702. In certain embodiments, the interference member 770 is embodied as a set screw. In one embodiment, the interference member 770 is a set screw that may be similar, or the same, in structure, function, and construction to embodiments of a set screw recited in U.S. Pat. No. 10,682,131, issued Jun. 16, 2020, which is hereby incorporated by reference in its entirety.

In the illustrative example of FIGS. 61-65, the interference member 770 has a body 772 having a proximal end 774, a distal end 776, and a longitudinal axis 778 extending between the proximal and distal ends 774, 776. The body 772 has a dimension perpendicular to the longitudinal axis 778 less than or equal to the diameter of the longitudinal passageway 714. Preferably the body 772 tapers distally. More preferably the body 772 tapers to a point 780.

The interference member 770 includes one or more external helical threads 782 on an external surface of the interference member 770. In various embodiments, the interference member 770 can include a variety of thread designs, each having one or more of a number of thread pitch configurations and/or sizes. In the illustrated embodiment, the external helical threads 782 of the interference member 770 are knuckle threads. The knuckle threads may have an external helical thread pitch that differs from an internal helical thread pitch of the internal helical threads 717 of the anchor body 702.

In the illustrative example of FIGS. 52-61, the interference member 770 can be inserted distally into the longitudinal passageway 714. In one embodiment, one or more of the external helical threads 782 may engage or interface with one or more internal helical threads 717 of the anchor body 702 to secure a portion of a suture within the longitudinal passageway 714 by compressing the portion of the suture between the interference member 770 and the anchor body 702. Said another way, the interference member 770 can be placed in the axial through bore 756 of the proximal member 704 at the proximal end 752 in axial sliding relationship so that the interference member 770 can exit the proximal member 704 and engage and/or interface with one or more internal helical threads 717 of the anchor body 702 to lock a suture in the anchor body 702.

Advantageously, the interference member 770 is configured to permit the interference member 770 to secure or lock a suture, or portion of a suture, in the anchor body 702 or release a suture, or portion of a suture, that is locked within the anchor body 702. In other words, the interference member 770 can be locked or unlocked (i.e., engaged or disengaged, secured or unsecured) within the anchor body 702 by way of the external helical threads 782 of the interference member 770, internal helical threads 717 of the anchor body 702, and the drive recess 790.

Figure 52:
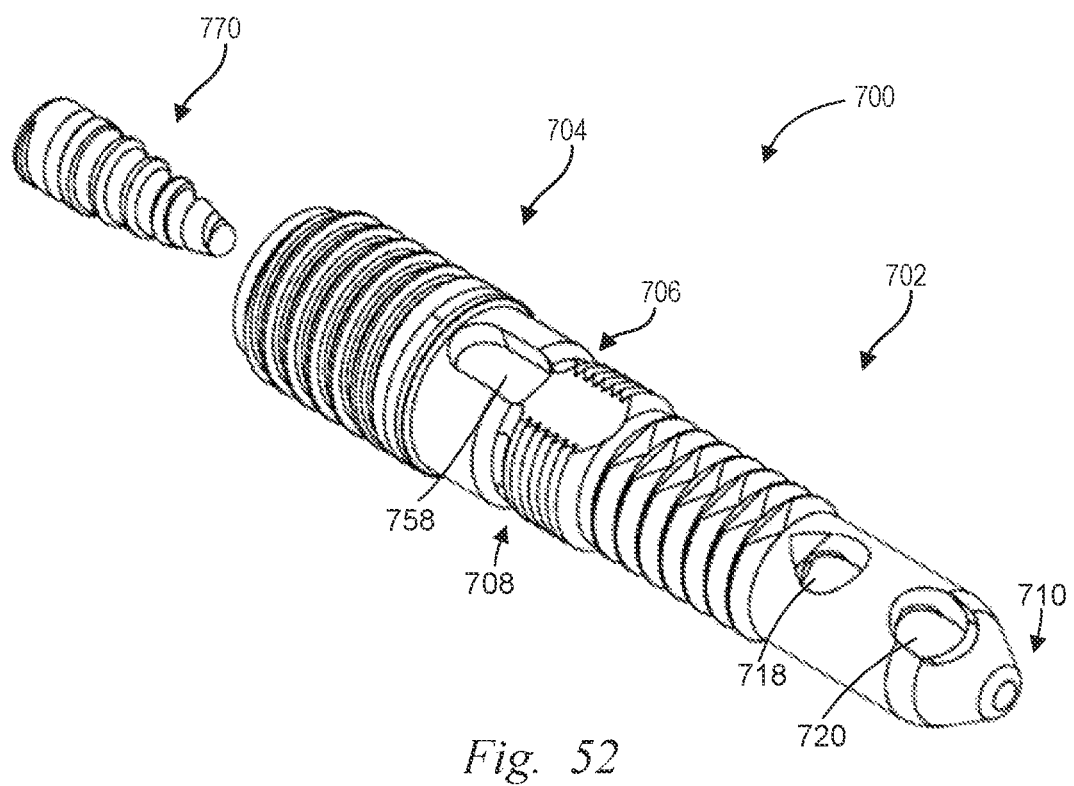
FIG. 52 is an exploded perspective view of an implant according to one embodiment.
Figure 53:
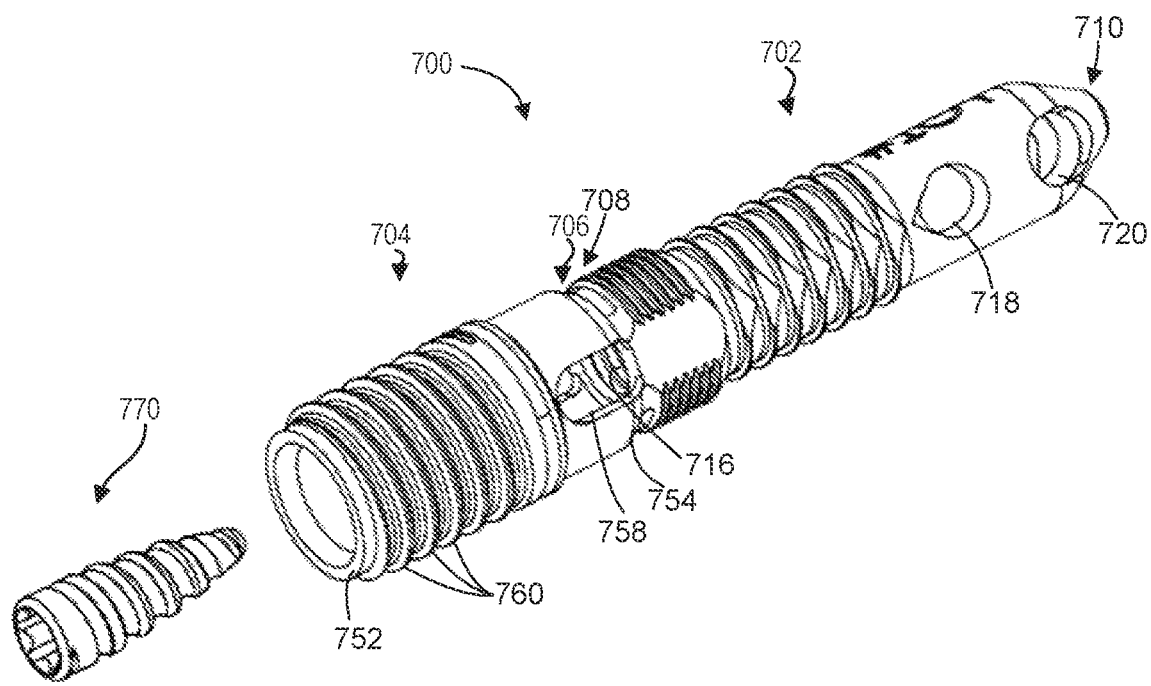
FIG. 53 is an exploded perspective view of an implant according to one embodiment.
Figure 54:
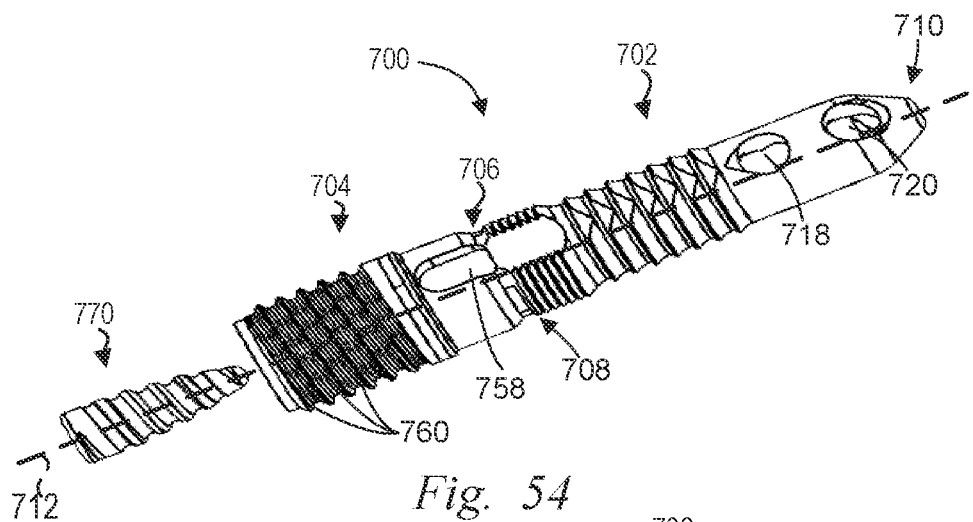
FIG. 54 is a perspective exploded view of an interference member and an implant of FIG. 52.
Figure 55:
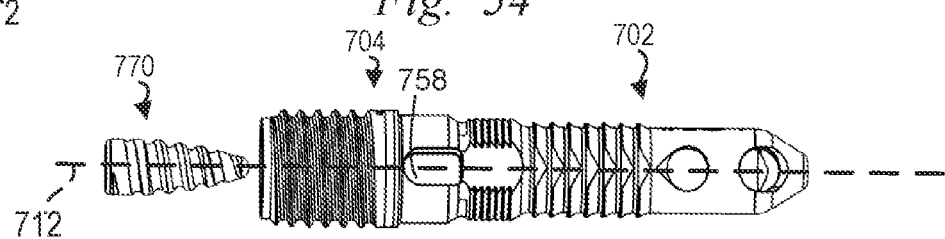
FIG. 55 is a top exploded view of the interference member and implant of FIG. 52 according to one embodiment.
Figures 56, 57, 58:
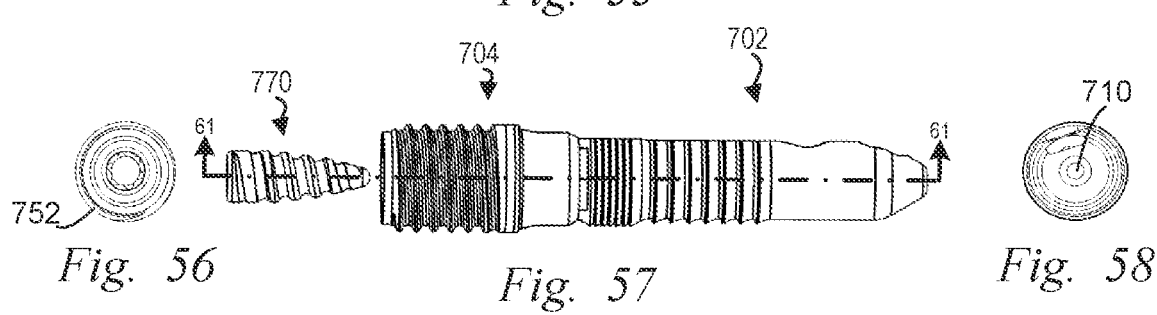
FIG. 56 is a left side exploded view of the interference member and implant of FIG. 52 according to one embodiment.
FIG. 57 is a front exploded view of the interference member and implant of FIG. 52 according to one embodiment.
FIG. 58 is a right exploded side view of the interference member and implant of FIG. 52 according to one embodiment.
Figure 59:
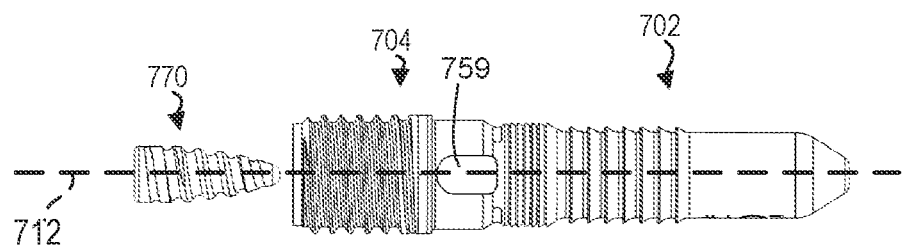
FIG. 59 is a bottom exploded view of the interference member and implant of FIG. 52 according to one embodiment.
Figure 60:
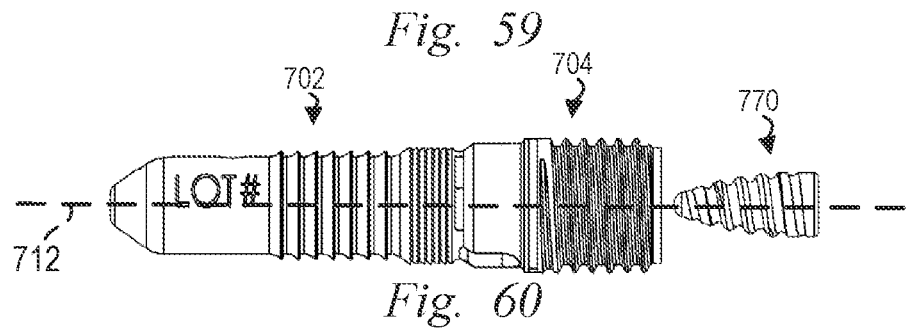
FIG. 60 is a back exploded view of the interference member and implant of FIG. 52 according to one embodiment.
Figure 61:
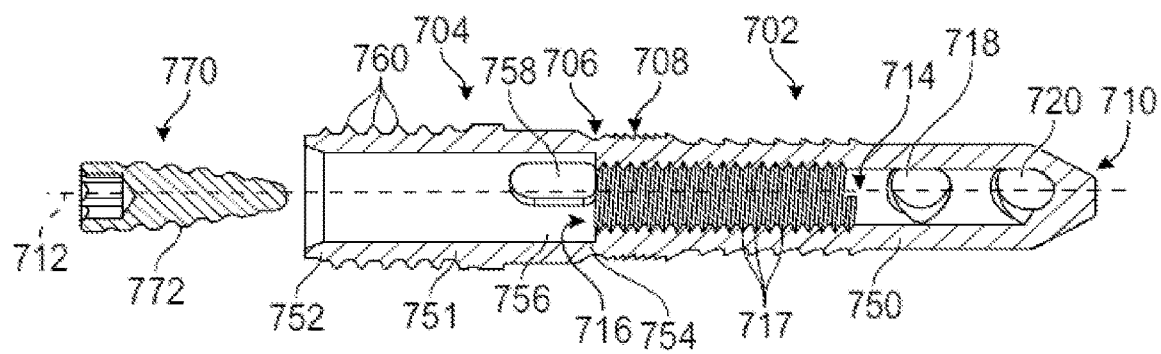
FIG. 61 is a side exploded section view of the interference member and implant of FIG. 52 taken along line 61-61 of FIG. 57.
Figures 62, 63, 64, 65:
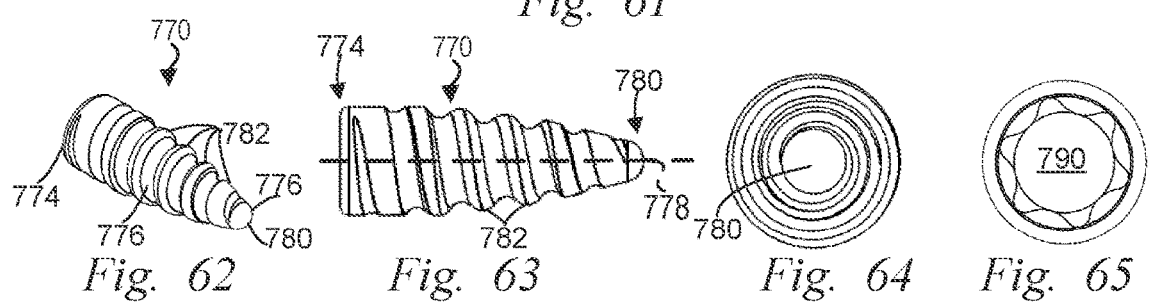
FIG. 62 is a perspective view of the interference member of FIG. 52 according to one embodiment.
FIG. 63 is a side view of the interference member of FIG. 52 according to one embodiment.
FIG. 64 is a right side view of the interference member of FIG. 52 according to one embodiment.
FIG. 65 is a left side view of the interference member of FIG. 52 according to one embodiment.

FIG. 62 is a perspective view of the interference member of FIG. 52 according to one embodiment. FIG. 63 is a side view of the interference member of FIG. 52 according to one embodiment. FIG. 64 is a right side view of the interference member of FIG. 52 according to one embodiment.

FIG. 65 illustrates an embodiment of an interference member 770 that includes a drive recess 790. In one embodiment, the drive recess 790 is configured to accept a drive feature of a driver. For example, the drive recess 790 may be in the shape of a torx recess for receiving a corresponding torx drive feature of a driver. Alternatively, or in addition, the drive recess 790 may receive a driver having a distal end in the shape of a point and configured to move distally within the longitudinal passageway 714 and thereby press the interference member 770 into the anchor body 702.

Figure 66:
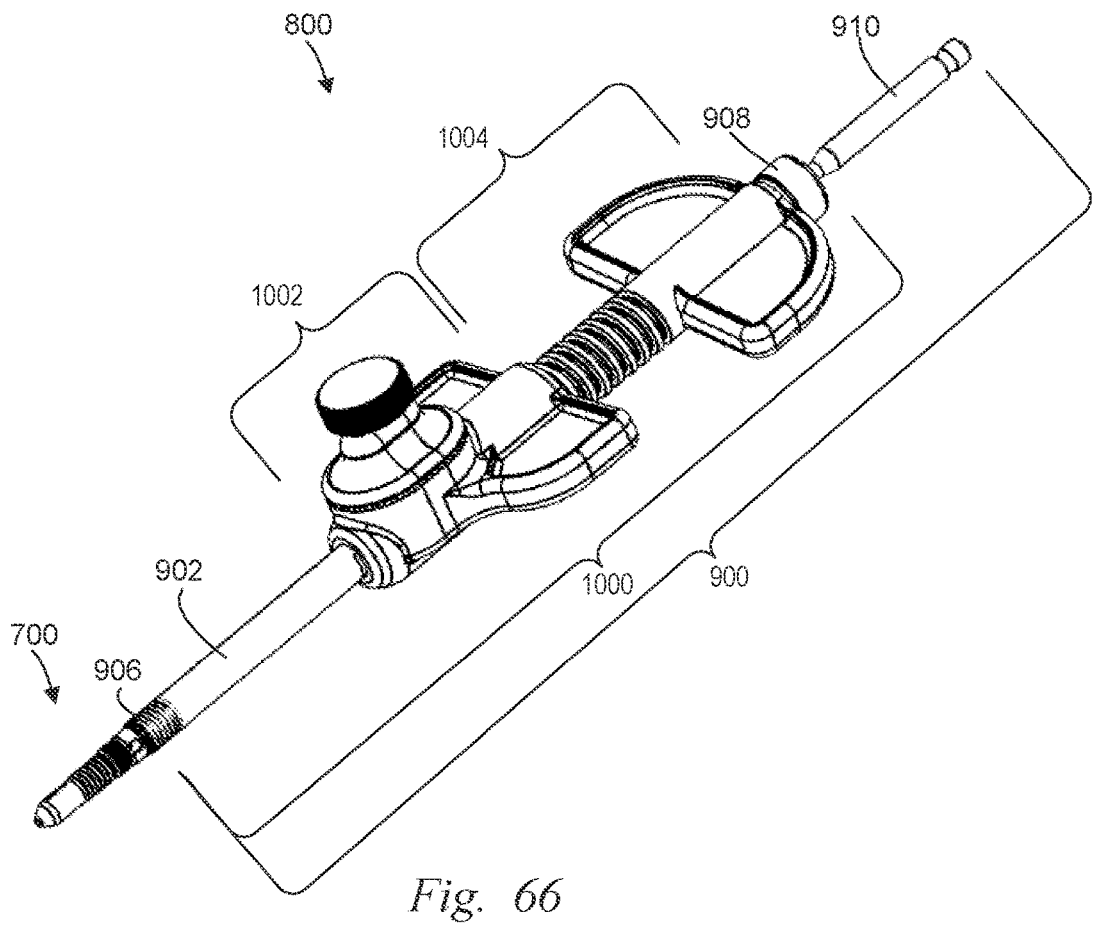
FIG. 66 is a perspective view of an instrument useable with the implant of FIG. 52 according to one embodiment.

FIG. 66 is a perspective view of a suture anchor system 800 useable with the implant of FIG. 52 according to one embodiment. The suture anchor system 800 may serve one or more different or related purposes or functions. Consequently, the suture anchor system 800 may be referred to by different names. In one embodiment, the suture anchor system 800 is referred to as a tensioner. Alternatively, or in addition, the suture anchor system 800 can be referred to as an inserter. In still another embodiment, such as the examples illustrated, the suture anchor system 800 may also be referred to as an inserter 900 that includes a tensioner 1000.

The suture anchor system 800 can be used to insert a suture anchor 700 into tissue of a patient or into a cavity, such as a bone tunnel of a patient. Alternatively, or in addition, the suture anchor system 800 can be used to tension and secure one or more sutures and/or one or more portions of sutures. In one embodiment, the one or more sutures and/or one or more portions of sutures may extend from the suture anchor 700.

Referring to FIGS. 66-70, the inserter 900 can include a shaft 902 having a proximal end 904 and a distal end 906, a collar 908, and a driver 910. The shaft 902 is operable and configured to engage the proximal member 704 of the suture anchor 700 at the distal end 906 of the shaft 902. In one embodiment, the shaft 902 includes internal threads 912 that engage external helical threads 760 (See FIG. 54) of the proximal member 704. The shaft 902 can also include external threads 914 (See FIG. 68) at or near the proximal end 904 of the shaft 902. The tensioner 1000 may include a carriage 1002, a puller 1004, and the shaft 902 and the collar 908 of the inserter 900. The tensioner 1000 is configured to engage the proximal member 704 of the suture anchor 700 and to secure a suture that may extend from the anchor body 702. In certain embodiments, the tensioner 1000 is operable and configured to apply tension to a suture, or portion of suture, that extends from the anchor body 702 of a suture anchor 700.

Referring to FIGS. 67-70, in one embodiment, the shaft 902 has an elongate cylindrical body 916. The shaft 902 may include three sections: first section 918, second section 920, third section 922. The first section 918 may have a first diameter and an exterior surface. The second section 920 may have a second diameter that is the same as the first diameter. In one embodiment, the second section 920 may include one or more planar surfaces 924. The planar surface 924 can serve to restriction rotation of the carriage 1002 about the shaft 902. In certain embodiments, having a single planar surface 924 the planar surface 924 creates a D-shaped cross-section within the second section 920.

In the illustrated embodiment, the second section 920 includes two opposite planar surfaces 924. In addition, the planar surfaces 924 may form one or more lips 926 or edges. The one or more lips 926 may serve to restrict movement of a carriage 1002 towards the distal end 906 of the shaft 902 past the one or more lips 926.

The third section 922 connects to and extends from the second section 920, just as the second section 920 connects to and extends from the first section 918. In one embodiment, the third section 922 includes a second diameter that is smaller than the first diameter. In certain embodiments, the planar surface(s) 924 can extend into the third section 922. The extending planar surfaces 924 can form one or more lips 928 between the second section 920 and the third section 922. These one or more lips 928 may serve to restrict movement of a puller 1004 towards the distal end 906 of the shaft 902 past the one or more lips 928. In one embodiment, the puller 1004 is connected to the shaft 902 near a proximal end 904 of the shaft 902.

The collar 908 can include proximal end 930, a distal end 932, and a head 934 connected to a shank 936. The collar 908 serves to secure the puller 1004 to the shaft 902. The collar 908 includes longitudinal opening 938 coaxial to a longitudinal axis of the collar 908. The shaft 902 includes a longitudinal opening 940 coaxial to a longitudinal axis of the shaft 902. Together the longitudinal opening 938 and longitudinal opening 940 can form an inserter longitudinal passageway 941. The inserter longitudinal passageway 941 is in communication with a longitudinal passageway 114, 514, 714 of the suture anchor 100, 500, 700. The inserter longitudinal passageway 941 enables instruments and other components to pass through the collar 908 and shaft 902 and into the suture anchor 700 or to engage with components of the suture anchor 700.

The head 934 is cylindrical and has a larger diameter than the shank 936. The longitudinal opening 938 pass through the head 934 and the shank 936. At the proximal end 930, the head 934 includes internal threads 942 within the longitudinal opening 938. At the distal end 932, the shank 936 includes internal threads 944 (See FIG. 70) within the longitudinal opening 938. The internal threads 944 are configured to engage the external threads 914 of the shaft 902.

FIGS. 71-73 illustrate a carriage 1002 of the tensioner 1000 of FIG. 66 according to one embodiment. The carriage 1002 can include a body 1006, a first handle 1008, and a suture grip member 1010. The first handle 1008 is configured and sized for easy grasping and use by a user's hands and figures.

The body 1006 can include an opening 1012 that passes through the body 1006 and is coaxial with a longitudinal axis of the carriage 1002. The carriage 1002 includes a proximal end 1014 and a distal end 1016. At the distal end 1016, the carriage 1002 includes internal threads 1018. The internal threads 1018 are configured to engage threads of a puller 1004. At the proximal end 1014, the carriage 1002 includes keyed opening 1020. The keyed opening 1020 is configured to accept the second section 920 of the shaft 902. In certain embodiments, FIG. 72 illustrates that the keyed opening 1020 may have a circular cross section and include opposite planar sides that correspond to the planar surfaces 924 on the shaft 902.

FIG. 74 illustrates one example of a puller 1004. In one embodiment, the puller 1004 includes an elongated body 1022 and a second handle 1024. The elongated body 1022 may have a circular cross section and have a longitudinal axis that is coaxial with an opening 1026 that passes through the elongated body 1022 from a proximal end 1028 to a distal end 1030. The opening 1026 is sized, at least on the proximal end 1028, to allow the puller 1004 to accept the collar 908. In one embodiment, the opening 1026 has a larger diameter on the proximal end 1028 of the puller 1004 than at, or near, the distal end 1030 of the puller 1004. In certain embodiments, a diameter of the opening 1026 at the distal end 1030 is smaller than a diameter of the second section 920 of the shaft 902 such that the distal end 1030 can contact the one or more lips 928 but does not slide past the one or more lips 928 along the shaft 902.

In certain embodiments, the puller 1004 can include external threads 1032 at, or near, the distal end 1030 of the puller 1004. The external threads 1032 can be configured with a suitable pitch and configuration such that the external threads 1032 can engage internal threads 1018 of the carriage 1002. Those of skill in the art of course appreciate that the carriage 1002 can include external threads and the puller 1004 can have corresponding internal threads.

FIGS. 75-78 illustrate a top view, a bottom view, a right side view, and a left side view of the system of FIG. 66 according to one embodiment. These figures illustrate that in one embodiment, the shaft 902, carriage 1002, and puller 1004 are coaxial with a longitudinal axis 1005. In the illustrated embodiment, the suture anchor system 800 includes a connected suture anchor 700. FIGS. 75 and 77 illustrate at least two sutures 1034 secured to the suture grip member 1010, the sutures 1034 are under tension.

Figure 79:
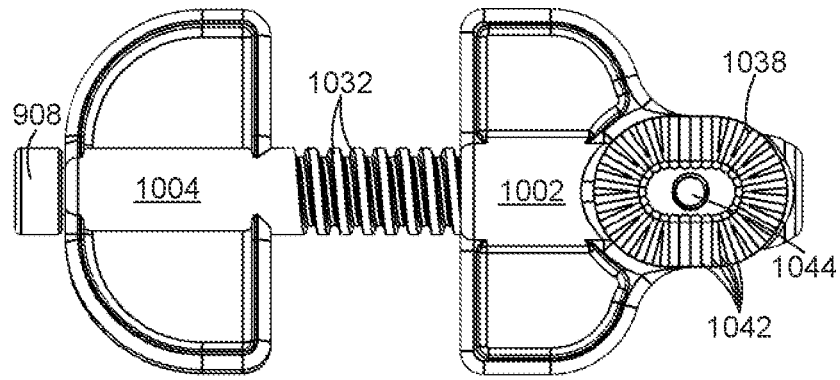
FIG. 79 is a top view of parts of the system of FIG. 66 according to one embodiment.
Figure 80:
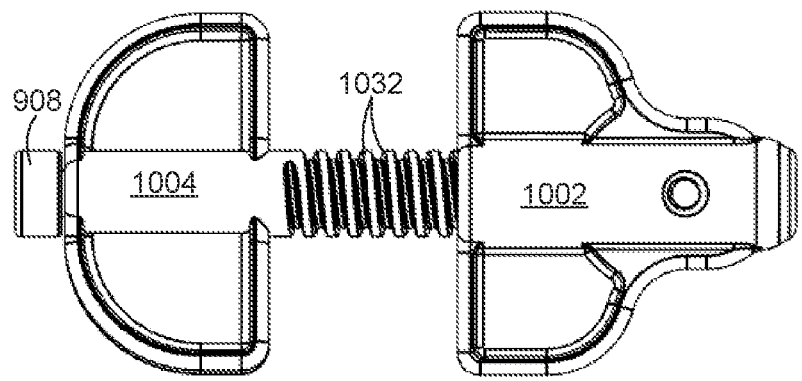
FIG. 80 is a bottom view of parts of the system of FIG. 66 according to one embodiment.
Figure 81:
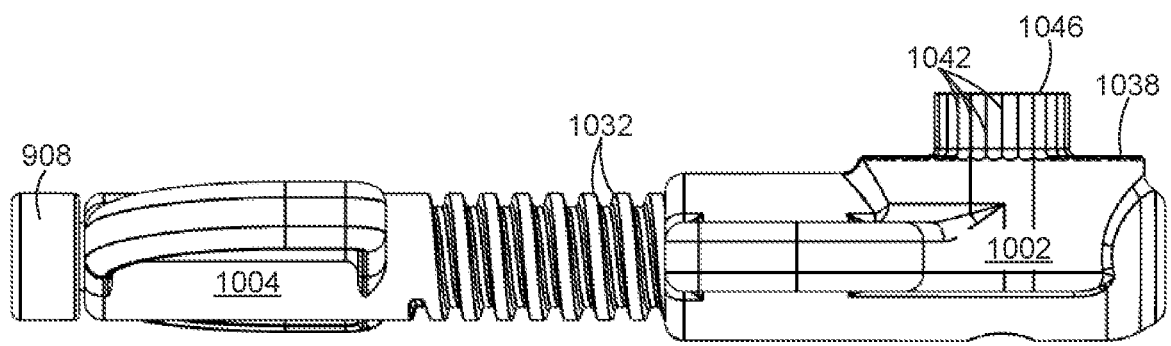
FIG. 81 is a front view of parts of the system of FIG. 66 according to one embodiment.

FIGS. 79-81 illustrate a top view, a bottom view, and a front view of the carriage 1002 and puller 1004 of FIG. 66 according to one embodiment. Note, parts of the suture grip member 1010 are omitted in FIGS. 79 and 80. In the illustrated embodiment, the carriage 1002 and puller 1004 are positioned as they would be when assembled for use. In particular, the carriage 1002 and puller 1004 are aligned along a common longitudinal axis and the external threads 1032 of the puller 1004 may be engaged with internal threads 1018 of the carriage 1002. The carriage 1002 and/or puller 1004 can be made from a variety of materials including metal, wood, plastic, ceramic, and the like.

FIGS. 79, 81, and 82-90 illustrate different views of different parts of a suture grip member 1010 which may be part of the tensioner 1000 according to one embodiment. The tensioner 1000 is configured, and is operable, to engage the proximal member 704 of the suture anchor 700 and secure one or more sutures 1034, or portions of sutures. In one embodiment, the one or more sutures 1034, or portions of sutures may extend from the anchor body. The suture grip member 1010 serves to removably, and/or adjustably, engage and/or secure a suture or portion of suture to the carriage 1002 before, during, and/or after a surgical procedure.

In one embodiment, the suture grip member 1010 includes superior grip plate 1036, an inferior grip plate 1038, and a fastener 1040. In certain embodiments, one or the other both the superior grip plate 1036 and the inferior grip plate 1038 can have one or more ridges 1042.

In one embodiment, the inferior grip plate 1038 can be integrated into the body 1006 of the carriage 1002. The inferior grip plate 1038 and/or the body 1006 can include an opening 1044 that extends at least partially into the body 1006 and may or may not connect to the opening 1012. The opening 1044 may include internal threads that are configured to engage external threads of the fastener 1040. The inferior grip plate 1038 can have a variety of shapes such as circular, oval, ovoid, square, elliptical, rectangular, or the like. In the illustrated embodiment, the inferior grip plate 1038 has a rectangular shape with two opposite curved ends that together form a slot shape.

Referring now to FIG. 81, the suture grip member 1010 may include a boss 1046 that extends from one of the grip plates 1036, 1038. In certain embodiments, the boss 1046 may also include one or more ridges 1042. In the illustrated embodiment, the boss 1046 extends from the inferior grip plate 1038.

Figure 82:
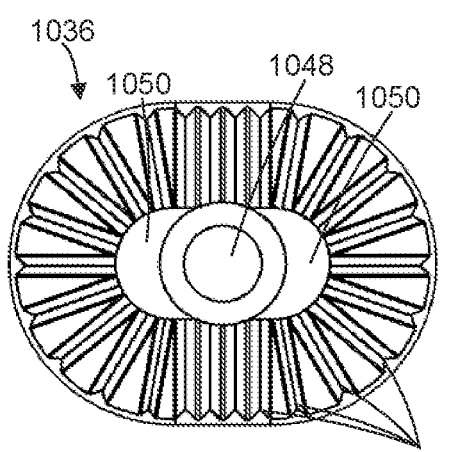
FIG. 82 is a bottom view of a grip plate of the system of FIG. 66 according to one embodiment.
Figure 83:
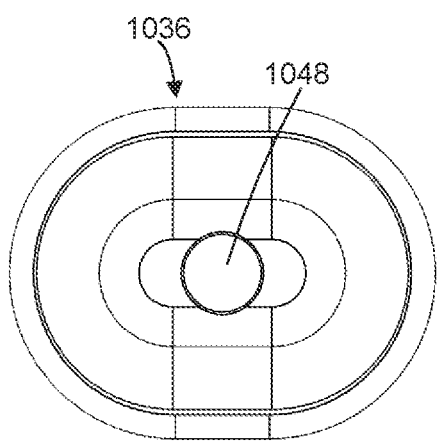
FIG. 83 is a top view of a grip plate of the system of FIG. 66 according to one embodiment.
Figure 84:
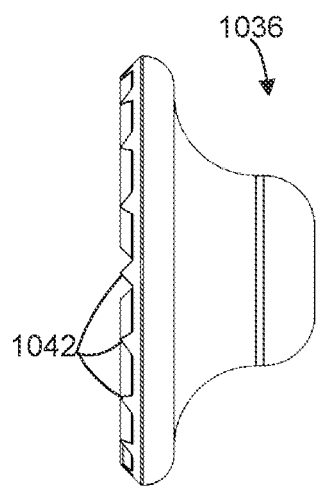
FIG. 84 is a side view of a grip plate of the system of FIG. 66 according to one embodiment.
Figure 85:
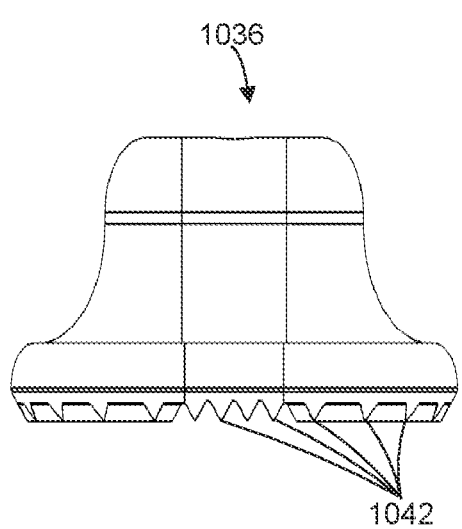
FIG. 85 is a front view of a grip plate of the system of FIG. 66 according to one embodiment.
Figure 86:
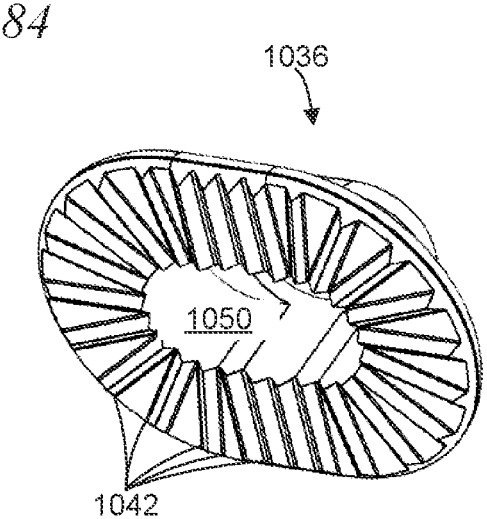
FIG. 86 is a bottom perspective view of a grip plate of the system of FIG. 66 according to one embodiment.
Figure 87:
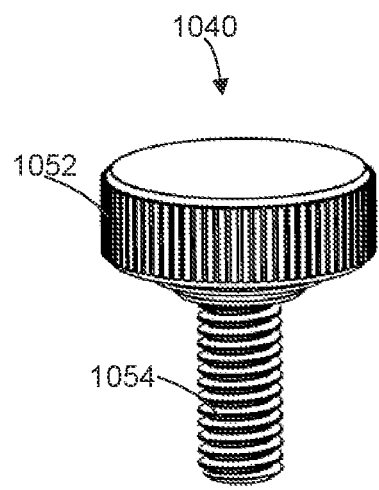
FIG. 87 is a perspective view of a fastener of the system of FIG. 66 according to one embodiment.
Figure 88:
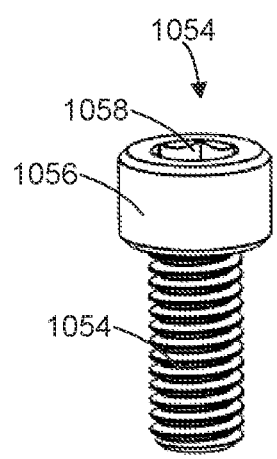
FIG. 88 is a perspective view of part of a fastener of the system of FIG. 66 according to one embodiment.
Figure 89:
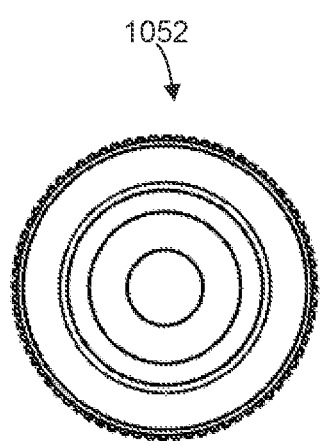
FIG. 89 is a bottom view of part of a fastener of the system of FIG. 66 according to one embodiment.
Figure 90:
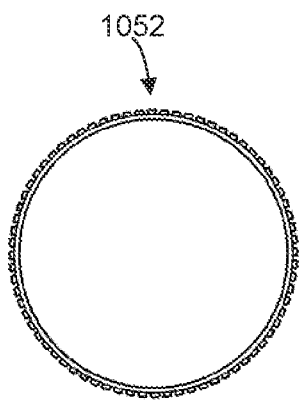
FIG. 90 is a top view of part of a fastener of the system of FIG. 66 according to one embodiment.

FIG. 82 illustrates one embodiment of a superior grip plate 1036. As with the inferior grip plate 1038, the superior grip plate 1036 can have a variety of shapes such as circular, oval, ovoid, square, elliptical, rectangular, or the like. In the illustrated embodiment, the superior grip plate 1036 has a rectangular shape with two opposite curved ends that together form a slot shape. The superior grip plate 1036 can include an opening 1048 that extends through the superior grip plate 1036. The opening 1048 may be sized and shaped to receive the fastener 1040.

The superior grip plate 1036 may also include a recess 1050. The recess 1050 may extend from an inferior surface of the superior grip plate 1036 into the superior grip plate 1036 but not extend completely through the superior grip plate 1036. In one embodiment, the recess 1050 is sized and shaped to receive the boss 1046. In one embodiment, the boss 1046 and recess 1050 are sized and shaped such that the boss 1046 can be inserted into the recess 1050 and have a clearance fit. In certain embodiments, the fit may be a friction fit.

The superior grip plate 1036, inferior grip plate 1038, boss 1046, recess 1050, one or more ridges 1042, and fastener 1040 cooperate to engage and secure one or more portions of suture positioned between the superior grip plate 1036 and inferior grip plate 1038, and/or between the boss 1046 and a wall of the recess 1050, and/or a combination of these. The fastener 1040 can compress the superior grip plate 1036 against the inferior grip plate 1038 and thereby secure a portion of a suture between the two plates and to the suture grip member 1010.

While certain embodiments, may not include one or more ridges 1042 on one or more of these components of the suture grip member 1010, having one or more ridges 1042 can enhance the engagement of the suture grip member 1010 with the suture. Such increased and/or enhanced engagement can enable greater tension to be applied to the suture coupled to the suture grip member 1010.

Referring to FIGS. 87-90, the fastener 1040 can be a thumb screw having a cap 1052 and a shank 1054. The cap 1052 may have a relatively large diameter as compared to the shank 1054. The cap 1052 may fit over a head 1056 of the shank 1054 by way of an interference or friction fit. In one embodiment, the shank 1054 may include external threads that engage within an opening 1044 of the inferior grip plate 1038 or body 1006. In one embodiment, the shank 1054 includes a drive recess 1058. As desired, a user may remove the cap 1052 and use a driver (not shown) to apply high torque to the shank 1054 to increase a compression force on the superior grip plate 1036 and/or inferior grip plate 1038.

Figure 91:
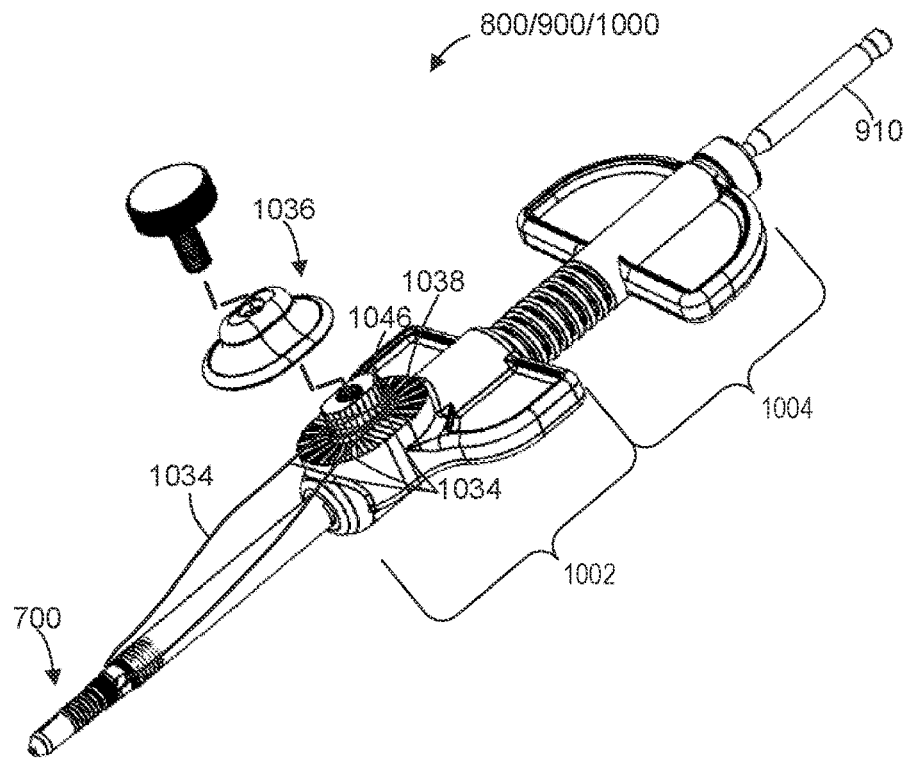
FIG. 91 is a perspective view of the system of FIG. 66 with portions exploded according to one embodiment.

FIG. 91 illustrates in a suture anchor system 800 how the fastener 1040 can pass through the superior grip plate 1036 and engage the inferior grip plate 1038. The boss 1046 fits within the recess 1050. The fastener 1040 may operate as a set screw to compress the superior grip plate 1036 and inferior grip plate 1038 to secure suture between the plates and/or the recess 1050 and boss 1046.

The suture anchor system 800 can include one or more sutures 1034 that may have been threaded through the suture anchor 700. The one or more sutures 1034 have been looped or wrapped around the boss 1046 and are positioned between the superior grip plate 1036 and inferior grip plate 1038. The one or more sutures 1034 may be under no tension and may set loose between the suture grip member 1010 and the suture anchor 700.

Figure 92:
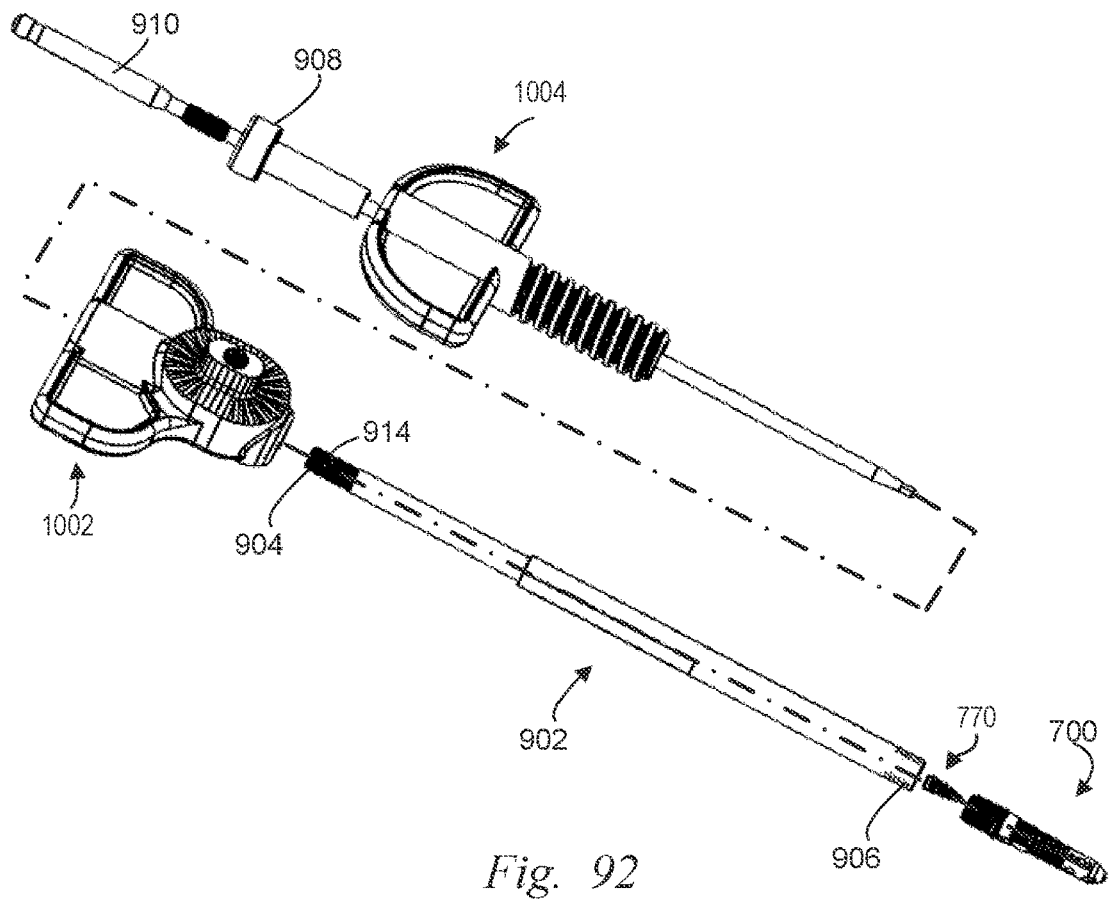
FIG. 92 is a perspective exploded view of the system of FIG. 66 according to one embodiment.
Figure 93:
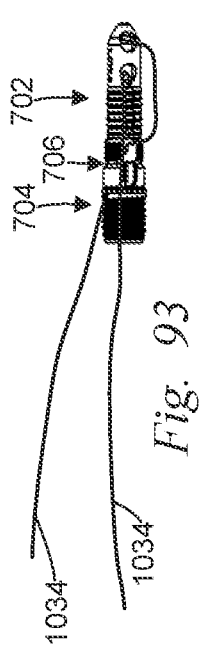
FIGS. 93-96 are a sequence of perspective views illustrating use of the system of FIG. 66 and the implant of FIG. 52 according to one embodiment.
Figure 94:
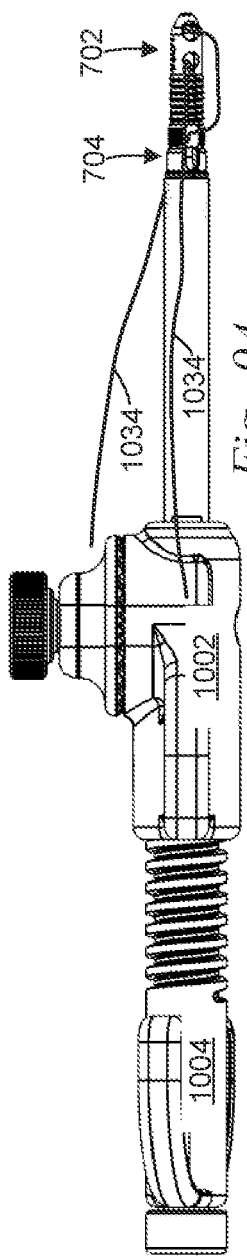

FIG. 92 is a perspective exploded view of the system of FIG. 66 according to one embodiment. The suture anchor system 800 can be assembled for use taking the following steps. First, the carriage 1002 can be slid along the shaft 902 from the proximal end 904 toward the distal end 906. The proximal end 904 is passed through the opening 1012 of the carriage 1002. Next, the carriage 1002 can be rotated such that the keyed opening 1020 accepts the second section 920 of the shaft 902. Once the keyed opening 1020 passes into the second section 920 the carriage 1002 may be rotationally fixed relative to the shaft 902.

Next, the puller 1004 is slid along the shaft 902 from the proximal end 904 toward the distal end 906. The puller 1004 is slid until the distal end 1030 contacts the one or more lips 928. Then, the collar 908 is screwed onto the shaft 902 by engaging the external threads 914 within the internal threads of the distal end 932 of the collar 908. At this stage of assembly, the external threads 1032 of the puller 1004 may or may not engage the internal threads 1018 of the carriage 1002. Also at this stage, the inserter 900/tensioner 1000 is ready for use in a surgical procedure.

In certain embodiments, a suture anchor 700 may be connected to the distal end 906 of the shaft 902 by way of the internal threads 912 and external helical threads 760 of the proximal member 704. Of course, this step can also be performed during a surgical procedure.

After the suture anchor system 800 is assembled, a user may insert the interference member 770 through the longitudinal opening 938 at the proximal end 930 of the collar 908 and pass the interference member 770 through the inserter longitudinal passageway 941 until the interference member 770 reaches the longitudinal passageway 714 of the suture anchor 700. In this manner, the interference member 770 can be inserted when needed during a surgical procedure to secure suture within the suture anchor 700.

In certain embodiments, the driver 910 can be used to move the interference member 770 through the inserter longitudinal passageway 941 and into the longitudinal passageway 714. Alternatively, or in addition, the driver 910 can be used to urge the interference member 770 into the anchor body 702.

FIGS. 93-96 are a sequence of perspective views illustrating use of the system of FIG. 66 and the implant of FIG. 52 according to one embodiment. Initially, a user, such as a surgeon, may thread one or more sutures 1034 through a suture anchor 700 having an anchor body 702 and proximal member 704 connected by a frangible connection 706. (See FIG. 93) Next, a user may connect an inserter 900 or tensioner 1000 or combination inserter/tensioner 900/1000 to the proximal member 704 by screwing the external helical threads 760 of the proximal member 704 into the internal threads 912 of the shaft 902. (See FIG. 94) At this stage, the one or more sutures 1034 may be loose and portions or ends of the one or more sutures 1034 may extend proximally towards the suture grip member 1010.

Figure 95:
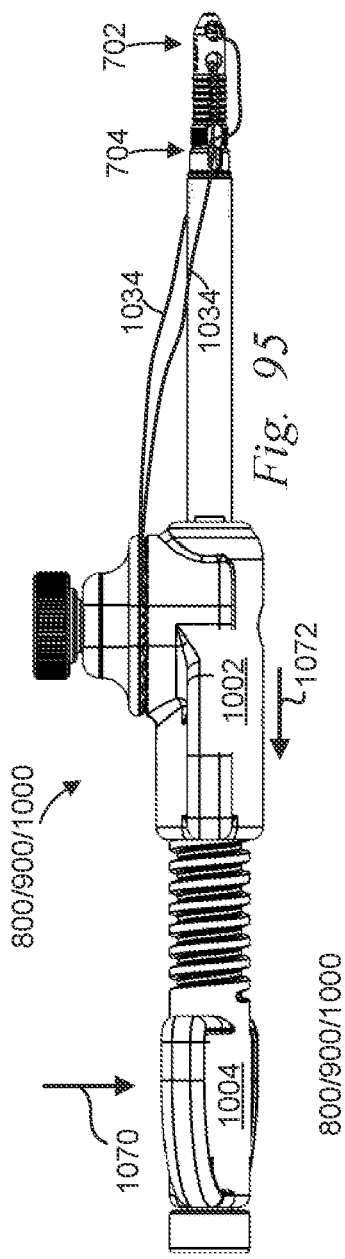

Next, a user may loosen the fastener 1040 such that the superior grip plate 1036 and inferior grip plate 1038 can be readily separated. In certain embodiments, the fastener 1040 can be removed and/or the superior grip plate 1036 removed. Referring now to FIG. 95, next a user inserts the one or more sutures 1034 or portions of the one or more sutures 1034 between the superior grip plate 1036 and inferior grip plate 1038. In certain embodiments, the user may wrap or wind the one or more sutures 1034 around the boss 1046. At this stage, a user may then re-connect or tighten the fastener 1040 to close and/or compress the superior grip plate 1036 against the inferior grip plate 1038 and thereby secure and/or tension the one or more sutures 1034 between the anchor body 702 and the suture grip member 1010. In one embodiment, a user may tighten the one or more sutures 1034 manually between the suture grip member 1010 and the anchor body 702 as the fastener 1040 compresses the superior grip plate 1036 against the inferior grip plate 1038. Next, a user may rotate the puller 1004 in a direction 1070.

Rotation of the puller 1004 in direction 1070 moves the external threads 1032 into the carriage 1002 by engagement with the internal threads 1018 of the carriage 1002. As the threads 1032, 1018 engage, this translates and moves the carriage 1002 proximally towards the puller 1004 in direction 1072. The translation of the carriage 1002 creates a translation force in direction 1072 which applies tension to the one or more sutures 1034.

The threads 1032, 1018 of the puller 1004 and carriage 1002 provide a significant mechanical advantage that increases tension in the one or more sutures 1034 secured between the anchor body 702 and the suture grip member 1010. Advantageously, reversing the rotation of the puller 1004 in a direction opposite direction 1070 loosens the one or more sutures 1034 such that a user can remove the one or more sutures 1034 or adjust the position or tension of the one or more sutures 1034.

Figure 96:
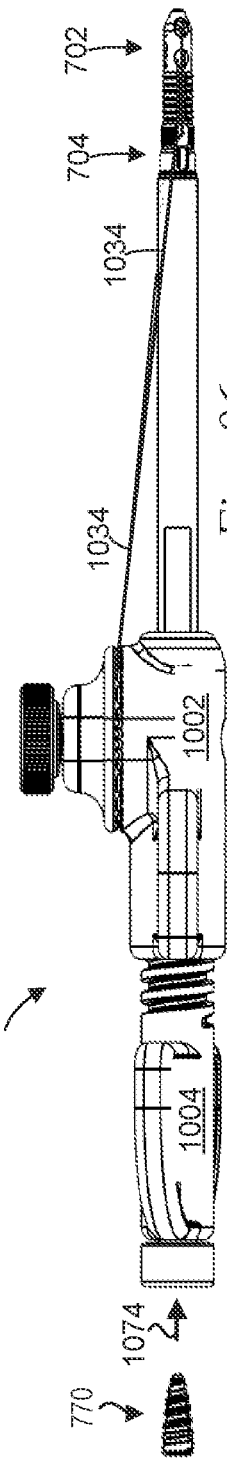

FIG. 96 illustrates the position of the carriage 1002 relative to the puller 1004 after a desired level of tension is placed into the one or more sutures 1034. Note that the carriage 1002 is closer to the proximal end 904 of the shaft 902 than before the one or more sutures 1034 were tightened. This causes more of the planar surface 924 of the second section 920 to be exposed. Next, a user can insert the interference member 770 distally within the inserter longitudinal passageway 941 in the direction indicated by arrow 1074. In one embodiment, the interference member 770 is inserted with the point 780 entering the inserter longitudinal passageway 941 first. The user can then urge the interference member 770 through the inserter longitudinal passageway 941 until the interference member 770 reaches the distal end 906 of the shaft 902 and enters the bore 756 of the proximal member 704. A user can move the interference member 770 through the inserter longitudinal passageway 941 and/or bore 756 using gravity or a tool such as a driver.

FIG. 97 illustrates one example of a driver 1080 that can be used to move the interference member 770 through the inserter longitudinal passageway 941 and/or bore 756. The driver 1080 may be cylindrical and elongated and may include a drive shaft 1082 having a proximal end 1084 and a distal end 1086. The driver 1080 also includes a drive coupler 1088, external drive threads 1090, and a drive feature 1092.

The drive coupler 1088 is connected to the drive shaft 1082 at the proximal end 1084. The drive coupler 1088 can be any of a variety of existing couplers suitable for connecting a tool that can rotate the driver 1080 about its longitudinal axis, move the driver 1080 axially, or transmit an axial force through the driver 1080. In one embodiment, the drive coupler 1088 is a conventional Association for Osteosynthesis (AO) quick connect having a D-shaped cross section and a groove for engaging a driving mechanism. The drive mechanism (not shown) may be a manual mechanism such as a handle adapted to engage the drive coupler 1088 or a powered mechanism, such as a drill.

In certain embodiments, the driver 1080 may include external drive threads 1090 in other embodiments, the driver 1080 may not include external drive threads 1090. In one embodiment, the external drive threads 1090 can be configured to engage internal threads 942 within the longitudinal opening 938 of the collar 908 (i.e., within the inserter 900). The external drive threads 1090 may be positioned along the drive shaft 1082 between the proximal end 1084 and distal end 1086 such that the external drive threads 1090 engage the internal threads 942 when the drive shaft 1082 is inserted within the inserter longitudinal passageway 941 far enough that the external helical threads 782 of interference member 770 can engage the internal helical threads 717 of the anchor body 702 as the external drive threads 1090 engage more of the internal threads 942. In this manner, the external drive threads 1090 may provide a mechanical advantage to assist in driving the interference member 770 into the anchor body 702.

In embodiments without external drive threads 1090, the drive shaft 1082 can still be used to urge the interference member 770 into the anchor body 702 (note FIGS. 97-104 are not necessarily drawn to scale). In such an embodiment, the drive shaft 1082 may press the interference member 770 towards the suture anchor 700 as the drive shaft 1082 is moved into the inserter longitudinal passageway 941. The drive shaft 1082 is long enough that the drive shaft 1082 can press the interference member 770 into and through the bore 756 such that the point 780 extends into the longitudinal passageway 714.

The drive feature 1092 is connected to the drive shaft 1082 at the distal end 1086. The drive feature 1092 can be configured to engage a drive recess 790 of an interference member 770. In one embodiment, the drive feature 1092 is a torx shape sized and configured to engage a drive recess 790 that is a torx recess.

FIG. 98 illustrates a stage in a sequence of using the suture anchor system 800 in another stage of the sequence illustrated in FIGS. 93-96. At this stage, the inserter 900 is connected to the suture anchor 700 and the tensioner 1000 is positioned to apply a desired level of tension to the one or more sutures 1034. A user has inserted the drive shaft 1082 into the inserter longitudinal passageway 941 and moved the interference member 770 until the point 780 extends into the longitudinal passageway 714 and the drive feature 1092 engages the drive recess 790 of the interference member 770. Next a user may attach a drive mechanism to the drive coupler 1088 and begin rotating the drive shaft 1082. This rotation causes at least one of the external helical threads 782 to engage with an internal helical thread 717 of the anchor body 702. Because the one or more sutures 1034 extend from the proximal opening 716 of the anchor body 702 from within the longitudinal passageway 714, engagement of at least one external helical thread 782 with an internal helical thread 717 of the anchor body 702 secures and compresses at least a portion of the one or more sutures 1034 between the interference member 770 and the anchor body 702. This engagement secures the one or more sutures 1034 with the same tension, or a slightly greater tension, in the one or more sutures 1034 that was present in the one or more sutures 1034 before the interference member 770 is screwed into the proximal opening 716 of the anchor body 702.

FIG. 99 is a perspective view of a driver 1080 for use within the system of FIG. 66 and the implant of FIG. 52 according to one embodiment. Specifically, FIG. 99 illustrates that the drive shaft 1082 can engage the interference member 770 as the interference member 770 is moved through the shaft 902 and into the suture anchor 700. FIG. 99 is not necessarily drawn to scale. The driver 1080 applies a torque to the interference member 770 and the least one or more external helical threads 782 of the interference member 770 to engage and/or mesh with at least one or more internal helical threads 717 of the anchor body 702.

The drive shaft 1082 is long enough to drive the interference member 770 by way of rotation to move completely into the longitudinal passageway 714. Rotation of the driver 1080 in a first direction causes at least one or more external helical threads 782 of the interference member 770 to engage and/or mesh with at least one or more internal helical threads 717 of the anchor body 702. Rotation of the driver 1080 in a second direction opposite the first direction causes external helical threads 782 of the interference member 770 to disengage from one or more internal helical threads 717 of the anchor body 702.

Advantageously, the drive feature 1092 of the driver 1080 and the drive recess 790 of the interference member 770 can be used both to insert, or drive, the interference member 770 axially into the anchor body 702 and to extract, remove, or back-out the interference member 770 from the anchor body 702. The ability to back the interference member 770 out of the anchor body 702 may be useful to a surgeon who desires to adjust tension in the one or more sutures 1034, remove the suture anchor 700, reposition the suture anchor 700, reconfigure or remove the one or more sutures 1034, or the like. This added flexibility can increase the options to a surgeon using the suture anchor 700 and can lead to move favorable surgical outcomes.

In certain embodiments, the drive feature 1092 and drive recess 790 may have a configuration different from the one illustrated. For example, the drive recess 790 may be a recess that includes a lip or hook and the drive feature 1092 may include a corresponding hook or lip that engages the one on the interference member 770. In this manner the drive feature 1092 may couple to the interference member 770 and permit one or both of axial force transmission and torque transmission from the driver 1080 to the interference member 770. Such alternative embodiments are within the scope of the present disclosure and enable the driver 1080 to move the interference member 770 into and retract the interference member 770 out of the anchor body 702.

FIGS. 100-101 are a sequence of perspective views illustrating use of the system of FIG. 66 and the implant of FIG. 52 according to one embodiment after the stage shown in FIG. 98. FIG. 100 shows that after the interference member 770 is secured within the longitudinal passageway 714, the driver 1080 can be removed.

At this stage, the suture anchor system 800 is prepared for disengagement/separation of the anchor body 702 from the proximal member 704. Also at this stage, the suture anchor 700 may already be inserted/placed/deployed within a patient. Alternatively, or in addition, a user may now, at this stage, deploy or insert the suture anchor 700 into a prepare location in a patient. In such an embodiment, the user may use the inserter 900 to position and press the suture anchor 700 into the desired location. The elongated inserter 900 and securely connected suture anchor 700 facilitate positioning and placement. In certain embodiments, the inserter 900 may be used for cannulated deployment.

Referring to FIG. 101, to separate the proximal member 704 from the anchor body 702, a user may insert a pushrod 1100 into the longitudinal opening 938 of the collar 908 at a proximal end of the suture anchor system 800/inserter 900. This mounts the pushrod 1100 for axial translation within the inserter 900. The pushrod 1100 may include many similar features and aspects as the driver 1080. In certain embodiments, a driver 1080 can be used to serve the dual purposes of a driver 1080 and/or of a pushrod 1100.

Referring now to FIGS. 101-104, consequently, the pushrod 1100 may be an elongated cylindrical structure having a proximal end 1110, a distal end 1120, a coupler 1130, much like the drive coupler 1088 of the driver 1080, external threads 1140, much like the external drive threads 1090, a shaft 1150, much like the drive shaft 1082, and a push feature 1160. The coupler 1130 may be an AO quick connect coupler. In certain embodiments, the push feature 1160 is the same as the drive feature 1092. In the illustrated embodiment, the push feature 1160 is different from the drive feature 1092, the push feature 1160 does not include a torx or other drive shaped end. In the illustrated embodiment, the push feature 1160 includes a tapering diameter to a blunt end that fits within the drive recess 790 of the interference member 770. In other embodiments, the push feature 1160 may have a diameter wider than the drive recess 790 can may contact a top of the interference member 770. In another embodiment, the push feature 1160 may have a diameter or configuration that contacts the sidewall 750 of the anchor body 702.

Figure 102:
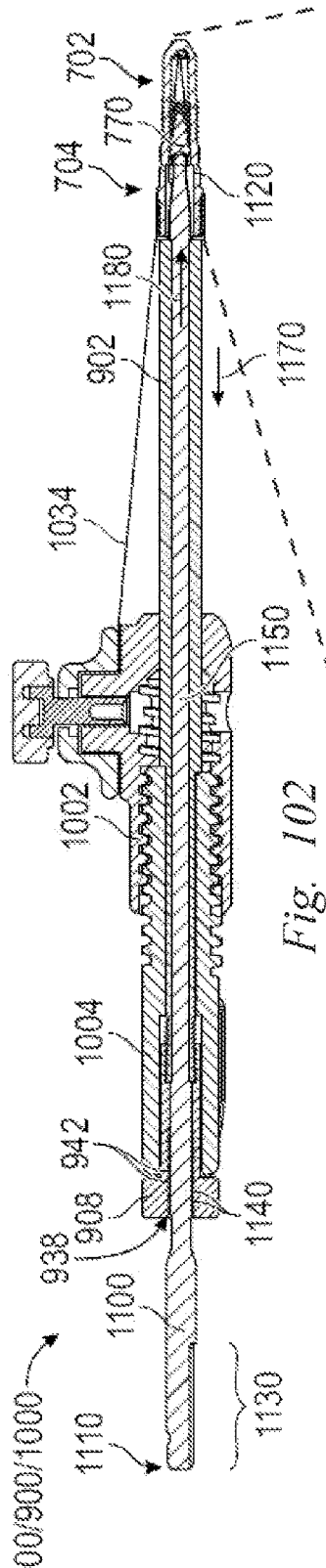
FIG. 102 is a section view illustrating use of the system of FIG. 66 and the implant of FIG. 52 according to one embodiment.
Figure 103:
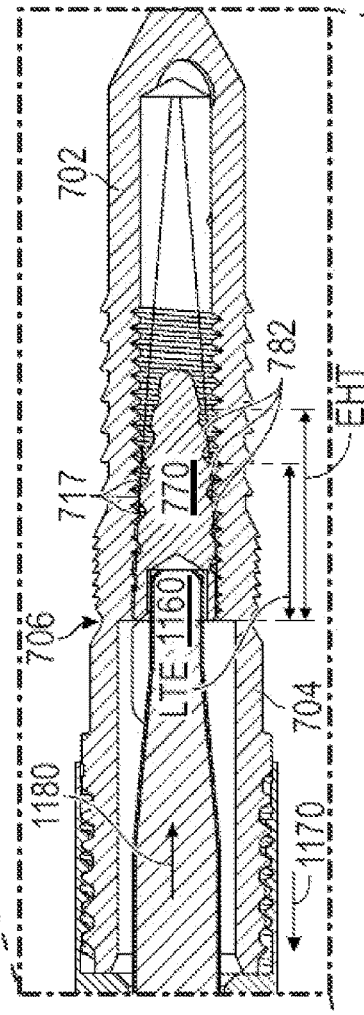
FIG. 103 is a close-up section view illustrating part of FIG. 102 according to one embodiment.
Figure 104:
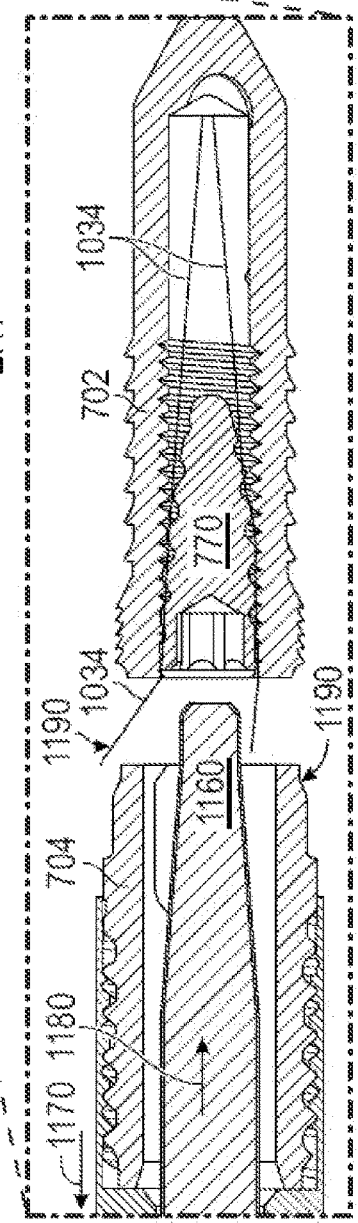
FIG. 104 is a close-up section view illustrating part of FIGS. 102 and 103 according to separation stage of the implant of FIG. 52 according to one embodiment.

Referring further to FIGS. 102-104, subsequent sequences of steps can be taken after the pushrod 1100 is inserted into the inserter 900, as shown in FIG. 101. A user may rotate the pushrod 1100 such that the external threads 1140 may engage internal threads 942 of the collar 908. This threaded engagement provides a mechanical force that moves/drives the push feature 1160 against the interference member 770. In FIG. 102, the push feature 1160 contacts the interference member 770 within the drive recess 790.

FIG. 103 shows magnified/close-up details of this contact, the push feature 1160, the interference member 770, and the anchor body 702. Note the one or more sutures 1034 between the interference member 770 and the internal helical threads 717 of the anchor body 702. FIG. 103 also illustrates that in one embodiment one or more external helical threads 782 of the interference member 770 may contact and/or engage with one or more internal helical threads 717 of the anchor body 702 while others make no contact and/or are not engaged with corresponding threads. In one embodiment, the external helical threads 782 may be knuckle threads. The knuckle threads may have an external helical thread pitch that differs from an internal helical thread pitch of the internal helical threads 717 of the anchor body 702.

In particular, FIG. 103 illustrates that the external helical threads 782 interface with internal helical threads 717 in a clearance fit. This clearance fit has a length of thread engagement (Arrow LTE) that is shorter than a length of the external helical threads 782 (Arrow EHT). Advantageously, such an interface may provide strong reliable fixation of the one or more sutures 1034 within the anchor body 702 and still prevent severing the one or more sutures 1034 within the anchor body 702.

Returning to the sequence of operations, FIG. 103 illustrates that the shaft 902 of the inserter 900 engages the proximal member 704 in an axial force transmitting relationship in a first direction 1170. In the illustrated embodiment, the axial force transmitting relationship is that the shaft 902 holds the proximal member 704 in place and places an axial force on the proximal member 704 in direction 1170.

Once the push feature 1160 contacts the interference member 770 (or sidewall 750) a user may next connect the coupler 1130 to a manual or powered tool and rotate the pushrod 1100 such that the external threads 1140 and internal threads 942 move past each other and move the pushrod 1100 in second direction 1180. This interaction is referred to herein as an axial force transmitting relationship in the second direction 1180. In one embodiment, the user may couple the pushrod 1100 to a manual or powered mechanism that imparts an axial force, such as a pounding force towards the distal end of the inserter 900. In such an embodiment, a user may simply pound on the pushrod 1100 with a mallet or hammer. In these embodiments, the pushrod 1100 may not include external threads 1140.

In the illustrated embodiment, the mechanical advantage of the external threads 1140 and internal threads 942 create a significant force that presses the push feature 1160 against the interference member 770 and/or the anchor body 702. Eventually, this force causes the frangible connection 706 to break (See FIG. 104 broken frangible connection 1190) which separates the anchor body 702 from the proximal member 704. The anchor body 702 then remains within a patient and the one or more sutures 1034 remain under tension while the interference member 770 is deployed and the anchor body 702 is deployed.

Specific examples of the present disclosure have been described. However, it will be apparent to one skilled in the art that various changes and substitutions may be made within the scope of the present disclosure defined by the claims. Likewise, it is contemplated, and within the scope of the present disclosure, that the various features of the illustrative examples may be interchanged among the illustrative examples.

The following are further examples of the present disclosure.

A knotless suture anchor comprising:
- an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a distal opening communicating with the longitudinal passageway nearer the distal end; and
- a first portion of a suture extending within the longitudinal passageway between the proximal opening and the distal opening, a second portion of the suture contiguous to the first portion and extending out of the anchor body, a third portion of the suture contiguous to the second portion and extending within the longitudinal passageway proximally to distally, and a fourth portion of the suture contiguous to the third portion and extending along the exterior surface distally to proximally.

The knotless suture anchor of example 1 further comprising an interference member operable to axially slide into the longitudinal passageway and secure the first portion of the suture and the third portion of the suture within the longitudinal passageway by compressing the suture portions between the interference member and the anchor body.

The knotless suture anchor of example 1 further comprising a proximal member joined to the anchor body by a frangible connection, a proximal member axial passage within the proximal member, the proximal member axial passage containing an interference member coaxially aligned with the longitudinal passageway.

The knotless suture anchor of example 3 further comprising an interference member retainer having a retainer axial passage, the interference member retainer engaging the proximal member axial passage in axial sliding relationship, the interference member engaging the retainer axial passage in axial sliding relationship.

The knotless suture anchor of example 4 further comprising an inserter operable to engage the proximal member in axial force transmitting relationship in a first direction, the inserter having a pushrod mounted for axial translation within the inserter, the pushrod being operable to engage the interference member in axial force transmitting relationship in a second direction opposite the first direction and expel the interference member from the proximal member into the anchor body, the pushrod being further operable to engage the interference member retainer in axial force transmitting relationship to press the interference member retainer against the anchor body and separate the anchor body and proximal member at the frangible connection.

The knotless suture anchor of example 1 wherein the anchor body has a plurality of distal openings.

The knotless suture anchor of example 6 wherein the plurality of distal openings comprises a single opening on a first side of the anchor body and a pair of openings on a second side of the anchor body opposite the first side.

The knotless suture anchor of example 6 wherein the plurality of distal openings comprises first and second openings through a sidewall of the anchor body nearer the distal end than the proximal end.

The knotless suture anchor of example 6 wherein the first portion of the suture passes through at least one of the plurality of distal openings and the third portion of the suture passes through at least another of the plurality of distal openings.

A knotless suture anchor comprising:
  an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a first distal opening communicating with the longitudinal passageway nearer the distal end than the proximal end;
  a proximal member joined to the anchor body by a frangible connection, the proximal member having a proximal member axial passage.

The knotless suture anchor of example 10 further comprising an interference member held by the proximal member and coaxially aligned with the longitudinal passageway.

The knotless suture anchor of example 11 wherein the interference member is mounted in axial sliding relationship within the proximal member and wherein the interference member is operable to slide axially out of the proximal member and into the longitudinal passageway of the anchor body.

The knotless suture anchor of example 11 wherein the anchor body further comprises a second distal opening.

The knotless suture anchor of example 13 wherein the anchor body further comprises a third distal opening, the first distal opening being on a first side of the anchor body and a the second and third openings being on a second side of the anchor body opposite the first side.

The knotless suture anchor of example 13 wherein the first and second distal openings are formed through a sidewall of the anchor body nearer the distal end than the proximal end, the first and second distal openings being aligned on the same side of the anchor body and spaced axially away from one another.

The knotless suture anchor of example 13 wherein the first and second distal openings have a continuous strand of suture material passing through them.

The knotless suture anchor of example 11 further comprising an interference member retainer having a retainer axial passage, the interference member retainer engaging the proximal member axial passage in axial sliding relationship, the interference member engaging the retainer axial passage in axial sliding relationship.

The knotless suture anchor of example 17 further comprising an inserter operable to engage the proximal member in axial force transmitting relationship in a first direction, the inserter having a pushrod mounted for axial translation within the inserter, the pushrod being operable to engage the interference member in axial force transmitting relationship in a second direction opposite the first direction and expel the interference member from the proximal member into the anchor body, the pushrod being further operable to engage the interference member retainer in axial force transmitting relationship to press the interference member retainer against the anchor body and separate the anchor body and proximal member at the frangible connection.

The knotless suture anchor of example 10 further comprising a first portion of suture extending within the longitudinal passageway and a second portion of suture contiguous to the first portion of suture extending from the anchor body.

The knotless suture anchor of example 19 further comprising a third portion of suture contiguous to the second portion of suture and extending within the longitudinal passageway proximally to distally.

The knotless suture anchor of example 20 further comprising a fourth portion of suture contiguous to the third portion and extending along the exterior surface distally to proximally.

The knotless suture anchor of example 20 further comprising a second distal opening communicating with the longitudinal passageway nearer the distal end than the proximal end, wherein the first portion of suture passes through one of the first and second distal openings and the third portion of suture passes through the other of the first and second distal openings.

The knotless suture anchor of example 19 further comprising a frangible elongate tube having a proximal end and a distal end, wherein the second portion of suture passes through the tube from the proximal end to the distal end.

The knotless suture anchor of example 13 further comprising:
  a first suture threader extending within the longitudinal passageway, the first suture threader extending through the proximal opening to a first threader loop end and the first suture threader extending through the first distal opening to a first threader grip end, the first threader loop end defining a suture capture loop; and
  a second suture threader extending within the longitudinal passageway, the second suture threader extending through the proximal opening to a second threader grip end and the second suture threader extending through the second distal opening to a second threader loop end, the second threader loop end defining a suture capture loop.

A knotless suture anchor comprising:
an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a distal opening communicating with the longitudinal passageway nearer the distal end;
a proximal member joined to the anchor body by a frangible connection, the proximal member having a sidewall defining a proximal member axial passage coaxial with the longitudinal passageway, the proximal member having an aperture through the sidewall adjacent to the frangible connection, the proximal member being operable to break away from the anchor body at the frangible connection causing the aperture to open distally.

The knotless suture anchor of example 25 further comprising an interference member mounted in the proximal member axial passage in coaxial sliding relationship.

The knotless suture anchor of example 25 wherein the anchor body has a plurality of distal openings.

The knotless suture anchor of example 27 wherein the plurality of distal openings comprises a single opening on a first side of the anchor body and a pair of openings on a second side of the anchor body opposite the first side.

The knotless suture anchor of example 27 wherein the plurality of distal openings comprises first and second openings through a sidewall of the anchor body nearer the distal end than the proximal end.

The knotless suture anchor of example 27 wherein at least two of the plurality of distal openings have suture material passing through them.

The knotless suture anchor of example 25 further comprising an interference member retainer having a retainer axial passage, the interference member retainer engaging the proximal member axial passage in axial sliding relationship, and an interference member engaging the retainer member axial passage in axial sliding relationship.

The knotless suture anchor of example 31 further comprising an inserter operable to engage the proximal member in axial force transmitting relationship in a first direction, the inserter having a pushrod mounted for axial translation within the inserter, the pushrod being operable to engage the interference member in axial force transmitting relationship in a second direction opposite the first direction and expel the interference member from the proximal member into the anchor body, the pushrod being further operable to engage the interference member retainer in axial force transmitting relationship to press the interference member retainer against the anchor body and separate the anchor body and proximal member at the frangible connection.

A knotless suture anchor comprising:
an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a plurality of distal openings communicating with the longitudinal passageway nearer the distal end, the plurality of distal openings comprising a single opening on a first side of the anchor body and a pair of openings on a second side of the anchor body opposite the first side; and
an interference member receivable within the longitudinal passageway.

A knotless suture anchor comprising:
an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a first distal opening communicating with the longitudinal passageway nearer the distal end;
a first suture extending through the longitudinal passageway with a proximal end exiting the proximal opening and a distal end exiting the first distal opening;
a suture keeper joined to the first suture proximal end, the suture keeper being operable to prevent the proximal end of the first suture from passing through the proximal opening.

The knotless suture anchor of example 34 wherein the proximal end of the first suture is tied to the suture keeper.

The knotless suture anchor of example 34 wherein the suture keeper comprises a planar member having a portion for receiving the anchor body and releasably retaining the anchor body on the planar member.

The knotless suture anchor of example 36 wherein the first suture is wrapped around the planar member.

The knotless suture anchor of example 37 further comprising a second suture strand and a second distal opening, the first suture strand exiting the first distal opening and the second suture strand exiting the second distal opening, the planar member defining a first recess for receiving the first suture strand wrapped around the planar member and a second recess for receiving the second suture strand wrapped around the planar member.

The knotless suture anchor of example 38 further comprising a frangible elongate tube having a proximal end and a distal end, wherein after exiting the distal openings of the anchor body, the first and second suture strands pass through the tube from the proximal end to the distal end.

The knotless suture anchor of example 39 further comprising a suture threader, the suture threader including a filament forming a loop portion and a grip portion joined to the loop portion, and further wherein the anchor body comprises a third distal opening, the loop portion extending through the longitudinal passageway from the third distal opening to the proximal opening with at least part of the loop portion extending out of the proximal opening and the grip portion extending out of the third distal opening.

A method of attaching a suture to a bone, comprising:
passing a portion of a suture through a bone so that a first portion of the suture extends from a first opening in the bone and a second portion of the suture extends from a second opening in the bone;
passing the second portion of the suture through a portion of a suture anchor body in a proximal to distal direction, the suture anchor body having a proximal end and a distal end;
passing the second portion of the suture alongside an outer surface of the suture anchor body in a distal to proximal direction; and
then inserting the suture anchor into the bone through one of the first and second openings, the distal end being inserted first through the opening.

The method of example 41 wherein the step of passing the second portion of the suture longitudinally through a portion of a suture anchor body in a proximal to distal direction comprises engaging the second portion of the suture with a first suture threader and pulling the suture threader through the anchor, the first suture threader being preloaded on the suture anchor.

The method of example 41 further comprising passing the first portion of the suture longitudinally through a portion of the suture anchor body in a distal to proximal direction.

The method of example 43 wherein the step of passing the first portion of the suture longitudinally through a portion of the suture anchor body in a distal to proximal direction comprises engaging the second portion of the suture with a second suture threader and pulling the suture threader through the anchor, the second suture threader being preloaded on the suture anchor.

The method of example 41 further comprising after inserting the suture anchor into a hole in the bone, advancing a locking member into the suture anchor to lock the suture to the anchor.

The method of example 44 further comprising before advancing the locking member, tensioning the suture.

The method of example 44 wherein a proximal member is joined to the proximal end of the anchor by a frangible connection, the method further comprising after advancing the locking member, separating the proximal member and anchor at the frangible connection.

The method of example 47 wherein the proximal member includes a hole through a sidewall adjacent the frangible portion and the suture extends through the hole, further wherein separating the proximal member and anchor transforms the hole into a distally opening slot and releases the suture distally from the slot.

A method of attaching a suture to a bone, comprising:
disengaging a first portion of a suture extending from a distal end of a suture anchor from a suture keeper, a second portion of the suture extending from a proximal end of the suture anchor being joined to the suture keeper;
then passing the first suture portion through a patient's body tissue;
then inserting the suture anchor body into a hole in a bone;
then separating the suture keeper from the second portion of the suture.

The method of example 49 wherein the second portion includes at least first and second strands of suture, the first strand being joined to a first portion of the suture keeper and the second strand being joined to a second portion of the suture keeper, the method further comprising independently tensioning the first and second strands.

The method of example 49 further comprising sliding the suture anchor over the first portion of suture away from the suture keeper while the second portion remains joined to the suture keeper.

A method of attaching soft tissue to bone, comprising:
passing a first portion of a suture through a bone;
passing the first portion through a soft tissue;
passing the first portion outside of a patient's body;
tying a knot in the first portion; and
pulling a second portion of the suture joined to the first portion to move the knot into the patient to a position adjacent to the soft tissue; and
securing the suture to the bone.

A method of attaching soft tissue to bone, comprising:
passing a tube through a portal in a patient's skin, the tube having a suture passing through it;
passing the suture through a soft tissue;
splitting the tube to free the suture from the tube; and
anchoring the suture to a bone.

A method of attaching a suture to a bone, comprising:
providing a suture anchor having a proximal end, a distal end, a longitudinal passage extending within the suture anchor in a proximal to distal direction, a first opening communicating with the longitudinal passage nearer the proximal end than the distal end, a second opening through the sidewall of the suture anchor nearer the distal end than the proximal end, and a third opening through the sidewall of the suture anchor nearer the distal end than the proximal end, a first suture threader extending within the longitudinal passage between the first and third openings, the first suture threader extending through the first opening to a grip portion outside of the longitudinal passage, the first suture threader extending through the third opening to a suture engaging portion outside of the longitudinal passage, a second suture threader extending within the longitudinal passage between the first and second openings, the second suture threader extending through the first opening to a suture engaging portion outside of the longitudinal passage, the second suture threader extending through the second opening to a grip portion outside of the longitudinal passage,
passing a portion of a suture through a bone so that a first portion of the suture extends from a first opening in the bone and a second portion of the suture extends from a second opening in the bone;
engaging the first portion of the suture with the first suture passer;
pulling on the grip portion of the first suture passer to pass the first portion of the suture through the longitudinal passage in a distal to proximal direction;
engaging the second portion of the suture with the second suture passer;
pulling on the grip portion of the second suture passer to pass the second portion of the suture through the longitudinal passage in a proximal to distal direction; and
then inserting the suture anchor into the bone through one of the first and second openings, the distal end being inserted first through the opening.

The method of example 54 further comprising:
passing the second portion of the suture through soft tissue;
tying a knot in the second portion of the suture outside of a patient's body; and
pulling on the first portion of the suture to move the knot nearer to the soft tissue.

The method of example 54 further comprising:
passing the first portion of the suture through a tube;
placing the tube and first portion of the suture through a portal in the patient's body;
splitting the tube to free the suture laterally from the tube.

The method of example 54 further comprising passing the second portion alongside an outer surface of the anchor in a distal to proximal direction.

The method of example 54 further comprising advancing a locking member in the longitudinal passage to secure the suture within the longitudinal passage.

The method of example 58 wherein a proximal member is joined to the proximal end of the anchor by a frangible connection, the proximal member housing the locking member, the step of advancing the locking member comprising pressing the locking member from the proximal member into the longitudinal passage, the method further comprising after advancing the locking member, separating the proximal member and anchor at the frangible connection.

The method of example 59 wherein advancing the locking member comprises actuating an inserter to press the locking member in a first direction while applying a counterforce to the proximal member in a second direction opposite the first direction, and wherein separating the proximal member and anchor comprises further actuating the inserter to break the frangible connection.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

As used herein, a "fastener" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Examples of fasteners include, but are not limited to wires, Kirschner wires, anchors, bone anchors, plates, bone plates, intramedullary nails or rods or pins, implants, interbody cages, fusion cages, and the like.

As used herein, a "set screw" refers to a type of screw generally used to secure a first object within, or against, second object, usually without using a nut. Set screws can be headless, meaning that the screw is fully threaded and has no head projecting past the thread's major diameter. If a set screw does have a head, the thread may extend to the head. A set screw can be driven by an internal-wrenching drive, such as a hex socket (Allen), star (Torx), square socket (Robertson), or a slot. A set screw can be driven by a knob on or part of a head of the set screw. The knob may be sized to facilitate rotation by a user using their fingers and may be referred to as a thumb screw. In one embodiment, the set screw passes through a threaded hole in the second object (an outer object) and is tightened against the first object (an inner object) to prevent the inner object from moving relative to the outer object. The set screw can exert a compressional and/or clamping force through an end of the set screw that projects through the threaded hole. (Search "set screw" on Wikipedia.com Aug. 17, 2020. Modified. Accessed Jan. 6, 2020.)

As used herein, a "thumb screw" refers to a type of fastener or screw designed and configured to be tightened, loosened, attached or detached using a person's fingers, such as a thumb and forefinger. In certain embodiments, a thumb screw may include a knob or button or wheel configured to grasped and rotated by an operator to tighten, loosen, attach or detach the thumb screw.

As used herein, "feature" refers to a distinctive attribute or aspect of something. (Search "feature" on google.com. Oxford Languages, 2021. Web. 20 Apr. 2021.) A feature may include one or more modifiers that identify one or more particular functions, attributes, advantages, or operations and/or particular structures relating to the feature. Examples of such modifiers applied to a feature, include, but are not limited to, "attachment feature," "securing feature," "alignment feature," "adjustment feature," "guide feature," "protruding feature," "engagement feature," "fixation feature", "disengagement feature," and the like.

As used herein, a "drive", "drive feature", or "drive recess" refers to an apparatus, instrument, structure, device, component, system, or assembly structured, organized, configured, designed, arranged, or engineered to receive a torque and transfer that torque to a structure connected or coupled to the drive. At a minimum, a drive is a set of shaped cavities and/or protrusions on a structure that allows torque to be applied to the structure. Often, a drive includes a mating tool, known as a driver. For example, cavities and/or protrusions on a head of a screw are on kind of drive and an example of a corresponding mating tool is a screwdriver, that is used to turn the screw, the drive. Examples of a drive include but are not limited to screw drives such as slotted drives, cruciform drives, square drives, multiple square drives, internal polygon, internal hex drives, penta lobular sockets, hex lobular sockets, combination drives, external drives, tamper-resistant drives, and the like. (Search 'list of screw drives' on Wikipedia.com Mar. 12, 2021. Modified. Accessed Mar. 19, 2021.)

As used herein, a "driver" refers to a mechanical piece, component, or structure for imparting motion to another piece, component, or structure. ("driver." Merriam-Webster.com. Merriam-Webster, 2021. Web. 6 Jan. 2021. Modified.) In certain embodiments, a driver can be a wheel configured or connected to other parts such that rotation or motion of the driver causes motion of other interconnected or intercoupled parts of a component, system, apparatus, or device.

As used herein, a "shaft" refers to a long narrow structure, device, component, member, system, or assembly that is structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickeltitanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

As used herein, a "thread" or "screw thread" refers to a helical structure used to convert between rotational and linear movement or force and/or to connect or engage two structures. A screw thread can be a ridge that wraps around a cylinder in the form of a helix, referred to as a straight thread. A screw thread can also be a ridge that wraps around a cone shape, referred to as a tapered thread. A screw thread is a feature of a screw as a simple machine and also in use as a threaded fastener. A screw thread can provide one or both of the following functions: conversion of rotary motion or force into linear motion or force and preventing or mitigating linear motion or force without corresponding rotation motion or force. In certain implementations of screw threads that convert a rotation force or torque into linear motion, or vice versa, the screw threads may be referred to as drive threads because of the drive function rotating the threads serves to extend or retract a structure linearly.

External screw threads are those formed on an external surface of a structure, such as a cylinder or cone shaped structure. Internal screw threads are those formed on an internal wall or surface of a nut, substrate, or opening. The cross-sectional shape of a thread is often called its form or threadform (also spelled thread form). The thread form may be square, triangular, trapezoidal, or other shapes. The terms form and threadform can refer to other design aspects taken together (cross-sectional shape, pitch, and diameters) in addition to cross-sectional shape, but commonly refer to the standardized geometry used by the screw. Major categories of threads include machine threads, material threads, and power threads. Generally, triangular threadforms are based on an isosceles triangle. These threadforms are usually called V-threads or vee-threads because of the shape of the letter V. For 60° V-threads, the isosceles triangle is, more specifically, equilateral. For buttress threads, the triangle is scalene.

The theoretical triangle shape for the thread form can be truncated to varying degrees (that is, the tip of the triangle is cut short). A V-thread in which there is no truncation (or a minuscule amount considered negligible) is called a sharp V-thread. Truncation occurs (and is codified in standards) for practical reasons.

The mechanical advantage of a screw thread depends on its lead, which is the linear distance the screw travels in one revolution. In general, the lead of a screw thread may be selected so that friction is sufficient to prevent linear motion or force from being converted to rotary, that is so the screw does not slip or disengage even when linear force is applied, as long as no external rotational force is present. A "length of thread engagement" refers to a distance that one set of threads (external or internal) engages another set of one or more threads (external or internal). The tightening of a fastener's screw thread is comparable to driving a wedge into a gap until the wedge sticks fast through friction and slight elastic deformation. (Search 'screw thread' on Wikipedia.com Jul. 16, 2021. Modified. Accessed Aug. 17, 2021.)

As used herein, a "knuckle threads" or "round threads" refers to a type of screw thread having a rounded thread form. The rounded thread form results in a space between the rounded crests and roots. This space provides space for material or debris to be shifted to not interfere with the thread and engaged within the space. This thread form is resistant to debris and thread damage. (Search 'knuckle thread' on Wikipedia.com Jan. 23, 2021. Modified. Accessed Aug. 17, 2021.)

As used herein, a "plate" refers to a flat structure. In certain embodiments, a plate can be configured to support a load. In certain embodiments, a plate may comprise a generally planar structure. A plate can be a separate structure connected to, or integrated with, another structure. Alternatively, a plate can be connected to part of another structure. A plate can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. A plate can be made from a variety of materials including, metal, plastic, ceramic, wood, fiberglass, or the like. One plate may be distinguished from another based on where the plate is positioned within a structure, component, or apparatus. For example, an "upper plate" can include a plate positioned on, near, or integrated with, a structure such that the plate is at, or near, a top of the structure. Similarly, a "lower plate" can include a plate positioned on, near, or integrated with, a structure such that the plate is at, or near, a bottom of the structure.

As used herein, a "recess" refers to hollow, pocket, void, opening, or depression formed in a surface. In certain embodiments, the recess does not pass through the structure having the surface. A recess can have a variety of cross-section shapes (e.g., ovoid, oval, round, circular, rectangular, square, or the like) and have a variety of configurations for one or more walls that define the recess. In one example, a recess can have one or more walls that connect in rounded corners. In certain embodiments, a recess is sized and shaped to receive or accept another structure.

As used herein, a "boss" refers to a protruding feature on a work piece or structure. A common use or feature for a boss is to locate one object within a pocket or hole of another object. (Search 'Boss (engineering)' on Wikipedia.com Aug. 13, 2021. Modified. Accessed Aug. 18, 2021).

As used herein, an "inserter" refers to an apparatus, instrument, structure, device, component, system, or assembly that is structured, organized, configured, designed, arranged, or engineered to insert or deploy one or more components, parts, or devices. In certain embodiments, an inserter can be used to insert implants and/or prosthesis into tissue, organs, or parts of a patient. In certain embodiments, an inserter can also be used to extract, retract, reposition, or remove an implant and/or prosthesis.

As used herein, "ridge" refers to a narrow, raised band on a surface or a structure that extends outwards from something. One or more ridges can be configured in a uniform relationship to each other, such as being parallel or extending radially from a common point. (Search "ridge" on wordhippo.com. WordHippo, 2021. Web. Accessed 18 Aug. 2021. Modified.)

As used herein, a "pushrod" refers to an instrument, structure, device, or component that is long and slender or narrow and structured, organized, configured, positioned, designed, arranged, and/or engineered to press or push against another structure, instrument, component, or device. (Search 'Valve train' on Wikipedia.com Jul. 15, 2021. Modified. Accessed Aug. 18, 2021.)

As used herein, a "clearance fit" refers to a type of engineering fit. An engineering fit is used in defining geometric dimensions and tolerances when designing a part or assembly. The fit is the clearance between two mating parts, and the size of this clearance determines whether the parts can, at one end of the spectrum, move or rotate independently from each other or, at the other end, are temporarily or permanently joined together. Engineering fits are generally described as a "shaft and hole" pairing but are not limited to just round components.

The three types of fit are: Clearance: The hole is larger than the shaft, enabling the two parts to slide and/or rotate when assembled, e.g., piston & valves; Location/transition: The hole is fractionally smaller than the shaft and mild force is required to assemble/disassemble e.g., Shaft key; and Interference: The hole is smaller than the shaft and high force and/or heat is required to assemble/disassemble e.g., Bearing bush.

As used herein, an "axial translation" refers to motion of one or more components along a common axis.

The phrases "connected to," "coupled to" and "in communication with" refer to any form of interaction between two or more entities, including mechanical, electrical, magnetic, electromagnetic, fluid, and thermal interaction. Two components may be functionally coupled to or in communication with each other even though they are not in direct contact with each other.

As used herein, "coupling" or "coupler" refers to a mechanical device, component, or structure, that is organized, configured, designed, arranged, or engineered to connect the ends of adjacent parts or objects. In certain embodiments, a coupling can be used to connect two shafts together at their ends for the purpose of transmitting power. In other embodiments, a coupling can be used to join two pieces of rotating equipment while permitting some degree of misalignment or end movement or both. Couplings do not normally allow disconnection of the two parts, such as shafts during operation. (Search "coupling" on Wikipedia.com Jul. 26, 2021. CC-BY-SA 3.0 Modified. Accessed Jul. 27, 2021.)

As used herein, an "axial force transmitting relationship" refers to a functional relationship between a first structure and a second structure. In this relationship, the structures interact with each other such that a force experienced or imparted by one structure (first or second) is transferred or transmitted to the other structure (first or second) along or in relation to a shared single axis. In certain embodiments, the first structure and second structure share a common axis. In other words, the two structures are coaxial. One axis, such as a longitudinal axis, is shared by both the first structure and the second structure.

As used herein, a "tensioner" refers to an apparatus, instrument, structure, device, component, system, or assembly that is structured, organized, configured, designed, arranged, or engineered to apply or increase tension in another structure, component, or device. The another structure, component, or device can be any of a variety of things including, but not limited to a thread, a suture, suture tape, a woven structure, a fibrous material, a cord, a ligament, cartilage, muscle, a ligament graft, and/or any of these in combination with each other, or the like. In certain embodiments, a tensioner can be used to release or relax tension in another structure, component, or device.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

What is claimed is:

1. A knotless suture anchor system comprising:
   an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a distal opening communicating with the longitudinal passageway nearer the distal end;
   an interference member insertable distally into the longitudinal passageway to secure a portion of a suture within the longitudinal passageway by compressing the portion of the suture between the interference member and the anchor body; and
   a frangible connection that joins a proximal member to the anchor body.

2. The knotless suture anchor system of claim 1 further comprising a driver operable to urge the interference member into the anchor body, and operable to move the interference member out of the anchor body.

3. The knotless suture anchor system of claim 2, wherein the driver comprises:
   a drive shaft having a proximal end and a distal end;
   a drive coupler connected to the drive shaft at the proximal end; and
   a drive feature connected to the drive shaft at the distal end.

4. The knotless suture anchor system of claim 2, wherein the driver is configured to apply a torque to the interference member that engages at least one external helical thread of the interference member with an internal thread of the anchor body.

5. The knotless suture anchor system of claim 1, wherein the proximal end of the anchor body includes internal helical threads and the interference member comprises a set screw having external helical threads configured to interface with the internal helical threads in a clearance fit having a length of thread engagement shorter than a length of the external helical threads.

6. The knotless suture anchor system of claim 5, wherein the external helical threads of the set screw comprise knuckle threads having an external helical thread pitch different from an internal helical thread pitch of the internal helical threads.

7. The knotless suture anchor system of claim 1, further comprising a tensioner operable to engage the proximal member and secure and tension a suture extending from the anchor body.

8. The knotless suture anchor system of claim 7, the tensioner comprising:
   a shaft having a proximal end and a distal end, the shaft operable to engage the proximal member at the distal end of the shaft;
   a carriage having a suture grip member that removably secures a portion of the suture to the carriage, the carriage having first threads;

a puller connected to the shaft near the proximal end of the shaft, the puller having second threads that engage the first threads; and wherein the shaft, carriage, and puller are coaxial with the longitudinal axis and include an inserter longitudinal passageway in communication with the longitudinal passageway of the anchor body.

9. The knotless suture anchor system of claim 8, wherein the suture grip member comprises:
a superior grip plate having ridges;
an inferior grip plate having ridges; and
a fastener that compresses the superior grip plate against the inferior grip plate and secure a portion of the suture between the superior grip plate and inferior grip plate.

10. The knotless suture anchor system of claim 9, wherein the fastener comprises a thumb screw and the superior grip plate comprises a recess that accepts a boss of the inferior grip plate, the boss having ridges.

11. The knotless suture anchor system of claim 1 further comprising an inserter operable to engage the proximal member in an axial force transmitting relationship in a first direction, the inserter having a pushrod mounted for axial translation within the inserter, the pushrod operable to engage one of the interference member and the anchor body in an axial force transmitting relationship in a second direction opposite the first direction and break the frangible connection between the proximal member and the anchor body in response to axial translation of the pushrod relative to the inserter.

12. A knotless suture anchor system comprising:
an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a first distal opening communicating with the longitudinal passageway nearer the distal end; and
a tensioner connected to the anchor body and operable to engage the proximal end, secure a suture extending from the anchor body, and apply tension to the suture; and
a proximal member connected to the proximal end of the anchor body by a frangible connection.

13. The knotless suture anchor system of claim 12 further comprising an interference member insertable distally into the longitudinal passageway to secure a portion of a suture within the longitudinal passageway by compressing the portion of the suture between the interference member and the anchor body.

14. The knotless suture anchor system of claim 13, further comprising an inserter operable to engage the proximal member in an axial force transmitting relationship in a first direction, the inserter having a pushrod mounted for axial translation within the inserter, the pushrod operable to engage the interference member in an axial force transmitting relationship in a second direction opposite the first direction and break the frangible connection between the proximal member and the anchor body in response to axial translation of the pushrod relative to the inserter.

15. The knotless suture anchor system of claim 14 wherein the inserter comprises a shaft having a proximal end and a distal end, the shaft operable to engage the proximal member at the distal end of the shaft, the shaft coupled to a tensioner comprising:

a carriage having a suture grip member that removably secures a portion of the suture to the carriage, the carriage having first threads;
a puller connected to the shaft near the proximal end of the shaft, the puller having second threads that engage the first threads; and
wherein the shaft, carriage, and puller are coaxial with the longitudinal axis and include an inserter longitudinal passageway in communication with the longitudinal passageway of the anchor body.

16. The knotless suture anchor system of claim 15 wherein the proximal member comprises external helical threads configured to engage internal helical threads of the shaft.

17. A knotless suture anchor system comprising:
an anchor body having an exterior surface, a proximal end, a distal end, a longitudinal axis extending between the proximal and distal ends, an interior longitudinal passageway extending at least partway from the proximal end toward the distal end, a proximal opening communicating with the longitudinal passageway nearer the proximal end, and a first distal opening communicating with the longitudinal passageway nearer the distal end;
a proximal member joined to the anchor body, the proximal member having external threads at a proximal end of the proximal member;
a set screw insertable distally into the longitudinal passageway to releasably secure a first portion of a suture within the longitudinal passageway by compressing the first portion of the suture between external knuckle threads of the set screw and internal helical threads at the proximal end of the anchor body;
a frangible connection that joins the proximal member to the anchor body; and
a tensioner connected to an inserter operable to engage the proximal member, the tensioner operable to secure a second portion of the suture contiguous to the first portion and extending from the anchor body, the tensioner also operable to apply tension to the second portion of the suture.

18. The knotless suture anchor system of claim 17 wherein the inserter is operable to engage the proximal member in an axial force transmitting relationship in a first direction, the inserter having a pushrod mounted for axial translation within the inserter, the pushrod operable to engage the set screw in an axial force transmitting relationship in a second direction opposite the first direction and break the frangible connection to separate the anchor body from the proximal member in response to axial translation of the pushrod relative to the inserter.

19. The knotless suture anchor system of claim 17 further comprising:
a driver operable to engage the set screw and to urge the set screw into the anchor body; and
wherein the driver comprises:
a drive shaft having a proximal end and a distal end;
a drive coupler connected to the drive shaft at the proximal end;
a drive feature connected to the drive shaft at the distal end; and
external drive threads between the proximal end and the distal end, the external drive threads configured to engage internal drive threads of the inserter.

* * * * *